(12) United States Patent
Brighty et al.

(10) Patent No.: US 6,313,100 B1
(45) Date of Patent: Nov. 6, 2001

(54) HYGROMYCIN DERIVATIVES

(75) Inventors: Katherine Elizabeth Brighty, Groton; Subramanian Sam Guhan, Niantic; Martin Raymond Jefson, Stonington; Robert Gerald Linde, III, Old Lyme; Ellen Lester McCormick, Waterford, all of CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/462,592

(22) PCT Filed: May 3, 1999

(86) PCT No.: PCT/IB99/00795

§ 371 Date: Jan. 7, 2000

§ 102(e) Date: Jan. 7, 2000

(87) PCT Pub. No.: WO99/57125

PCT Pub. Date: Nov. 11, 1999

Related U.S. Application Data

(60) Provisional application No. 60/084,042, filed on May 4, 1998.

(51) Int. Cl.[7] .......................... A61K 31/70; C07H 15/00; C12P 19/46
(52) U.S. Cl. .............................. 514/25; 514/23; 536/16.8; 536/17.9; 536/18.1; 435/79
(58) Field of Search ............................ 536/16.8, 17.9, 536/18.1; 519/25, 23; 435/79

(56) References Cited

FOREIGN PATENT DOCUMENTS

| 0236110A | 9/1987 | (EP) . |
| 0213692A | 3/1997 | (EP) . |

OTHER PUBLICATIONS

Hecker S. J. et al.: "Semisynthetic modification of hygromycin A. I. Synthesis and antibacterial activity of vinyl methyl and amide analogs"; *Bioorganic& Medicinal Chemistry Letters*, vol. 12, No. 6, 1992, pp. 533–536, XP002120208 cited in the application p. 533, paragraph 1—paragraph 2, p. 535, compound 16.

Hecker S. J. et al.: "Application of hygromycin A structure activity relationships to the antibiotic A201A"; *Bioorganic & Medicinal Chemistry Letters*, vol. 3, No. 2, 1993, pp. 295–298, XP002120209 cited in the application p. 295, paragraph 1, pp. 296, compound 7.

Hayashi, Shigeru F. Et Al.: "Structure–activity relationships of hygromycin A and its analogs: protein synthesis inhibition activity in a cell free system"; *J. Antibiotic*, (1997), 50(6), 514–521, XP002120210, p. 514, left–hand column, paragraph 1, p. 515, compound CP–111, 907.

Wakisaka, Yoshiharu Et Al.: "Hygromycin and ephihygromycin from a bacterium, Corynebacterium equi No. 2841"; *J. Antibiotic*, (1980), 33(7), 695–704, XP002120211, p. 695, paragraph 1, pp. 700–703, "Production and characterization of the products", p. 703, "Discussion".

*Chemical Abstracts*, vol. 80, No. 17, Apr. 29, 1974 (Apr. 29, 1974), Columbus, OH, US; abstract No. 94225, Polatovskaya, O.G. Et Al.: "Effect of age and amount of inoculation material on the rate of biosynthesis of Hygromycin V" XP002120212 abstract & TR., Lenigrad. Nauch.–Issled. Inst. Antibiot. (1972), No. 9, 82–3.

*Primary Examiner*—Elli Peselev
(74) *Attorney, Agent, or Firm*—Peter C. Richardson; Paul H. Ginsburg; Israel Nissenbaum

(57) ABSTRACT

This invention relates to compounds of the formula

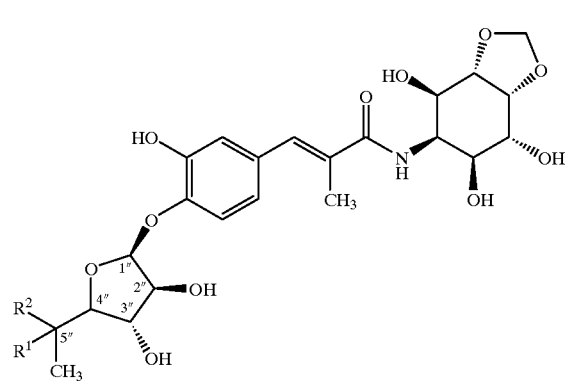

and to pharmaceutically acceptable salts, prodrugs and solvates thereof, wherein $R^1$ and $R^2$ are as defined herein. The compounds of formula 1 are antibacterial and antiprotozoal agents that may be used to treat various bacterial and protozoal infections and disorders related to such infections. The invention also relates to pharmaceutical compositions containing the compounds of formula 1 and to methods of treating bacterial and protozoal infections by administering the compounds of formula 1.

18 Claims, No Drawings

HYGROMYCIN DERIVATIVES

This application is a 371 of PCT/B99/00795 May 3, 1999 and claims benefit of provisional application Ser. No. 60/084,042 May 4, 1998.

BACKGROUND OF THE INVENTION

This invention relates to novel hygromycin A derivatives that are useful as antibacterial and antiprotozoal agents in mammals, including man, as well as in fish and birds. This invention also relates to pharmaceutical compositions containing the novel compounds and to methods of treating bacterial and protozoal infections in mammals, fish and birds by administering the novel compounds to mammals, fish and birds requiring such treatment.

Hygromycin A is a fermentation-derived natural product first isolated from *Streptomyces hygroscopicus* in 1953. As an antibiotic, hygromycin A possesses activity against human pathogens and is reported to possess potent in vitro activity against *Serpulina* (*Treponema*) *hyodysenteriae* which causes swine dysentery. Several references refer to semisynthetic modifications of hygromycin A, including the following: derivatization of the 5" ketone of hygromycin A to the 2,4-dinitrophenylhydrazone is referred to in K. Isono et al., *J. Antibiotics* 1957, 10, 21, and R. L. Mann and D. O. Woolf, *J. Amer Chem. Soc.* 1957, 79, 120. K. Isono et al., ibid., also refer to the thiosemicarbazone at 5"; reduction of the 5" ketone of hygromycin A to the 5" alcohol is referred to in R. L. Mann and D. O. Woolf, ibid., as well as in S. J. Hecker et al., *Bioorg. Med. Chem. Lett.* 1992, 2, 533 and S. J. Hecker et al., *Bioorg. Med. Chem. Lett.* 1993, 3, 295; furanose analogues are referred to in B. H. Jaynes et al., *Bioorg. Med. Chem. Lett.* 1993, 3, 1531, and B. H. Jaynes et al., *J. Antibiot.* 1992, 45, 1705; aromatic ring analogues are referred to in S. J. Hecker et al., *Bioorg. Med. Chem. Lett.* 1993, 3, 289, and C. B. Cooper et al., *Bioorg. Med. Chem. Lett.* 1997, 7, 1747; enamide analogues are referred to in S. J. Hecker et al., *Bioorg. Med. Chem. Lett.* 1992, 2, 533; aminocyclitol analogues are referred to in S. J. Hecker et al., *Bioorg. Med. Chem. Lett.* 1992, 2, 1015, and in S. J. Hecker et al., *Bioorg. Med. Chem. Lett.* 1992, 2, 1043. The hygromycin A derivatives of the present invention possess activity against both gram-negative and gram-positive bacteria and protozoa.

Filed concurrently with the present application, U.S. provisional patent application no. 60/084058, filed May 4, 1998, entitled "2'-Deoxy Hygromycin Derivatives", with named inventor R. G. Linde II, also refers to hygromycin analogues and is incorporated herein by reference in its entirety.

SUMMARY OF THE INVENTION

The present invention relates to compounds of the formula

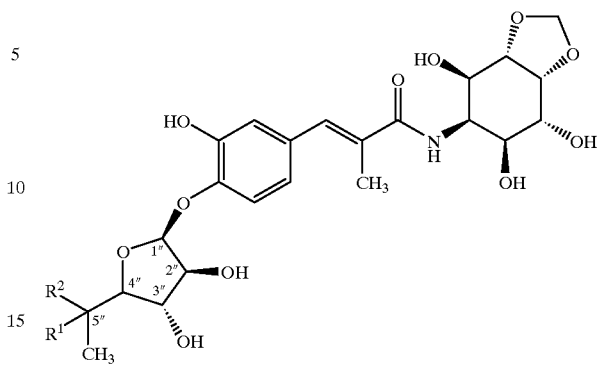

and to pharmaceutically acceptable salts, prodrugs and solvates thereof wherein:

$R^1$ is H and $R^2$ is —$NR^3R^4$, —$NR^4C(O)R^3$, —$OC(O)NR^3R^4$ or —$OR^3$;

or $R^1$ and $R^2$ are taken together to form =N—$OR^3$, =$CR^4R^3$, =$CR^4C(O)R^3$, =$CR^4C(O)OR^3$, or =$CR^4C(O)NR^3R^4$;

each $R^3$ is independently selected from H, $C_1$–$C_{10}$ alkyl, $C_2$–$C_{10}$ alkenyl, —$(CH_2)_t(C_3$–$C_{10}$ cycloalkyl), —$(CH_2)_t(C_6$–$C_{10}$ aryl), and —$(CH_2)_t$(4–10 membered heterocyclic), wherein t is an integer ranging from 0 to 5, said alkyl group optionally contains 1 or 2 hetero moieties selected from O, —$S(O)_j$— wherein j is an integer ranging from 0 to 2, and —$N(R^7)$— with the proviso that two O atoms, two S atoms, or an O and S atom are not attached directly to each other; said cycloalkyl, aryl and heterocyclic $R^3$ groups are optionally fused to a benzene ring, a $C_5$–$C_8$ saturated cyclic group, or a 4–10 membered heterocyclic group; the —$(CH_2)_t$— moieties of the foregoing $R^3$ groups optionally include a carbon-carbon double or triple bond where t is an integer between 2 and 5; and the foregoing $R^3$ groups, except H but including any optional fused rings referred to above, are optionally substituted by 1 to 5 $R^5$ groups, with the proviso that $R^3$ is not H, methyl or ethyl where $R^1$ is H and $R^2$ is —$OR^3$;

each $R^4$ is independently H or $C_1$–$C_{10}$ alkyl;

each $R^5$ is independently selected from $C_1$–$C_{10}$ alkyl, $C_3$–$C_{10}$ cycloalkyl, halo, cyano, nitro, trifluoromethyl, difluoromethoxy, trifluoromethoxy, azido, —$OR^6$, —$C(O)R^6$, —$C(O)OR^6$, —$NR^7C(O)OR^9$, —$OC(O)R^6$, —$NR^7SO_2R^9$, —$SO_2NR^6R^7$, —$NR^7C(O)R^6$, —$C(O)NR^6R^7$, —$NR^6R^7$, —$S(O)_j(CH_2)_m(C_6$–$C_{10}$ aryl), —$S(O)_j(C_1$–$C_6$ alkyl), wherein j is an integer ranging from 0 to 2, —$(CH_2)_m(C_6$–$C_{10}$ aryl), —$O(CH_2)_m(C_6$–$C_{10}$ aryl), —$NR^7(CH_2)_m(C_6$–$C_{10}$ aryl), and —$(CH_2)_m$(4–10 membered heterocyclic), wherein m is an integer ranging from 0 to 4; said alkyl group optionally contains 1 or 2 hetero moieties selected from O, —$S(O)_j$— wherein j is an integer ranging from 0 to 2, and —$N(R^7)$— with the proviso that two O atoms, two S atoms, or an O and S atom are not attached directly to each other; said cycloalkyl, aryl and heterocyclic $R^5$ groups are optionally fused to a $C_6$–$C_{10}$ aryl group, a $C_5$–$C_8$ saturated cyclic group, or a 4–10 membered heterocyclic group; and said alkyl, cycloalkyl, aryl and heterocyclic $R^5$ groups are optionally substituted by 1 to 5 substituents independently selected from halo, cyano, nitro, trifluoromethyl, difluoromethoxy, trifluoromethoxy, azido, —NR$^7$SO$_2$R$^9$, —SO$_2$NR$^6$R$^7$, —C(O)R$^6$, —C(O)OR$^6$, —OC(O)R$^6$, —NR$^7$C(O)OR$^9$, —NR$^7$C(O)R$^6$, —C(O)NR$^6$R$^7$, —NR$^6$R$^7$, —OR$^6$, C$_1$–C$_{10}$ alkyl, —(CH$_2$)$_m$(C$_6$–C$_{10}$ aryl), and —(CH$_2$)$_m$(4–10 membered heterocyclic), wherein m is an integer ranging from 0 to 4;

each R$^6$ is independently selected from H, C$_1$–C$_{10}$ alkyl, C$_3$–C$_{10}$ cycloalkyl, —(CH$_2$)$_m$(C$_6$–C$_{10}$ aryl), and —(CH$_2$)$_m$(4–10 membered heterocyclic), wherein m is an integer ranging from 0 to 4; said alkyl group optionally includes 1 or 2 hetero moieties selected from O, —S(O)$_j$— wherein j is an integer ranging from 0 to 2, and —N(R$^7$)— with the proviso that two O atoms, two S atoms, or an O and S atom are not attached directly to each other; said cycloalkyl, aryl and heterocyclic R$^6$ groups are optionally fused to a C$_6$–C$_{10}$ aryl group, a C$_5$–C$_8$ saturated cyclic group, or a 4–10 membered heterocyclic group; and the foregoing R$^6$ substituents, except H, are optionally substituted by 1 to 5 substituents independently selected from halo, cyano, nitro, trifluoromethyl, difluoromethoxy, trifluoromethoxy, azido, —C(O)R$^7$, —C(O)OR$^7$, —OC(O)R$^7$, —NR$^7$C(O)R$^8$, —C(O)NR$^7$R$^8$, —NR$^7$R$^8$, hydroxy, C$_1$–C$_6$ alkyl, and C$_1$–C$_6$ alkoxy;

each R$^7$ and R$^8$ is independently H or C$_1$–C$_6$ alkyl; and, R$^9$ is selected from the substituents provided in the definition of R$^6$ except H.

Preferred compounds of formula 1 include those wherein R$^1$ and R$^2$ are taken together to form =N—OR$^3$, and R$^3$ is C$_1$–C$_4$ alkyl, C$_2$–C$_4$ alkenyl, —(CH$_2$)$_t$(C$_6$–C$_{10}$ aryl) or —(CH$_2$)$_t$(4–10 membered heterocyclic), wherein t is an integer ranging from 0 to 3, the heterocyclic group is optionally fused to a benzene ring, the aryl group is optionally fused to a 5 or 6 membered heterocyclic group, and the foregoing R$^3$ groups, including said optionally fused moieties, are optionally substituted by 1 to 5 substituents independently selected from nitro, halo, C$_1$–C$_3$ alkoxy, C$_1$–C$_4$ alkyl, trifluoromethyl, acetamido, tert-butoxycarbonylamino, tert-butoxycarbonylaminomethyl, tert-butoxycarbonyl, —NR$^6$R$^7$, phenyl, cyclohexyl, carboxy, aminomethyl, difluoromethoxy, trifluoromethoxy, cyano, piperidinyl, morpholino, phenoxy, and phenylthio.

Other preferred compounds of formula 1 include those wherein R$^1$ and R$^2$ are taken together to form =N—OR$^3$, and R$^3$ is —(CH$_2$)$_t$(C$_6$–C$_{10}$ aryl) or —(CH$_2$)$_t$(4–10 membered heterocyclic), wherein t is an integer ranging from 0 to 3, the heterocyclic group is optionally fused to a benzene ring, the aryl group is optionally fused to a 5 or 6 membered heterocyclic group, and the foregoing R$^3$ groups, including said optionally fused moieties, are optionally substituted by 1 to 5 substituents independently selected from nitro, halo, C$_1$–C$_3$ alkoxy, C$_1$–C$_4$ alkyl, trifluoromethyl, acetamido, tert-butoxycarbonyl, tert-butoxycarbonylamino, —NR$^6$R$^7$, phenyl, cyclohexyl, carboxy, tert-butoxycarbonylaminomethyl, aminomethyl, difluoromethoxy, trifluoromethoxy, cyano, piperidinyl, morpholino, phenoxy, and phenylthio.

Other preferred compounds of formula 1 include those wherein R$^1$ is H, R$^2$ is —NR$^3$R$^4$, R$^4$ is H or methyl, and R$^3$ is —(CH$_2$)$_t$(C$_6$–C$_{10}$ aryl) or —(CH$_2$)$_t$(4–10 membered heterocyclic), wherein t is an integer ranging from 0 to 2, and the R$^3$ group is optionally substituted by 1 to 5 substituents independently selected from halo, C$_1$–C$_3$ alkoxy, C$_1$–C$_4$ alkyl, and trifluoromethyl.

Other preferred compounds of formula 1 include those wherein R$^1$ is H, R$^2$ is —NR$^4$C(O)R$^3$, R$^4$ is H, and R$^3$ is C$_3$–C$_6$ cycloalkyl, —(CH$_2$)$_t$(C$_6$–C$_{10}$ aryl) or —(CH$_2$)$_t$(4–10 membered heterocyclic), wherein t is an integer ranging from 0 to 2, the aryl group is optionally fused to a 5 or 6 membered heterocyclic group, the heterocyclic group is optionally fused to a benzene ring, and the foregoing R$^3$ groups, including said optionally fused moieties, are optionally substituted by 1 to 5 substituents independently selected from halo, C$_1$–C$_3$ alkoxy, C$_1$–C$_4$ alkyl, and trifluoromethyl.

Other preferred compounds of formula 1 include those wherein R$^1$ and R$^2$ are taken together to form =CR$^4$C(O)OR$^3$ or =CR$^4$C(O)NR$^3$R$^4$, R$^4$ is H, and R$^3$ is H, C$_1$–C$_6$ alkyl, C$_3$–C$_6$ cycloalkyl, —(CH$_2$)$_t$(4–10 membered heterocyclic), or —(CH$_2$)$_t$(C$_6$–C$_{10}$ aryl) wherein t is an integer ranging from 0 to 2, the aryl group is optionally fused to a 5 or 6 membered heterocyclic group, the heterocyclic group is optionally fused to a benzene ring, and the foregoing R$^3$ groups, except H but including said optionally fused moieties, are optionally substituted by 1 to 5 substituents independently selected from halo, C$_1$–C$_3$ alkoxy, C$_1$–C$_4$ alkyl, —NR$^6$R$^7$ and trifluoromethyl.

Other preferred compounds of formula 1 include those wherein R$^1$ is H, R$^2$ is —OR$^3$, and R$^3$ is C$_1$–C$_4$ alkyl, —(CH$_2$)$_t$(4–10 membered heterocyclic), or —(CH$_2$)$_t$(C$_6$–C$_{10}$ aryl) wherein t is an integer ranging from 1 to 2, the aryl group is optionally fused to a 5 or 6 membered heterocyclic group, the heterocyclic group is optionally fused to a benzene ring, and the foregoing R$^3$ groups, including said optionally fused moieties, are optionally substituted by 1 to 5 substituents independently selected from halo, C$_1$–C$_3$ alkoxy, C$_1$–C$_4$ alkyl, cyclohexyl, cyano, trifluoromethyl, benzyloxy and trifluoromethyl.

Other preferred compounds of formula 1 include those wherein R$^1$ is H, R$^2$ is —OC(O)NR$^3$R$^4$, R$^4$ is H, and R$^3$ is —(CH$_2$)$_t$(C$_5$–C$_{10}$ aryl) wherein t is an integer ranging from 0 to 2, and the R$^3$ group is optionally substituted by 1 to 5 substituents independently selected from halo, C$_1$–C$_3$ alkoxy, C$_1$–C$_4$ alkyl, and trifluoromethyl.

Specific preferred compounds of formula 1 include those selected from the group consisting of:

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(benzofuran-2-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(benzofuran-2-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-phenylmethyloxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-phenylmethyloxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-chlorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3,4-dichlorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3,4-dichlorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-pyridinyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-(4-morpholinyl)phenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[cyclohexylmethyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-fluorophenyl)methyl]oxime;

5-Deoxy-5-[[3-[4-[(6-deoxy-b-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,4-dichlorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3,4-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(furan-3-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(furan-3-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(1,3-benzodioxol-5-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(1,3-benzodioxol-5-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chlorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-cyclohexylphenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-aminophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[[(4-aminomethyl)phenyl]methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[3-(4-chlorophenyl)propyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[3-(4-chlorophenyl)propyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-(trifluoromethoxy)phenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-(1-piperidinyl)phenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[2-(phenylthio)ethyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(benzofuran-5-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(benzofuran-5-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2-phenylpyrimidin-5-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-fluoro-4-methoxyphenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3,4-dihydro-2H-1-benzopyran-4-yl)methyl]oxime;

5-Deoxy-5-[[3-[4-[(5,6-dideoxy-5-(methyl(phenylmethyl)amino-α-L-galacto-furanos-1-yl)oxy]-3-hydroxyphenyl]-2-methyl-1-oxo-2-(E)-propenyl]amino]-1,2-O-methylene-D-neo-inositol;

5-Deoxy-5-[[3-[4-[(5,6-dideoxy-5-phenylamino-α-L-galacto-furanos-1-yl)oxy]-3-hydroxyphenyl]-2-methyl-1-oxo-2-(E)-propenyl]amino]-1,2-O-methylene-D-neo-inositol;

5-Deoxy-5-[[3-[4-[(6-deoxy-5-O-[(3,4-dichlorophenyl)methyl]-β-D-altro-furanos-1-yl)oxy]-3-hydroxyphenyl]-2-methyl-1-oxo-2-(E)-propenyl]amino]-1,2-O-methylene-D-neo-inositol;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(furan-2-yl)methyl]oxime;

5-Deoxy-5-[[3-[4-[(5-methyl-β-D-arabino-hept-5-(E)-enofuranuron-1-ylic acid)oxy]-3-hydroxyphenyl]-2-methyl-1-oxo-2-(E)-propenyl]amino]-1,2-O-methylene-D-neo-inositol, ethyl ester;

5-Deoxy-5-[[3-[4-[[N-(furan-2-yl)methyl]-(5-methyl-β-D-arabino-hept-5-(E)-enofuranuron-1-yl-amide)oxy]-3-hydroxyphenyl]-2-methyl-1-oxo-2-(E)-propenyl]amino]-1,2-O-methylene-D-neo-inositol;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[3-(phenyl)propyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(2-propen-1-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(2-propen-1-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-methylphenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-methoxyphenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-(trifluoromethyl)phenyl)methyl]oxime;

5-Deoxy-5-[[3-[4-[(6-deoxy-5-O-[(4-chlorophenyl)methyl]-β-D-altro-furanos-1-yl)oxy]-3-hydroxyphenyl]-2-methyl-1-oxo-2-(E)-propenyl]amino]-1,2-O-methylene-D-neo-inositol;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[diphenylmethyl]oxime;

5-Deoxy-5-[[3-[4-[(6-deoxy-5-phenylcarbamate-β-D-altro-furanos-1-yl)oxy]-3-hydroxyphenyl]-2-methyl-1-oxo-2-(E)-propenyl]amino]-1,2-O-methylene-D-neo-inositol;

5-Deoxy-5-[[3-[4-[(6-deoxy-5-[(3,4-dichlorophenyl)methyl]carbamate-β-D-altro-furanos-1-yl)oxy]-3-hydroxyphenyl]-2-methyl-1-oxo-2-(E)-propenyl]amino]-1,2-O-methylene-D-neo-inositol;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chlorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chloro-2-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chloro-2-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chloro-4-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chloro-4-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chloro-5-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chloro-5-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(5-chloro-2-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(5-chloro-2-fluorophenyl)methyl]oxime;

5-Deoxy-5-[[3-[4-[(6-deoxy-β-D-arabin-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3,5-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3,5-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-chloro-3-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-chloro-3-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-chloro-1,3-benzodioxol-6-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-chloro-1,3-benzodioxol-6-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(5-chloro-1,3-benzodioxol-6-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(5-chloro-1,3-benzodioxol-6-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-chloro-1,3-benzodioxol-5-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-chloro-1,3-benzodioxol-5-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,3-dihydrobenzofuran-6-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,3-dihydrobenzofuran-6-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,3-dihydrobenzofuran-5-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,3-dihydrobenzofuran-5-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(1,2,3,4-tetrahydronaphthalen-1-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(1,2,3,4-tetrahydronaphthalen-1-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(7-chloro-1,2,3,4-tetrahydronaphthalen-1-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(7-chloro-1,2,3,4-tetrahydronaphthalen-1-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(7-fluoro-1,2,3,4-tetrahydronaphthalen-1-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(7-fluoro-1,2,3,4-tetrahydronaphthalen-1-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(8-chloro-3,4-dihydro-2H-1-benzopyran-4-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(8-chloro-3,4-dihydro-2H-1-benzopyran-4-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(6-chloro-3,4-dihydro-2H-1-benzopyran-4-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(6-chloro-3,4-dihydro-2H-1-benzopyran-4-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(8-fluoro-3,4-dihydro-2H-1-benzopyran-4-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(8-fluoro-3,4-dihydro-2H-1-benzopyran-4-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(6-fluoro-3,4-dihydro-2H-1-benzopyran-4-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(6-fluoro-3,4-dihydro-2H-1-benzopyran-4-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(quinolin-2-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(quinolin-2-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(quinolin-3-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(quinolin-3-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[4-(phenylmethyl)phenylmethyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[4-(phenylmethyl)phenylmethyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[4-(phenoxy)phenylmethyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[4-(phenoxy)phenylmethyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3,5-dichlorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3,5-dichlorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(phenyl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(phenyl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(3-chloro-4-fluorophenyl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(3-chloro-4-fluorophenyl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-chlorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3,4-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,4-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,4-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,1,3-benzoxadiazol-5-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,1,3-benzoxadiazol-5-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,3,5,6-tetrafluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,3,5,6-tetrafluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,3-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,3-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-phenyl-furan-3-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-phenyl-furan-3-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-phenyl-furan-2-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-phenyl-furan-2-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,3-difluoro-6-methoxyphenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,3-difluoro-6-methoxyphenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chloro-thiophen-2-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chloro-thiophen-2-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(5-chloro-thiophen-2-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(5-chloro-thiophen-2-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chloro-2,6-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chloro-2,6-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[1-(3-chlorophenyl)ethyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(3-difluoromethoxy-phenyl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(3-difluoromethoxy-phenyl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(4-difluoromethoxy-phenyl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(4-difluoromethoxy-phenyl)oxime;

and the pharmaceutically acceptable salts and solvates of said compounds.

In a more specific embodiment, the present invention includes the following compounds:

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(1,3-benzodioxol-5-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chlorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chlorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(benzofuran-2-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3,5-dichlorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3,5-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3,5-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chloro-2-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chloro-2-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chloro-4-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chloro-4-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-chloro-3-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-chloro-3-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-chlorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-chlorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-phenyl-furan-2-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chloro-5-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3,4-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3,4-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,3-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,4-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,4-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,3,5,6-tetrafluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(3-chloro-4-fluorophenyl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(3-chloro-4-fluorophenyl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(5-chloro-thiophen-2-yl)methyl]oxime;

and the pharmaceutically acceptable salts and solvates of said compounds.

The invention also relates to a pharmaceutical composition for the treatment of a disorder selected from a bacterial infection, a protozoal infection, and disorders related to bacterial infections or protozoal infections, in a mammal, fish, or bird which comprises a therapeutically effective amount of a compound of formula 1, or a pharmaceutically acceptable salt thereof, and a pharmaceutically acceptable carrier.

The invention also relates to a method of treating a disorder selected from a bacterial infection, a protozoal infection, and disorders related to bacterial infections or protozoal infections, in a mammal, fish, or bird which comprises administering to said mammal, fish or bird a therapeutically effective amount of a compound of formula 1 or a pharmaceutically acceptable salt thereof.

The invention also relates to a method of preparing a composition containing hygromycin A and epi-hygromycin, wherein the ratio of hygromycin A to epi-hygromycin is at least 10:1, which comprises fermenting *Streptomyces hygroscopicus* in media having a pH less than 6.9 at a temperature ranging from 25° C. to 35° C. In a preferred embodiment of said method said *Streptomyces hygroscopicus* is *Streptomyces hygroscopicus* NRRL2388 or a mutant thereof, said pH ranges from 6.2 to 6.7, said temperature is about 29° C., and the ratio of hygromycin A to epi-hygromycin is at least 14:1. In a further aspect of the above method, said composition is maintained at a pH of 6.0 to 6.4, preferably about 6.0, and the temperature of said composition is maintained at a temperature ranging from 25° C. to 35° C. during purification of said hygromycin A to an oil.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

As used herein, unless otherwise indicated, the terms or phrases "bacterial infection(s)", "protozoal infection(s)", and "disorders related to bacterial infections or protozoal infections" include the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus, Enterococcus faecalis, E. faecium, E. casselflavus, S. epidermidis, S. haemolyticus*, or Peptostreptococcus spp.; pharyngitis, rheumatic fever, and glomerulonephritis related to infection by *Streptococcus pyogenes*, Groups C and G streptococci, *Corynebacterium diphtheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; blood and tissue infections, including endocarditis and osteomyelitis, caused by *S. aureus, S. haemolyticus, E. faecalis, E. faecium, E. durans*, including strains resistant to known antibacterials such as, but not limited to, beta-lactams, vancomycin, aminoglycosides, quinolones, chloramphenicol, tetracylines and macrolides; uncomplicated skin and soft tissue infections and abscesses, and puerperal fever related to infection by *Staphylococcus aureus*, coagulase-negative staphylococci (i.e., *S. epidermidis, S. hemolyticus*, etc.), *Streptococcus pyogenes, Streptococcus agalactiae*, Streptococcal groups C–F (minute-colony streptococci), viridans streptococci, *Corynebacterium minutissimum*, Clostridium spp., or *Bartonella henselae*; uncomplicated acute urinary tract infections related to infection by *Staphylococcus aureus*, coagulase-negative staphylococcal species, or Enterococcus spp.; urethritis and cervicitis; sexually transmitted diseases related to infection by *Chlamydia trachomatis, Haemophilus ducreyi, Treponema pallidum, Ureaplasma urealyticum*, or *Neiserria gonorrheae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*, conjunctivitis, keratitis, and dacrocystitis related to infection by *Chlamydia trachomatis, Neisseria gonorrhoeae, S. aureus, S. pneumoniae, S. pyogenes, H. influenzae*, or Listeria spp.; disseminated *Mycobacterium avium* complex (MAC) disease related to infection by *Mycobacterium avium*, or *Mycobacterium intracellulare*; infections caused by *Mycobacterium tuberculosis, M. leprae, M. paratuberculosis, M. kansasii*, or *M. chelonei*; gastroenteritis related to infection by *Campylobacter jejuni*; intestinal protozoa related to infection by Cryptosporidium spp.; odontogenic infection related to infection by viridans streptococci; persistent cough related to infection by *Bordetella pertussis*; gas gangrene related to infection by *Clostridium perfringens* or Bacteroides spp.; and atherosclerosis or cardiovascular disease related to infection by *Helicobacter pylori* or *Chlamydia pneumoniae*. Bacterial infections and protozoal infections, and disorders related to such infections, which may be treated or prevented in animals include the following: bovine respiratory disease related to infection by *P. haemolytica, P. multocida, Mycoplasma bovis*, or Bordetella spp.; cow enteric disease related to infection by protozoa (i.e., coccidia, cryptosporidia, etc.); dairy cow mastitis related to infection by *S. aureus, Strep. uberis, Streptococcus agalactiae, Streptococcus dysgalactiae*, Corynebacterium, or Enterococcus spp.; swine respiratory disease related to infection by *A. pleuro., P. multocida*, or Mycoplasma spp.; swine enteric disease related to infection by *Lawsonia intracellularis*, Salmonella, or *Serpulina hyodysinteriae*; cow footrot related to infection by Fusobacterium spp.; cow hairy warts related to infection by *Fusobacterium necrophorum* or *Bacteroides nodosus*; cow pink-eye related to infection by *Moraxella bovis*; cow premature abortion related to infection by protozoa (i.e. neosporium); skin and soft tissue infections in dogs and cats related to infection by *S. epidermidis, S. intermedius*, coagulase neg. *Staphylococcus* or *P. multocida*; and dental or mouth infections in dogs and cats related to infection by Alcaligenes spp., Bacteroides spp., Clostridium spp., Enterobacter spp., Eubacterium, Peptostreptococcus, Porphyromonas, or Prevotella. Other bacterial infections and protozoal infections, and disorders related to such infections, which may be treated or prevented in accord with the method of the present invention are referred to in J. P. Sanford et al., "The Sanford Guide To Antimicrobial Therapy," 26th Edition, (Antimicrobial Therapy, Inc., 1996).

The term "halo", as used herein, unless otherwise indicated, includes fluoro, chloro, bromo or iodo. Preferred halo groups are fluoro, chloro and bromo.

The term "alkyl", as used herein, unless otherwise indicated, includes saturated monovalent hydrocarbon radicals having straight or branched moieties. Said alkyl group may include one or two double or triple bonds. It is understood that for said alkyl group to include a carbon-carbon double or triple bond at least two carbon atoms are required in said alkyl group.

The term "aryl", as used herein, unless otherwise indicated, includes an organic radical derived from an aromatic hydrocarbon by removal of one hydrogen, such as phenyl or naphthyl.

The term "4–10 membered heterocyclic", as used herein, unless otherwise indicated, includes aromatic and non-aromatic heterocyclic groups containing one or more heteroatoms each selected from O, S and N, wherein each heterocyclic group has from 4–10 atoms in its ring system. Non-aromatic heterocyclic groups include groups having only 4 atoms in their ring system, but aromatic heterocyclic groups must have at least 5 atoms in their ring system. The heterocyclic groups include benzo-fused ring systems and ring systems substituted with one or more oxo moieties. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

The phrase "pharmaceutically acceptable salt(s)", as used herein, unless otherwise indicated, includes salts of acidic or basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds of the present invention that include a basic moiety, such as an amino group, may form pharmaceutically acceptable salts with various amino acids, in addition to the acids mentioned above.

Those compounds of the present invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the present invention.

The compounds of the present invention have asymmetric centers and therefore exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them. In this regard, the invention includes both the E and Z configurations of the —OR$^3$ group connected to the nitrogen where R$^1$ and R$^2$ are taken together as an oxime moiety of the formula =N—OR$^3$. The compounds of formula 1 may also exist as tautomers. This invention relates to the use of all such tautomers and mixtures thereof.

The subject invention also includes isotopically-labelled compounds, and the pharmaceutically acceptable salts thereof, which are identical to those recited in Formula 1, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of Formula 1 of this invention and prodrugs thereof can generally be prepared by carrying out the procedures disclosed in the Schemes and/or in the Examples and Preparations below, by substituting a readily available isotopically labelled reagent for a non-isotopically labelled reagent.

This invention also encompasses pharmaceutical compositions containing and methods of treating bacterial infections through administering prodrugs of compounds of the formula 1. Compounds of formula 1 having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula 1. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs are also encompassed. For instance, free carboxyl groups can be derivatized as amides or alkyl esters. The amide and ester moieties may incorporate groups including but not limited to ether, amine and carboxylic acid functionalities. Free hydroxy groups may be derivatized using groups including but not limited to hemisuccinates, phosphate esters, dimethylaminoacetates, and phosphoryloxymethyloxycarbonyls, as outlined in D. Fleisher, R. Bong, B. H. Stewart, Advanced Drug Delivery Reviews (1996) 19, 115. Carbamate prodrugs of hydroxy and amino groups are also included, as are carbonate prodrugs and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in R. P. Robinson et al., J. Medicinal Chemistry (1996) 39, 10.

Selective introduction of prodrug side chains can be carried out on the hydroxy groups of the hygromycin A core molecule. For instance, exhaustive silylation of the six hydroxy groups of hygromycin A can be carried out, for instance with tert-butyl dimethylsilyl chloride. Subjection of the hexasilyl derivative to the action of potassium carbonate in methanol at room temperature selectively removes the phenolic silyl group, allowing further selective modification at that position. In another example, incomplete silylation of hygromycin A (see PC 10186, R. Linde, 2"-deoxy hygromycin A derivatives, U.S. provisional patent application No. 60/084,058, filed May 4, 1998) provides the pentasilyl derivative in which the C-2" hydroxy group is free. Selective acylation, alkylation, etc. can be carried out on this derivative to provide prodrug attachment at C-2".

DETAILED DESCRIPTION OF THE INVENTION

The preparation of the compounds of the present invention is illustrated in the following Scheme.

Scheme

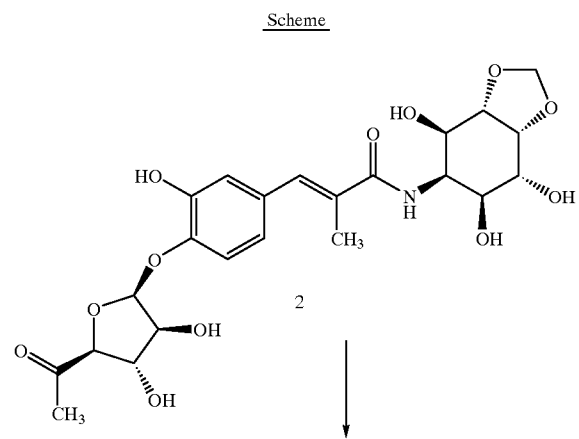

-continued

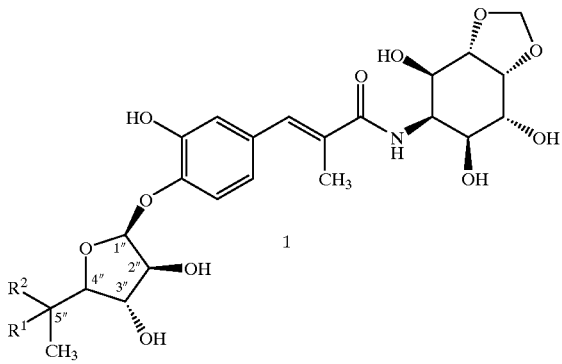

1

The compounds of the present invention are readily prepared. With reference to the Scheme illustrated above, the starting compound of formula 2 is hygromycin A which may be prepared according to procedures known to those skilled in the art, such as by fermentation of *Streptomyces hygroscopicus* NRRL 2388. The methyl ketone at 4" on the furanose sugar of the hygromycin A molecule can exist in the S configuration (hygromycin A) or R configuration (epi-hygromycin) on the furanose sugar. When published protocols are used as a model for fermentation and recovery of hygromycin A (U.S. Pat. No. 3,100,176; Antibiotic Chemotherapy (1953)3:1268–1278, 1279–1282), the hygromycin product is an approximately 3:1 mixture of hygromycin A (the 4"-(S) epimer), with the beta-oriented methyl ketone on the furanose sugar, as drawn, and epi-hygromycin. It is known in the literature (Journal of Antibiotics 33(7), 695–704, 1980) that pure hygromycin A will convert to epi-hygromycin in alkaline solutions. By carefully controlling the pH below 6.9 during the fermentation, and the pH, temperature and solvent exposure during the purification process, the final recovered product may be improved to at least a 14:1 ratio of hygromycin A: epi-hygromycin. Using this material, substantially single isomers derived from the 4"-(S) hygromycin may be prepared for use as templates for further synthetic modification.

Hygromycin A enriched for the 4"-(S) epimer is produced by fermentation of *Streptomyces hygroscopicus* NRRL2388, or mutants thereof, in media with pH controlled at less than 6.9, preferably 6.2 to 6.7, throughout the process. The medium contains assimilable sources of carbon, nitrogen and trace elements, as known to those skilled in the art. The fermentation is run at a temperature of about 25–35° C., preferably about 29° C. The fermentation is monitored, for example by high pressure liquid chromatography. Incubation is continued until the yield of the compound reaches a maximum, generally for a period of about 3 to 10 days, preferably about 4 to 6 days.

The formation of epi-hygromycin is minimized during the purification process by using an aqueous buffer (rather than unbuffered water) and controlling the pH of the active streams to near 6.0. Epi-hygromycin formation is also minimized by minimizing the time the recovered material is subject to higher temperatures. Thus, where it is necessary to reduce solvent concentrations, it is preferred to dilute active streams with the aqueous buffer and avoid use of rotary evaporation at elevated temperatures. Also, as means of avoiding higher temperatures, a resin column may be used to concentrate the active solution prior to the final purification step in order to reduce the volume of solution that must be boiled. The final purification step in the process is the concentration of the active cuts to solids using vacuum and a bath temperature of about 35–50° C. The period in which the solution is subject to elevated temperatures may be minimized by boiling in stages.

The compounds of formula 1 wherein $R^1$ and $R^2$ are taken together to form an oxime of the formula $=NOR^3$, wherein $R^3$ is as defined above, may be prepared by treating hygromycin A (the compound of formula 2) with a hydroxylamine of the formula $R^3ONH_2$, using the free base or salt of the hydroxylamine, preferably the free base of the hydroxylamine. The reaction is carried out in an inert solvent, such as methanol, ethanol or pyridine, with addition of base, such as $Na_2CO_3$ or $K_2CO_3$, if the salt, for instance the HCl salt, of the hydroxylamine is used, at a temperature ranging from about 0° C. to 65° C., preferably from 0° C. to 25° C. The hydroxylamine of formula $R^3ONH_2$ may be prepared using one or more procedures disclosed in Bioconjugate Chemistry (1990), 2, 96; Journal of Pharmaceutical Science (1969) 58, 138; and Chem. Pharm. Bull (1967) 15, 345.

The compounds of formula 1 wherein $R^1$ is H and $R^2$ is —$NR^3R^4$, wherein $R^3$ and $R^4$ are as defined above, can be synthesized by reductive amination at the C-5" ketone site of hygromycin A. Combination of $R^4NH_2$ and hygromycin A in an inert solvent and treatment with a reducing agent such as $NaBH_4$, $NaBH(OAc)_3$ (Ac is acetyl), or $NaCNBH_3$ provides the product with $R^3$=H. To convert $R^3$ to a group other than H, a second reductive amination can be carried out with an appropriate aldehyde or ketone of the formula RC(O)H or RC(O)R' (where $R^3$ is $RCH_2$— or RR'CH—, and R' and R are any of the moieties in the definition of $R^3$ that may be attached through a methylene group such as an alkyl, arylalkyl, or heterocyclicalkyl group). An Eschweiler-Clark reaction may be used to introduce a methyl group as the $R^3$ substituent. To provide an amide group, such as where $R^1$ is H and $R^2$ is —$NR^4C(O)R^3$, an amine of the formula —$NHR^4$ may be introduced as described above and then an acyl moiety of the formula —$C(O)R^3$ may be introduced by treating the intermediate with an activated form of the carboxylic acid, such as $R^3COCl$ or $R^3C(O)OC(O)R^3$, or by using an amide coupling agent such as (2-ethoxy-1-ethoxycarbonyl-1,2-dihydroquinoline (EEDQ), 1,1'-carbonyl-diimidazole (CDI), or a carbodiimide such as 1,3-dicyclohexylcarbodiimide (DCC). During the above procedures, any of the hydroxyl groups of hygromycin A that are esterified can be liberated in a final deprotection step using $K_2CO_3$ in methanol.

Compounds of formula 1 where $R^1$ is H and $R^2$ is —$NR^4C(O)R^3$, wherein $R^4$ is H and $R^3$ is as defined above, may be prepared through use of the primary amine derived from reductive amination of hygromycin A with an ammonia equivalent, for instance through the use of ammonium acetate and sodium cyanoborohydride or sodium triacetoxyborohydride. Alternatively, this primary amine can be prepared via the corresponding azide: 1) the hydroxy groups of hygromycin A can be protected, for instance as their TBDMS (tert-butyldimethylsilyl) derivatives, for instance through the action of TBDMSCl and an amine base such as imidazole or pyridine; (2) the C-5" ketone of hygromycin A is then reduced, for instance with sodium borohydride in methanol, to give persilylated 5"-hydroxy hygromycin; 3) the resulting alcohol is transformed into the mesylate, for instance through the action of methanesulfonyl chloride and triethylamine; 4) the mesylate is displaced by azide, for example using sodium azide in N,N-dimethylformamide (DMF); and 5) the azide is reduced to the primary amine using for instance triphenylphosphine followed by aqueous hydrolysis.

Reaction of the primary amine with an activated form of $R^3C(O)OH$, for instance $R^3C(O)Cl$ or $R^3C(O)OC(O)R^3$, provides the corresponding amide. Alternatively, amide coupling reagents can be used with $R^3C(O)OH$, such as 1-(3-dimethylaminopropyl)-3-ethylcarbodiimide (EDC), diethyl phosphoryl cyanide (DEPC), DCC, CDI or EEDQ. Finally, any protecting groups are removed using an acid, such as acetic acid, hydrogen fluoride, hydrogen fluoride-pyridine complex, or fluoride ion, such as tetrabutylammonium fluoride (TBAF).

To incorporate an $R^4$ group other than H, the amide referred to above may be alkylated after protecting any free hydroxyl groups, for instance as silyl ethers. The alkylation may be carried out with a base and an alkylating agent, such as sodium hydride and an appropriate bromide of the formula $R^4$—Br. Deprotection of the hydroxyl groups is then carried out with an acid, such as acetic acid, hydrogen fluoride, hydrogen fluoride-pyridine complex, or fluoride ion, such as TBAF.

Alternatively, a reductive amination can be carried out on hygromycin A, or a protected version thereof, with $R^4NH_2$, mediated by sodium triacetoxyborohydride or sodium cyanoborohydride. The resulting secondary amine can be acylated as described above, with an activated form of $R^3C(O)OH$, or reacted with $R^3C(O)OH$ using an amide coupling reagent. Deprotection of the hydroxyl groups is then effected as described above.

Compounds of formula 1 where $R^1$ is H and $R^2$ is —OC(O)NR$^3$R$^4$ may be prepared by reacting persilylated 5"-hydroxy hygromycin A with isocyanate $R^3$NCO in toluene at temperatures from 40° C. to 110° C., preferably 50–80° C. Addition of dimethylaminopyridine and triethylamine to the reaction may be advantageous. The product of this reaction, which has $R^4$ equal to H, may be alkylated to give $R^4$ equal to $C_1$–$C_{10}$ alkyl through use of a base such as sodium hydride and an alkylating agent such as a bromide of the formula $R^4$—Br. Deprotection of the hydroxyl groups can then be carried out by use of an acid such as acetic acid, hydrogen fluoride, hydrogen fluoride-pyridine complex, or fluoride ion, such as TBAF.

Compounds of formula 1 where $R^1$ is H and $R^2$ is —OR$^3$, wherein $R^3$ is an alkyl group or a substituted alkyl group, may be prepared by alkylation of the corresponding alcohol of hygromycin A. In this process, the hydroxy groups of hygromycin A are appropriately protected, for instance as their silyl ethers using an appropriate reagent such as triethylsilyl chloride (TESCl), trimethylsilyl chloride (TMSCl) or TBDMS and an amine base, such as imidazole or pyridine. The C-5" ketone moiety is then reduced using an appropriate reducing agent such as sodium borohydride in methanol. The resulting alcohol can then be alkylated with $R^3$—X, wherein X is a leaving group such as Cl, Br or methanesulfonate, in the presence of a base, such as sodium hydride or potassium tert-butoxide. The protecting groups are then removed with acid, such as acetic acid, hydrogen fluoride, hydrogen fluoride-pyridine complex, or a fluoride source, such as TBAF.

Compounds of formula 1 where $R^1$ is H and $R^2$ is —OR$^3$, wherein $R^3$ is an aromatic or heterocyclic moiety, may be prepared via a Mitsunobu reaction. The protected hygromycin alcohol, prepared as described above, is subjected to a Mitsunobu reaction with $R^3$OH, mediated by triphenylphosphine and diethyl azodicarboxylate as described in D. L. Hughes, Org. Reactions (1992) 42 335. The resulting ether is then deprotected as described above.

Alternatively, when $R^1$ is H and $R^2$ is —OR$^3$, wherein $R^3$ is an aromatic or heterocyclic moiety, the protected hygromycin alcohol can be transformed into a leaving group, for instance the bromide or mesylate derivative. The leaving group can then be displaced by $R^3$OH using a base such as sodium hydride, potassium tert-butoxide or potassium carbonate.

Compounds of formula 1 wherein $R^1$ and $R^2$ are taken together to form =CR$^4$C(O)R$^3$, =CR$^4$C(O)OR$^3$, or =CR$^4$C(O)NR$^3$R$^4$, wherein $R^3$ and $R^4$ are as defined above, may be prepared through the corresponding α,β-unsaturated ester intermediates derived from Wittig or Horner-Emmons Wittig olefination of the C-5" ketone of hygromycin A. For instance, (carbethoxymethylene)triphenylphosphorane or (carbethoxyethylidene)triphenylphosphorane can be reacted with hygromycin A to provide the unsaturated ethyl ester. Hydrolysis of this ester, for instance with aqueous sodium hydroxide, provides the corresponding carboxylic acid ($R^1$ and $R^2$ taken together to form =CHC(O)OH). At this point, the hydroxyl groups of hygromycin can be protected, for instance as their TES or TBDMS ethers as described above. To prepare the esters described above, this carboxylic acid can be esterified with $R^3$OH, for instance through the action of DCC and DMAP, or CDI and a catalytic base such as sodium ethoxide.

Compounds of formula 1 wherein $R^1$ and $R^2$ are taken together to form =CR$^4$C(O)NR$^3$R$^4$ may be formed by treating the above carboxylic acid intermediate ($R^1$ and $R^2$ taken together to form =CHC(O)OH) with an amine of the formula $R^3NH_2$ with the use of an amide coupling agent such as DCC, CDI, EEDQ, DEPC, or EDC. On the protected derivative, $R^4$ can be introduced via alkylation, for instance with a base such as sodium hydride or potassium tert-butoxide and an alkylating agent such as $R^4$—X where is X is Br, Cl or methanesulfonate.

The compound of formula 1 ($R^1$ and $R^2$ are taken together to form =CR$^4$C(O)R$^3$) can be prepared either by direct Wittig or Horner-Emmons reaction of hygromycin A or a protected form of hygromycin A with for example the corresponding $R^3$C(O)CHR$^4$—PPh$_3$ (Ph is phenyl) or $R^3$C(O)CHR$^4$—P=O(OEt)$_2$ (Et is ethyl) reagent. Olefination can be carried out by procedures described in J. Boutagy and R. Thomas, Chem. Rev. (1974) 74, 87 and B. E. Maryanoff et al., Chem. Rev. (1989) 89 863. Alternatively, the protected, unsaturated carboxylic acid derivative of hygromycin A can be transformed into its Weinreb amide, for instance through treatment with CDI and N,O-dimethylhydroxylamine. This amide can then be reacted with $R^3$—M, where M is a metal ion such as Li or MgBr, to generate the ketone, according to the procedure of S. Nahm and S. M. Weinreb, Tet. Lett. (1981) 22 39.

Compounds of formula 1 wherein $R^1$ and $R^2$ are taken together to form =CR$^4$R$^3$, wherein $R^3$ and $R^4$ are as defined above, may be prepared by a Wittig or Horner-Emmons reaction of the ylid of $R^4$—CH(PPh$_3$)—R$^3$ or $R^4$—CH(P=O(OEt)$_2$)—R$^3$ with hygromycin A, or a protected derivative thereof, in which the hydroxyl groups have been modified as, for example, their silyl ethers such as TES or TBDMS as described above. The protecting groups can then be removed as described above.

Alternatively, the C-5" homologated ketone or aldehyde of hygromycin A can be utilized as an intermediate. These compounds can be accessed via Wittig or Horner-Emmons reaction with an oxygenated triphenylphosphonium salt or phosphorane such as Ph$_3$P—C(R$^3$)OMe (Me is methyl). The resulting enol ether can be hydrolyzed with mild acid, such as acetic acid or dilute HCl, to provide the aldehyde or ketone. The aldehyde or ketone can then be reacted with an organometallic derivative $R^4$M, where M is, for example, Li or MgBr, to provide the corresponding alcohol, which can be dehydrated under the action of methanesulfonyl chloride to provide the corresponding olefin. Deprotection as described above then provides the compound of formula 1 wherein $R^1$ and $R^2$ are taken together to form $=CR^4R^3$.

The compound of formula 1 wherein $R^1$ and $R^2$ are taken together to form $=CR^4R^3$ and $R^4$ is aryl or heteroaryl and $R^3$ does not equal hydrogen, may be prepared using a palladium-catalyzed process. Conversion of the protected ketone $CH_3$—$CH(COR^3)$-hygro to the enol triflate can be carried out by the method of P. J. Stang and W. Treptow, Synthesis (1980) 283. The enol triflate can then be coupled in a Suzuki or Stille-type palladium-catalyzed process with aryl or heteroaryl boronic acids $R^4B(OH)_2$ or aryl tin species, for example $R^4SnMe_3$ or $R^4SnBu_3$ to provide the unsaturated aryl derivatives. Suzuki coupling reactions can be carried out as described by N. Miyaura and A. Suzuki, Chem. Rev. (1995) 95 2457. Stille reactions are performed using conditions described in V. Farina et al., Org. Reactions (1997) 50 1. Deprotection as described above then provides the final compound.

The compounds of the present invention have asymmetric carbon atoms. Compounds having a mixture of isomers at one or more centers will exist as diastereomeric mixtures, which can be separated into their individual diastereomers on the basis of their physical chemical differences by methods known to those skilled in the art, for example, by chromatography or fractional crystallization. All such isomers, including diastereomer mixtures, are considered as part of the invention.

The compounds of the present invention that are basic in nature are capable of forming a wide variety of different salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the basic compounds of this invention are readily prepared by treating the basic compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of the present invention that are acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium, calcium and magnesium, etc. These salts can easily be prepared by treating the corresponding acidic compounds with an aqueous solution containing the desired alkali metal alkoxide or metal hydroxide, and then evaporating the resulting solution to dryness, preferably under reduced pressure. Alternatively, they may also be prepared by mixing lower alkanolic solutions of the acidic compounds and the desired alkali metal alkoxide or metal hydroxide together, and then evaporating the resulting solution to dryness in the same manner as before. In either case, stoichiometric quantities of reagents are preferably employed in order to ensure completeness of reaction and maximum yields of the desired final product.

The antibacterial activity of the compounds of the present invention against bacterial pathogens is demonstrated by the compound's ability to inhibit growth of defined strains of pathogens.

Assay

The assay, described below, employs conventional methodology and interpretation criteria and is designed to provide direction for chemical modifications that may lead to compounds with antibacterial activity against susceptible and drug-resistant organisms including, but not limited to, beta-lactam, macrolide and vancomycin resistance. In the assay, a panel of bacterial strains is assembled to include a variety of target pathogenic species, including representatives of antibiotic resistant bacteria. Use of this panel enables the chemical structure/activity relationship to be determined with respect to potency and spectrum of activity. The assay is performed in microtiter trays and interpreted according to *Performance Standards for Antimicrobial Disk Susceptibility Tests—Sixth Edition; Approved Standard*, published by The National Committee for Clinical Laboratory Standards (NCCLS) guidelines; the minimum inhibitory concentration (MIC) is used to compare strains. Compounds are initially dissolved in dimethylsulfoxide (DMSO) as stock solutions.

The activity of the compounds of the present invention also may be assessed in accord with Steers replicator technique which is a standard in vitro bacterial testing method described by Steers et al., *Antibiotics and Chemotherapy* 1959, 9, 307.

The in vivo activity of the compounds of the present invention can be determined by conventional animal protection studies well known to those skilled in the art, usually carried out in rodents.

According to one in vivo model, compounds are evaluated for efficacy in mouse models of acute bacterial infection. An example of one such in vivo system is provided as follows. Mice (CF1 mixed sex mice; 18–20 g) are allotted to cages upon their arrival, and allowed to acclimate 1–2 days before being placed in a study. The acute infection is produced by intraperitoneal inoculation of bacteria (*Staphylococcus aureus* strain 01A1095) suspended in 5% sterile hog gastric mucin. The inoculum is prepared by: growing the culture overnight at 37° C. on blood agar, harvesting the resulting surface growth with sterile brain heart infusion broth, and adjusting this suspension to a turbidity that when diluted 1:10 into 5% sterile hog gastric mucin would produce 100% lethality.

Mice (10 per group) are treated subcutaneously, at 0.5 hour and 4 hours after challenge. Appropriate non-treated (infected but not treated) and positive (vancomycin or minocycline, etc.) controls are included in each study. Percent survival is recorded after a 4-day observation period; the $PD_{50}$ (mg/kg/dose calculated to protect 50% of infected animals) is determined by the probit method.

The compounds of the present invention, and the pharmaceutically acceptable salts thereof (hereinafter "the active compounds"), may be administered through oral, parenteral, topical, or rectal routes in the treatment of bacterial and protozoal infections. In general, these compounds are most desirably administered in dosages ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. However, a dosage level that is in the range of about 3 mg/kg/day to about 60 mg/kg/day is most desirably employed. Variations may nevertheless occur depending upon the species of mammal, fish or bird being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound in either sesame or peanut oil or in aqueous ethanol or propylene glycol may be employed. Use of a cyclodextrin derivative such as β-cyclodextrin sulfobutyl ether, sodium salt (see U.S. Pat. No. 5,134,127) may also be advantageous. The aqueous solutions should be suitably buffered if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques known to those skilled in the art.

Additionally, it is also possible to administer the active compounds of the present invention topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition.

The active compounds may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active compounds may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoyl residues. Furthermore, the active compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

The present invention is further described and exemplified in the preparations and examples described below. In the preparations and examples, "rt" means room or ambient temperature which is a temperature within the range of about 20–25° C.

PREPARATION 1

Five (5) mL of a frozen lot (stored at −80° C. in 20% glycerol/80% inoculum medium) of the culture *Streptomyces hygroscopicus* NRRL 2388 was used to inoculate 1 L of hygromycin inoculum medium (Corn Products Corp. cerelose 13 g/L, Hubinger starch 7 g/L, Roquette corn steep solids 3 g/L, Sheffield Brand Products NZ Amine YTT 7 g/L, Baker $CoCl_2.6H_2O$ 0.002 g/L, $KH_2PO_4$ 0.7 g/L, $MgSO_4.7H_2O$ 1.3 g/L, ammonium sulfate 0.7 g/L, Dow Chemical P2000 defoamer 1 drop/flask, Colfax soybean oil 2 drops/flask, pH to 7.0 before autoclave) in a 2.8 L Fernbach flask. The culture was grown for 3 days at 29° C. with 200 rpm agitation on a 2-inch-throw shaker. This grown culture was used to inoculate 8 L of sterile hygromycin fermentation medium (Albaglos calcium carbonate 1 g/L, Sheffield Brand Products NZ Amine YTT 5 g/L, Hubinger's starch 20 g/L, Archer Daniels Midland Nutrisoy flour 10 g/L, Dow Chemical P2000 defoamer 1 ml/L, Baker $CoCl_2.6H_2O$ 0.002 g/L, Colfax soybean oil 2 ml/L, cerelose 10 g/L, NaCl 5 g/L, pH to 7.0 before autoclave) in a 14 liter fermentor jar (New Brunswick Microferm, New Brunswick, N.J.) equipped with two 4.75-inch Rushton impellers, spaced 3.75 inches from each other. The broth was incubated at 29° C. with an aeration rate of 8 L/minute, and with stirring at 800 rpm. To minimize formation of epihygromycin, the pH was maintained between 6.5 and 6.9 for 126 hours, then to 6.2 to 6.6 with $H_2SO_4$ (15%) for the rest of the run. The fermentation was harvested after 143 hours total incubation. At this time, the ratio was 31:1 hygromycin A to epi-hygromycin.

Six liters of broth from the above fermentation was centrifuged at 8000 rpm for approximately 15 minutes. After centrifugation, the pellet was discarded and the supernatant (at pH 6.4, assayed by HPLC to contain approximately 4.12 gms of hygromycin A activity) was loaded on a column packed with 500 gms of an XAD-16 resin (Rohm and Haas (Philadelphia, Pa.). The resin had previously been equilibrated with two bed volumes of 25 mM disodium phosphate, pH 6.0 ("buffer"). After loading, the column was washed with 2 bed volumes of buffer and 2 bed volumes of 80/20 buffer/methanol and the activity eluted with 5 bed volumes of 50/50 buffer/methanol. The cuts were assayed by HPLC and the cuts containing the bulk of the activity (2.730 gms of hygromycin A) were combined.

A part of this XAD-16 eluate (approximately 800 mg of hygromycin A) was diluted to 10% methanol by the addition of 1.8 liters of buffer and loaded on a 100 ml CG-161 column (TosoHaas (Montgomeryville, Pa.)) which had been equilibrated with 4 bed volumes of 90/10 buffer/methanol. The product was eluted with 6 bed volumes of 50/50 buffer/methanol. The cuts were assayed by HPLC and the active cuts were combined. The combined cut was evaporated to dryness and the solids assayed to be approximately 65% pure by weight. A small part of these solids were transferred for assay.

About 500 mg of the solids were mixed with 500 ml of water and 500 ml of ethyl acetate and stirred for 20 minutes. The two layers were separated and part of the aqueous layer was dried to obtain solids which were assayed to be approximately 52% purity by weight. Both these solids (#34945-280-1 and 281-1) were assayed by NMR and TLC and found to contain hygromycin A activity. In addition, the NMR showed a hygromycin A/epi-hygromycin ratio of approximately 15:1.

PREPARATION 2

Five (5) mL of a frozen lot (stored at −80° C. in 20% glycerol/80% inoculum medium) of the culture *Streptomyces hygroscopicus* NRRL 2388 was used to inoculate 1 L of Hygromycin inoculum medium (CPC International Inc. cerelose 13 g/L, Hubinger's starch 7 g/L, Roquette corn steep solids 3 g/L, NZ Amine YTT 7 g/L, Baker $CoCl_2.6H_2O$ 0.002 g/L, $KH_2PO_4$ 0.7 g/L, $MgSO_4.7H_2O$ 1.3 g/L, ammonium sulfate 0.7 g/L, Dow Chemical P2000 defoamer 1 drop/flask, Colfax soybean oil 2 drops/flask, pH to 7.0 before autoclave) in a 2.8 L Fernbach flask. The culture was grown for 2 to 3 days at 29° C. with 200 rpm agitation on a 2-inch-throw shaker. Two five-hundred gallon, stainless steel fermentors were loaded with 380–400 gallons of the hygromycin fermentation medium (Mineral Technologies Calcium Carbonate 1 g/L, Sheffield Brand Products NZ Amine YTT 5 g/L, Hubinger's starch 20 g/L, Archer Daniels Midland Co., Soyflour 10 g/L, Dow Chemical P2000 defoamer 1 ml/L, Baker $COCl_2.6H_2O$ 0.002 g/L, Colfax, Inc. soybean oil 2 gm/L, CPC International Inc. Cerelose 10 g/L, Cargill Inc. NaCl 5 g/L,). The medium was sterilized with 20 psig of steam for 60 minutes in the fermentors. After the medium was cooled using cooling coils in the fermentors, the pH was adjusted to 6.5–6.7. The fermentor conditions were set so that the airflow rate was 20 standard cubic feet per minute, the temperature was 28° C., the vent pressure was 5 psig, and the pH was maintained between 6.5–6.7 with 25% sodium hydroxide and 98% sulfuric acid. The agitation rates in the two fermentors were varied so as to maintain a dissolved oxygen level of greater than 20% of saturation level as measured in the broth immediately prior to inoculation. Upon setting the fermentor control conditions, five Fernbach inoculum flasks were combined in a sterile manner, into an 8 L aspirator bottle. This inoculum was then used for inoculation of a single, nominal, five-hundred gallon fermentor as described above. This procedure was repeated using 4 liters of inoculum so that one fermentor received four liters of inoculum and one fermenter received five liters of inoculum. Each fermentor ran for approximately 114 hours, at which time the fermentations were stopped. The broth pH was adjusted to 6.3 using 98% sulfuric acid and transferred from the fermentors for recovery.

The two fermentors referred to above (pH=6.3, having a ratio of hygromycin A to epi-hygromycin of approximately 51:1) were filtered on a ceramic filtration system. The filtrate (1450 gmsA, 506 gal) was loaded on a 70-gallon XAD-16 resin column. This column had been equilibrated previously with 4 bed volumes of a solution of trisodium phosphate buffer at pH 6.0 ("buffer"). After loading, the column was washed with 2 bed volumes of buffer and 2 bed volumes of 80/20 buffer/methanol. The activity was subsequently eluted from the column with 10 cuts (approximately 50 gallons each) of a solution of 50/50 buffer/methanol. The active cuts (approximately 1240 gmsA) were combined and diluted to a final concentration of 10% methanol by the addition of 1200 gallons of buffer. The use of dilution (rather than rotary evaporation) to reduce methanol concentration allowed the use of lower temperatures so as to minimize epi-hygromycin amounts, which tend to increase at higher temperatures. Half of this solution was loaded on a 40 liter CG-161 column (previously equilibrated with 4 bed volumes of a solution of 90/10 buffer/methanol). After loading, the column was washed with 4 bed volumes of 80/20 buffer/methanol and eluted with 5.5 bed volumes of 50/50 buffer/methanol. After regeneration and re-equilibration of the column, the second half of the activity was loaded on the column and eluted as described above. The combined cuts from both the runs (120 liters, approximately 1051 gmsA) were diluted to 10% methanol by the addition of buffer. This was re-loaded on the regenerated and re-equilibrated CG-161 resin column. Once the activity was adsorbed on the column, it was eluted with 4 bed volumes of methanol. This step served to both reduce the salts as well as increase the concentration of the sample prior to the final evaporation. The combined cuts from the final CG-161 column were evaporated to dryness to obtain a total of approximately 1 kgA of hygromycin A activity. The ratio of hygromycin A to epi-hygromycin in the final solids was about 14.5:1.

Experimental Procedures For Examples

In cases where final purification was effected using silica gel chromatography with an eluant system containing more than 10% methanol, the chromatographed product was taken up in 89:10:1 chloroform:methanol:concentrated ammonium hydroxide and filtered, or dissolved in methanol and passed through a 0.45 μM filter. Removal of solvent in vacuo provided the final product. In the procedures below, t-BOC refers to "tert-butoxycarbonyl".

5"-Oxime Ether Preparations
Preparation of Hydroxylamine Reagents For Synthesis of Oxime Ethers, Examples 1–92, 1A–116A The majority of hydroxylamine reagents employed were either commercially available (generally as an acid salt), or prepared from the corresponding alcohol or halide via the methods outlined below:

1) Preparation of Phthalimide-protected Benzylic or Aliphatic Hydroxylamines From the Alcohol A Mitsunobu reaction with diethyl azodicarboxylate and triphenylphosphine was used to couple N-hydroxyphthalimide and the alcohol starting material, according to the procedure of E. Grochowski and J. Jurczak, Synthesis (1976) 682.

From the bromide or chloride:

Reaction of N-hydroxyphthalimide (1 equivalent) with the halide starting material (1.2–2 equivalents) was carried out in DMSO solution, using potassium carbonate (0.6–2 equivalents) as base. The reactions were carried out at room temperature, generally by stirring overnight. Pouring the reaction mixture into cold water provided a precipitate, which was filtered to give the phthalimide-protected hydroxylamine. In many cases, this material was directly deprotected; silica gel chromatography can also be employed, using ethyl acetate-hexane mixtures, to purify the phthalimide-protected hydroxylamine.

2) Removal of the Phthalimide Protecting Group to Provide the Benzylic or Aliphatic Hydroxylamine Deprotection of the phthalimide-protected hydroxylamine was effected by reaction with hydrazine hydrate (1–2 equivalents) in ethanol solution, at temperatures ranging from room temperature to reflux, for periods ranging from 30 minutes to overnight. The reaction mixture was filtered, and the filtrate concentrated. This crude product can be taken to the next step as is, or can be further purified. Mixing the crude product with chloroform, removing solids by filtration and removal of solvent from the filtrate removes additional phthalhydrazide. Alternatively, the crude product was dissolved in 1N hydrochloric acid, and washed with ether or ethyl acetate. The aqueous layer was basified with saturated potassium carbonate solution and extracted with ether or ethyl acetate. Drying of the final organic layers and removal of solvent provided the hydroxylamine product.

3) Preparation of O-arylhydroxylamines

Substituted phenols were converted into the corresponding O-arylhydroxylamines through the use of mesitylenesulfonylhydroxylamine, as described by Y. Endo, K. Shudo and T. Okamoto, Synthesis (1980) 461.

Preparation of Miscellaneous Alcohol and Halide Starting Materials Used in Synthesis of Hydroxylamines In general, benzyl alcohol derivatives could be transformed into the corresponding benzyl bromides, if desired, by treatment with 48% HBr at 65° C. for 1–4 hours.

In a number of cases, alcohol starting materials were obtained by reduction of more highly oxidized commercially available compounds. 4-Cyclohexyl benzoic acid (Examples 46, 47) and 3-chloro-2-fluorobenzoic acid (Examples 13A, 14A) were reduced with lithium aluminum hydride (2–2.3 equivalents) in tetrahydrofuran to provide the corresponding alcohol. 3-(4-Chlorophenyl)propionic acid (Examples 56, 57), 3,4-dihydro-2H-1-benzopyran-2-carboxylic acid (Examples 36A, 37A), 4-chloro-3-sulfamoylbenzoic acid (Example 76A), 3-chlorothiophene-2-carboxylic acid (Examples 85A, 86A), 5-chlorothiophene-2-carboxylic acid (Examples 91A, 92A) and 2,6-dimethylbenzoic acid (Examples 98A, 99A) were reduced to the corresponding alcohols using diborane (1.1–2 equivalents) in tetrahydrofuran at 0° C. to room temperature for 5–18 hours. 2-Fluoro-6-methoxybenzonitrile was hydrolyzed to 2-fluoro-6-methoxybenzoic acid by treatment with 30% aqueous KOH at reflux, and the acid reduced to 2-fluoro-6-methoxybenzyl alcohol (Example 80A) with diborane as above. 3-Trifluoromethoxybenzaldehyde (Examples 62, 68), 3-cyanobenzaldehyde (Example 63), benzofuran-2-carboxaldehyde (Examples 65, 66), 1,4-benzodioxan-6-carboxaldehyde (Examples 83, 84), 3-fluoro-4-methoxybenzaldehyde (Examples 85, 86), 6-fluoro-4-chromanone (Examples 16A, 17A) 3-chloro-4-fluorobenzaldehyde (Examples 19A, 22A), quinoline-3-carboxaldehyde (Examples 23A, 24A), 4-chloro-3-fluorobenzaldehyde (Examples 25A, 26A), 2,3-(methylenedioxy)benzaldehyde (Examples 28A, 29A), 2,4-dichlorobenzaldehyde (Examples 45A, 47A), 2-chloro-4-fluorobenzaldehyde (Examples 46A, 48A), 2-fluoro-6-(trifluoromethyl)benzaldehyde (Examples 66A, 67A), 2,3-difluorobenzaldehyde (Examples 68A, 69A), 2-(difluoromethoxy)benzaldehyde (Examples 93A, 94A) and 6-chlorochromanone (Examples 102A, 103A) were reduced to the alcohol derivatives using sodium borohydride (1–2 equivalents) in tetrahydrofuran or methanol at 0° C. or room temperature.

Magnesium sulfate (4 equivalents) in methylene chloride was treated with concentrated sulfuric acid (1 equivalent), followed by 4-chloromethylbenzoic acid (1 equivalent) and tert-butanol (5.1 equivalents). Stirring overnight at room temperature provided the tert-butyl ester (Example 36).

4-Amino-3,5-dichlorobenzoic acid was N-acetylated by treatment with acetyl chloride (1.2 equivalents) in dimethylformamide at 90° C. for 4 hours. The cooled reaction mixture was poured into cold water, chilled and filtered to provide the acetamide derivative. Reduction of the carboxylic acid was effected with lithium aluminum hydride (2 equivalents) in tetrahydrofuran at 0° C. for 2 hours, to provide N-(2,6-dichloro-4-hydroxymethylphenyl)acetamide (Example 51).

3-(Aminomethyl)benzyl alcohol and 4-(aminomethyl) benzyl alcohol were prepared by reduction of 3- and 4-cyanobenzaldehyde using diborane (4–5 equivalents) in THF at room temperature overnight. The amino groups of 3-(aminomethyl)benzyl alcohol (Examples 8A and 9A) and 4-(aminomethyl)benzyl alcohol (Example 55) as well as 3-aminobenzyl alcohol (Example 54) were protected as the N-t-BOC derivatives by treatment with di-tert-butyl dicarbonate (1.1 equivalent) in THF at reflux until the starting amino compound was consumed.

Reaction of ethyl 4-fluorobenzoate with piperidine (3 equivalents) in acetonitrile was carried out at reflux for 4 days. Dilution of the cooled reaction mixture with several volumes of water provided a precipitate, which was filtered to provide ethyl 4-(piperidin-1-yl)benzoate. Reduction of the ester with lithium aluminum hydride (2 equivalents) in tetrahydrofuran gave the corresponding alcohol (Examples 71, 72).

5-Hydroxymethylbenzofuran (Examples 79, 80) was prepared according to the procedure of K. Hiroya, K. Hashimura and K. Ogasawara, Heterocycles (1994) 38, 2463.

2-Phenylpyrimidine-5-carboxaldehyde (Examples 81, 82) was prepared according to the procedure of J. T. Gupton, J. E. Gall, S. W. Riesinger et al., J. Heterocyclic Chemistry (1991) 28, 1281. The aldehyde was reduced to the corresponding alcohol using sodium borohydride in methanol.

3-Hydroxymethyl-4-phenylfuran (Examples 6A, 7A) was prepared according to the procedure of B. A. Keay and J-L. J. Bontront, Canadian J. Chemistry (1991) 69, 1326.

5-Chloro-2-fluorobenzyl bromide (Examples 12A, 32A) was prepared by the method of A. P. Krapcho, C. E. Gallagher, A. Mammach, M. Ellis, E. Menta, and A. Oliva, J. Heterocyclic Chemistry (1997), 34, 27–32.

2-Chloro-3,4-dimethoxybenzaldehyde was converted to 4-chloro-1,3-benzodioxole-5-carboxaldehyde by the method of S. T. Ross, R. G. Franz, J. W. Wilson, R. A. Hahn and H. M. Sarau, J. Heterocyclic Chemistry, (1986) 23, 1805. Reduction of the aldehyde was then carried out with sodium borohydride (1 equivalent) in THF at 0° C. to provide 4-chloro-1,3-benzodioxole-5-methanol (Examples 30A, 31 A).

4-Phenylfuroic acid was prepared by the method of M. E. Alonso, P. Jano, M. I. Hernandez, R. S. Greenberg and E. Wenkert, J. Organic Chemistry (1983) 48, 3047. Reduction to 2-(hydroxymethyl)-4-phenylfuran (Examples 34A, 35A) was carried out according to W. A. Scrivens, J. M. Tour, K. E. Creek, L. Pirisi, J. American Chemical Society (1994) 116, 4517.

3-Chloro-2,6-difluorobenzaldehyde was prepared from 1-chloro-2,4-difluorobenzene with n-buthyllithium and N,N-dimethylformamide by the method of A. S. Cantrell et al., J. Medicinal Chemistry (1996) 21, 4261. Reduction with sodium borohydride in methanol provided 3-chloro-2,6-difluorobenzyl alcohol, which was transformed into 3-chloro-2,6-difluorobenzyl bromide (Examples 38A, 39A) by treatment with 48% HBr at 65° C. for 3 hours. Similar treatment of 2,3,5,6-tetrafluorotoluene provided 2,3,5,6-tetrafluoro-4-methylbenzyl bromide (Examples 40A, 41A), and 3,5-difluorotoluene was similarly converted to 2,6-difluoro-4-methylbenzyl bromide (Examples 63A, 64A). 3,4-Difluoroanisole was similarly converted to 2,3-difluoro-6-(methoxy)benzyl bromide (Examples 74A, 75A), and 1-fluoro-3-(trifluoromethoxy)benzene converted to 2-fluoro-6-(trifluoromethoxy)benzyl bromide (Examples 77A, 78A). 2-Chloro-6-(trifluoromethoxy)benzyl alcohol (Examples 89A, 90A) was prepared in similar manner, except that lithium diisopropylamide was used in the formylation reaction, rather than n-butyllithium.

Vanillin was converted to 7-chloro-benzodioxole-5-carboxaldehyde by the method of T-T. Jong, P. G. Williard, and J. P. Porwoll, J. Organic Chemistry (1984) 49, 735. Reduction with sodium borohydride (1 equivalent) in methanol at room temperature then provided 7-chloro-1,3-benzodioxole-5-methanol (Examples 51A, 52A). In this case, transformation into the hydroxylamine reagent was carried out through intermediacy of a mesylate derivative, which was prepared by the method of R. K. Crossland and K. L. Servis, J. Organic Chemistry (1970)35, 3195.

3-Chloro-5-fluorobenzyl alcohol (Examples 53A, 54A) was prepared according to W. R. Meindl, E. Von Angerer, H. Schoenenberger, and G. Ruckdeschel, J. Medicinal Chemistry (1984) 27, 1111.

4-Phenyl-2-thiazolecarboxaldehyde was prepared by a method analogus to K. Inami and T. Shiba, Bull. Chem. Soc. Jpn., (1985) 58, 352. The aldehyde was reduced to the corresponding alcohol using sodium borohydride in ethanol. The corresponding 2-chloromethyl thiazole derivative (Examples 104A, 105A) was prepared by treatment of the alcohol with thionyl chloride (4 equivalents) in methylene chloride at room temperature for 2–5 hours.

2,4-Difluoropropiophenone was reduced to the corresponding alcohol (Examples 106A, 107A) using sodium borohydride in ethanol.

1-(3-Chloro-2,6-difluorophenyl)ethanol and other phenylethanol derivatives (Examples 108A–116A) were prepared by treatment of the corresponding benzaldehyde derivative with methylmagnesium bromide (1 equivalent) in THF at room temperature. These alcohols were then converted to the corresponding benzyl bromides by treatment with 48% HBr for 1–4 hours.

Preparation of Oxime Ethers, Methods (A–I), Examples 1–92, 1A–116A

Method A

A solution of hygromycin A (1 equivalent) and the hydrochloride salt of the appropriate hydroxylamine (1–2.2 equivalents) in methanol (roughly 0.1 M in hygromycin A) was treated with sodium carbonate (1.1–1.2 equivalents per equivalent of hydroxylamine salt) and heated to reflux for 15 minutes to 2 hours. The reactions can be followed by thin layer chromatography, using methanol/chloroform or methanol/chloroform/ammonium hydroxide eluants. The reaction mixture was then cooled to room temperature, and concentrated in vacuo. The crude product was purified by one of methods J to N.

Method B

A solution of hygromycin A (1 equivalent) and the hydrochloride salt of the appropriate hydroxylamine (1–2.2 equivalents) in methanol (roughly 0.1 M in hygromycin A) was treated with sodium carbonate (1.1–1.2 equivalents per equivalent of hydroxylamine salt) and heated to reflux for 18 hours. The reactions can be followed by thin layer chromatography, using methanol/chloroform or methanol/chloroform/ammonium hydroxide eluants. The reaction mixture was then cooled to room temperature, and concentrated in vacuo. The crude product was purified by one of methods J to N.

Method C

A solution of hygromycin A (1 equivalent) and the free base of the appropriate hydroxylamine (1–2.2 equivalents) in methanol (roughly 0.1 M in hygromycin A) was heated to reflux for 18 hours. The reactions can be followed by thin layer chromatography, using methanol/chloroform or methanol/chloroform/ammonium hydroxide eluants. The reaction mixture was then cooled to room temperature, and concentrated in vacuo. The crude product was purified by one of methods J to N.

Method D

A solution of hygromycin A (1 equivalent) and the free base of the appropriate hydroxylamine (1–2.2 equivalents) in methanol (roughly 0.1 M in hygromycin A) was heated to reflux for 5–6 hours. The reactions can be followed by thin layer chromatography, using methanol/chloroform or methanol/chloroform/ammonium hydroxide eluants. The reaction mixture was then cooled to room temperature, and concentrated in vacuo. The crude product was purified by one of methods J to N.

Method E

A solution of hygromycin A (1 equivalent) and the free base of the appropriate hydroxylamine (1–2.2 equivalents) in methanol (roughly 0.1 M in hygromycin A) was allowed to stir at room temperature for 18 hours. The reactions can be followed by thin layer chromatography, using methanol/chloroform or methanol/chloroform/ammonium hydroxide eluants. The reaction mixture was then concentrated in vacuo. The crude product was purified by one of methods J to N.

Method F

A solution of hygromycin A (1 equivalent) and the free base of the appropriate hydroxylamine (1–2.2 equivalents) in methanol (roughly 0.1 M in hygromycin A) was allowed to stir at room temperature for 1–5 hours. The reactions can be followed by thin layer chromatography, using methanol/chloroform or methanol/chloroform/ammonium hydroxide eluants. The reaction mixture was then concentrated in vacuo. The crude product was purified by one of methods J to N.

Method G

Separate solutions of hygromycin A (1 equivalent) and the free base of the appropriate hydroxylamine (1–2.2 equivalents) in methanol (final concentration, 0.5–0.1 M in hygromycin A) were combined at 0° C. and allowed to warm to room temperature over 1–2 hours. The reactions can be followed by thin layer chromatography, using methanol/chloroform or methanol/chloroform/ammonium hydroxide eluants. The reaction mixture was then concentrated in vacuo. The crude product was purified by one of methods J to N.

Method H

A solution of hygromycin A (1 equivalent) and the free base of the appropriate hydroxylamine (1–2.2 equivalents) in methanol (final concentration, 0.5–0.1 M in hygromycin A) was stirred at 0° C. for 2–3 hours. The reactions can be followed by thin layer chromatography, using methanol/chloroform or methanol/chloroform/ammonium hydroxide eluants. The reaction mixture was then concentrated in vacuo. The crude product was purified by one of methods J to N.

Method I

The substrate (see Tables for substrate employed) was dissolved in trifluoroacetic acid at a concentration of about 0.1 M, and allowed to stir at room temperature for 15 minutes, at which point the trifluoroacetic acid was removed in vacuo. Several volumes of a solution of 89:10:1 chloroform:methanol:concentrated ammonium hydroxide were added, and the volatiles removed in vacuo. The neutralization was repeated, and concentrated in vacuo to provide the crude product.

Purification of Oxime Ethers, Methods (J–N-1)

Method J

Purification was carried out by silica gel chromatography. The crude product was generally preadsorbed onto silica gel through addition of dry silica gel to a methanol solution of the product, followed by complete removal of solvent. Column elution was carried out using a solution of methanol in chloroform, generally 5% to 20%, often run as a step gradient.

Method K

Purification was carried out by silica gel chromatography. The crude product was generally preadsorbed onto silica gel through addition of dry silica gel to a methanol solution of the product, followed by complete removal of solvent. Column elution was carried out using a solution of methanol in methylene chloride, generally 5% to 20%, often run as a step gradient.

Method L

Purification was carried out by silica gel chromatography. The crude product was generally preadsorbed onto silica gel through addition of dry silica gel to a methanol solution of the product, followed by complete removal of solvent. Column elution was carried out using a ternary solution of chloroform:methanol:ammonium hydroxide, ranging in composition from 289:10:1 to 39:10:1, depending on the $R_f$ of the products and starting materials. Columns were generally run as a step gradient. In the case of Example 55 the final column eluant was 73:25:2.

Method M

Purification was carried out by silica gel chromatography. The crude product was generally preadsorbed onto silica gel through addition of dry silica gel to a methanol solution of the product, followed by complete removal of solvent. Column elution was carried out using a ternary solution of methylene chloride:methanol:ammonium hydroxide, ranging from 322:10:1 to 56:10:1, often run as a step gradient.

Method N

Purification was carried out by $C_{18}$ reversed-phase chromatography, eluting with a methanol-water solution of 10% to 100%, depending on the $R_f$ of the products and starting materials. Columns were generally run as a step gradient.

Method N-1

Purification was carried out by $C_{18}$ reversed-phase chromatography, eluting with a mixture of acetonitrile and 10 mM pH 7 potassium phosphate buffer. The isolated components were minor products of the reaction mixture, obtained from epi-hygromycin (alpha stereochemistry at C-4") present in the hygromycin starting material.

5"-Amine Preparations, Examples 93–101

Methods (O–R) for Preparation of Amine Derivatives

Method O

A solution of hygromycin A in methanol (0.1 M) was treated with the amine (1 equivalent) and allowed to stir at room temperature for 10 minutes. Acetic acid (3 equivalents) was added, followed by sodium triacetoxyborohydride (3 equivalents), and the reaction mixture was allowed to stir for an additional 24 hours. After treatment with a small volume of aqueous saturated sodium bicarbonate solution, solvents were removed in vacuo. The residue was purified by silica gel chromatography, eluting with a mixture of chloroform:methanol:ammonium hydroxide, ranging in composition from 89:10:1 to 70:28:2, often as a step gradient.

Method P

A solution of hygromycin A in methanol (0.1 M) was treated with the amine (2–4 equivalents) and allowed to stir at room temperature for 1 hour. In cases where imine formation is sluggish, 3 Angstrom molecular sieves were added, and the mixture stirred overnight. Sodium borohydride (1–2 equivalents) was then added, and the reaction stirred for 2–24 hours. After treatment with a small volume of aqueous saturated sodium bicarbonate solution (and removal of sieves, if present, by filtration), solvents were removed in vacuo, and the residue was purified by silica gel chromatography, eluting with a mixture of chloroform::methanol:ammonium hydroxide, ranging in composition from 89:10:1 to 80:19:1.

Method Q

The amino hygromycin A derivative in water (0.1 M) was treated with formaldehyde (5 equivalents) then formic acid (10 equivalents) and stirred at 90° C. for 5 hours, then at room temperature for 48 hours. After addition of saturated aqueous sodium bicarbonate, the reaction mixture was stirred and then the clear supernatant was decanted off. The remaining residue was purified by column chromatography using as eluant chloroform:methanol:ammonium hydroxide in a ratio of 80:19:1.

Method R

A solution of hygromycin A in methanol (0.1 M) was treated with an aniline (4 equivalents) and crushed 3 Angstrom molecular sieves and stirred at 50° C. for 2 hours or 70° C. overnight. After the reaction mixture had cooled to room temperature, sodium borohydride (1–2 equivalents) was added and stirring was continued for 2–48 hours at room temperature. A small volume of saturated aqueous sodium bicarbonate was added, the sieves were removed by filtration, and the filtrate was concentrated in vacuo. The crude residue was purified by column chromatography on silica gel, using 80:19:1 chloroform:methanol:ammonium hydroxide as eluant.

5"-Amide Preparations, Examples 102–104

Preparation of Amide Derivatives, Methods S–T
Synthesis of Persilylated 5"-amino Hygromycin A a) A solution of hygromycin A, tert-butyldimethylsilyl chloride (12 equivalents), and imidazole (12 equivalents) in DMF (hygromycin concentration 0.25 M) were stirred at 80° C. for 20 hours. After removal of the DMF under reduced pressure, the resulting residue was extracted with diethyl ether. The combined ether extracts were washed with water, then saturated sodium chloride solution, dried over sodium sulfate, filtered, and concentrated. The crude product was purified by silica gel chromatography, eluting with 10% ethyl acetate/hexanes.

b) A solution of persilylated hygromycin A in 1:1 methanol:tetrahydrofuran (0.2 M) was treated with sodium borohydride (0.5 equivalents) and stirred at room temperature for 18 hours. After removal of solvents under reduced pressure, the residue was dissolved in chloroform, washed with saturated sodium bicarbonate solution, dried over sodium sulfate, filtered, and concentrated to give crude persilylated 5"-alcohol. Purification was carried out by column chromatography eluting with 10%–20% ethyl acetate/hexanes. Subsequent analysis of Mosher esters showed the stereochemistry at 5" of the major product of this reaction to be R.

c) A solution of the 5"-alcohol in methylene chloride (0.2 M) at 0° C. was treated with triethylamine (3 equivalents), followed by methanesulfonyl chloride (2 equivalents) and stirred at room temperature for 24 hours. The reaction mixture was then poured into water and extracted with methylene chloride. The combined organic layers were dried over sodium sulfate, filtered, and concentrated in vacuo to give the 5"-mesylate.

d) The 5"-mesylate in DMF (0.2 M) was treated with sodium azide (10 equivalents) and stirred at 95° C. for 18 hours. The reaction mixture was poured into water, extracted with diethyl ether, washed with brine, dried with sodium sulfate, filtered, and concentrated in vacuo. The crude 5"-azide was purified by silica gel chromatography, eluting with 10% ethyl acetate/hexanes.

e) A solution of the 5"-azide and triphenylphosphine (3 equivalents) in toluene (5"-azide concentration 0.2 M) was stirred at 105° C. 18 hours. The toluene was removed under reduced pressure and replaced with tetrahydrofuran/water (10/1) (hygromycin derivative concentration 0.1 M) and stirred at 75° C. 5 hours. The reaction mixture was poured into water and extracted with diethyl ether. The combined organic layers were washed with brine, dried over sodium sulfate, filtered, and concentrated in vacuo. The crude product was purified by silica gel chromatography, eluting with 20% ethyl acetate/hexanes, to provide persilylated 5"-amino hygromycin A.

Method S a) Persilylated 5"-amino hygromycin A and the appropriate carboxylic acid (2 equivalents) were stirred together with EEDQ (1-ethoxycarbonyl-2-ethoxy-1,2-dihydroquinoline, 2 equivalents) in THF at 70° C. for three hours (persilylated hygromycin concentration 0.1 M). The reaction mixture was poured into water and extracted with ether. The combined organic layers were washed with 5% sodium carbonate solution, water, and saturated sodium chloride solution. After being dried over sodium sulfate, the organic extracts were filtered and concentrated to provide a residue which was chromatographed on silica gel using a mixture of ethyl acetate and hexanes, to provide the desired amide as its persilyl protected derivative.

b) The silyl groups were removed by treatment of a solution of 5"-modified hexasilylhygromycin A (1 equivalent, 0.1 M) with a 1M solution of tetrabutylamonium fluoride (TBAF, 10 equivalents) in THF at room temperature for 14–24 hours. The THF was removed in vacuo and the crude material was dissolved in a mixture of water and methanol. This solution/suspension was applied to a column of Dowex (50X4-400) resin (10–30 g of resin/mmol of TBAF, which had been converted to the OH form by treatment with 0.1–0.2N sodium hydroxide and then washed with one column volume (CV) of water). The column was gravity eluted with 1–3 CV of water until the TBAF was removed and then eluted with 50% aqueous methanol with the aid of nitrogen pressure to provide the desired amide product. If additional purification was required, silica gel chromatography was performed (method J–N).

Method T

A solution of the appropriate carboxylic acid (1.2 equivalents) in tetrahydrofuran was treated with DEPC (diethyl phosphoryl cyanide, 1.2 equivalents) and triethylamine (1.2 equivalents) and the reaction mixture was stirred for 10 minutes. Persilylated 5"-amino hygromycin A (1 equivalent) was added (final hygromycin derivative concentration 0.17 M) and the reaction was allowed to proceed at room temperature for 48 hours. The reaction mixture was poured into water and extracted with ether. The combined organic layers were washed with aqueous sodium carbonate, water, and saturated sodium chloride solution, then dried over sodium sulfate, filtered, and concentrated in vacuo. The crude material was purified by silica gel chromatography, using a mixture of ethyl acetate and hexanes.

The silylated amide was deprotected with TBAF as in Method S, step b.

5"-Ether, Carbamate Preparations, Examples 105–131

Methods (U–Z)

Alkylation or acylation of persilylated 5"-hydroxy hygromycin A (see Examples 102–104 section, procedures a and b) was achieved through procedures U through Y and the silyl groups were subsequently removed using method S, step b.

Method U for the Preparation of 5"-hygromycin A Benzyl Ethers

Sodium hydride (60% dispersion in mineral oil, 10 equivalents) was weighed into an oven-dried round bottomed flask and washed 3 times with hexanes. The residual hexanes were removed in vacuo and to this was added tetrahydrofuran (THF) (persilylated 5"-hygromycin A concentration 0.1 M), persilylated 5"-hydroxy hygromycin A (1 equivalent), and a benzyl bromide (10 equivalents) at rt. The resultant slurry was heated at 50° C. for 1–4 hours. The reaction was cooled to rt, quenched with water and then extracted two times with chloroform (CHCl$_3$). The combined organics were washed with brine, dried over MgSO$_4$ and concentrated to a semisolid which was then chromatographed (SiO$_2$, 5–15% EtOAc:toluene or EtOAc:hexanes) (EtOAc refers to ethyl acetate) to provide the desired ether.

Method V

Potassium tert-butoxide (5 equivalent of a 1M solution in THF) was added to a solution of persilylated 5"-hydroxy hygromycin A (1 equivalent) and a benzyl bromide (10 equivalents) in THF (0.1 M in persilylated 5"-hydroxy hygromycin A) at rt. The reaction was complete after 15 minutes. The reaction was quenched by the addition of water and the product was extracted into chloroform. The combined organic extracts were dried over MgSO$_4$, concentrated in vacuo and chromatographed (SiO$_2$, 5–15% EtOAc:toluene or EtOAc:hexanes) to provide the desired product.

Method W

Potassium tert-butoxide (2 equivalents of a 1M solution in THF) was added in a dropwise fashion over 5 minutes to a solution of persilylated 5"-hydroxy hygromycin A (1 equivalent) and a benzyl bromide (5 equivalents) in dioxane (0.1 M in persilylated 5"-hydroxy hygromycin) at room temperature. The reaction was complete after 15 minutes. The reaction was quenched by the addition of water and the product was extracted into chloroform. The combined organic extracts were dried over $MgSO_4$, concentrated in vacuo and chromatographed ($SiO_2$, 5–15% EtOAC:toluene or EtOAc:hexanes) to provide the desired product.

Method X

Phenyl isocyanate (7 equivalents) was added to a solution of persilylated 5"-hydroxy hygromycin A (1 equivalent) in toluene (0.05 M in persilylated 5"-hydroxy hygromycin) and heated to 60° C. for 12–24 hours. The crude reaction mixture was concentrated and chromatographed ($SiO_2$, 5–15% EtOAc:toluene or EtOAc:hexanes) to provide the silylated product.

Method Y

Benzyl isocyanate (7 equivalents) was prepared by the method of Sigurdsson, S. Th.; Seeger, B.; Kutzke, U.; and Eckstein, F., J. Org. Chem. (1996) 61, 3883. This was added to a solution of persilylated 5"-hydroxy hygromycin A (1 equivalent), dimethylaminopyridine (0.2 equivalents) and triethylamine (4 equivalents) in toluene (0.05 M in persilylated 5"-hydroxy hygromycin) and heated to 70° C. for 12–24 hours. The crude reaction mixture was concentrated and chromatographed ($SiO_2$, 5–7% EtOAc:hexanes) to provide the silylated material.

Method Z

Persilylated 5"-hydroxy hygromycin A was treated with $K_2CO_3$ (1.3 equivalents) in methanol (0.1 M) and stirred 14–20 hours. The methanol was removed in vacuo and the residue taken up in 1:1 EtOAc:hexanes and water. The organics were washed with $NaHCO_3$ and brine, dried over $MgSO_4$ and concentrated. Without further purification this material was then treated with allyl bromide (1–3 equivalents) and $K_2CO_3$ (1.4 equivalents) in DMF (0.1 M) for 14–24 hours. The reaction mixture was poured into hexane and washed with water. The organics were dried over $MgSO_4$, filtered and concentrated to a white foam consisting of the allyl-protected phenolic hydroxyl group, which was used without further purification. The 5"-alcohol was alkylated with benzyloxychloromethyl ether under the conditions of method X. The allyl group was removed using the method of Jaynes, B. H., Elliot, N. C. and Schicho, D. L. J. Antibiot. (1992) 45, 1705. The silyl groups were then removed using Method S, step b.

5"-Olefin Preparations, Examples 132–140

Preparation of Olefin Derivatives, Methods AA–EE

Method AA

A solution of hygromycin A and (carboethoxymethylene) triphenylphosphorane (2 equivalents) in DMF (0.1 M in hygromycin A) was stirred at 70° C. for 15 hours. The DMF was removed under reduced pressure and the resulting residue was chromatographed on silica gel with a mixture of chloroform, methanol and ammonium hydroxide (80:19:1) to give the unsaturated ester of Example 132.

Method BB

The ethyl ester from Example 132 was dissolved in water and tetrahydrofuran (1:1) (0.25 M), treated with sodium hydroxide (3 equivalents) and stirred at room temperature for 6 hours. After removal of the tetrahydrofuran under reduced pressure, the pH was adjusted to 4 by the addition of 1N HCl. The aqueous solution was concentrated to dryness under reduced pressure and the resulting residue was slurried with MeOH and filtered. The filtrate was concentrated to give the carboxylic acid of Example 133.

Method CC

A solution of the carboxylic acid of Example 133, DCC (dicyclohexylcarbodiimide, 1 equivalent), and HOBT (hydroxybenzotriazole, 1 equivalent) in DMF (0.25 M) was treated with the appropriate amine (1 equivalent) and the reaction mixture was stirred at room temperature for 18 hours. After removal of the DMF under reduced pressure, the resulting oil was chromatographed on silica gel using a mixture of chloroform, methanol and ammonium hydroxide (89:10:1) to provide the desired amide.

Method DD

A mixture of the carboxylic acid of Example 133 and 1-(3-dimethylaminopropyl)-3-ethyl-carbodiimide hydrochloride (1 equivalent) in DMF (0.25 M) was treated with the appropriate amine (1 equivalent) and the reaction mixture was stirred at room temperature for 18 hours. After removal of the DMF under reduced pressure, the residue was purified by silica gel chromatography using chloroform, methanol and ammonium hydroxide, in concentrations ranging from 89:10:1 to 80:19:1.

Method EE

The product of Example 133 in dimethylformamide (0.25 M) was treated with EEDQ (1-ethoxycarbonyl-2-ethoxy-1, 2-dihydroquinoline, 1.2–2 equivalents) and the appropriate amine (1 equivalent) and stirred at 70° C. overnight. After cooling, the reaction mixture was either concentrated in vacuo to provide a crude product for purification, or the reaction mixture was poured into chloroform, and the resulting solid filtered to provide the crude product.

Specific compounds prepared according to the above processes are illustrated in the tables below. In the tables, "Ex" means example, "Mol Wt" means molecular weight, "Stereo" means stereochemistry of the oxime moiety (E or Z), "Pro" means procedure used to prepare the compounds, and "Mass Spec" means mass spectrometry.

Using the specific and general chemistry described above, the compounds listed below may be prepared in analogous fashion. Each of the compounds listed below is part of the present invention and possesses activity against bacterial infections. Literature references or preparative information are provided for the requisite alcohol or halide when those starting materials are not commercially available.

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,3-dihydrobenzofuran-6-yl)methyl]oxime. 6-Benzofurancarboxaldehyde can be prepared by the method of A. S. Tasker et al. J. Med. Chem. (1997) 40, 322. Reduction of the aldehyde with sodium borohydride and hydrogenation of the double bond over palladium on carbon provides 2,3-dihydro-6-benzofuranmethanol.

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,3-dihydrobenzofuran-6-yl)methyl]oxime. 6-Benzofurancarboxaldehyde can be prepared by the method of A. S. Tasker et al. J. Med. Chem. (1997) 40, 322. Reduction of the aldehyde with sodium borohydride and hydrogenation of the double bond over palladium on carbon provides 2,3-dihydro-6-benzofuranmethanol.

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,3-dihydrobenzofuran-5-yl)methyl]oxime. Reduction of 2,3-dihydro-5-benzofurancarboxaldehyde with sodium borohydride provides 2,3-dihydro-5-benzofuranmethanol.

5-Deoxy-5-[[3-[4-[(6-deoxy-β-D-arabino-hexofuranos-5-ulos-1-yl)oxy]-3-hydroxyphenyl]-2-methyl-1-oxo-2-(E)- propenyl]amino]-1,2-O-methylene-D-neo-inositol, (Z)-O-[(2,3-dihydrobenzofuran-5-yl)methyl]oxime. Reduction of 2,3-dihydro-5-benzofurancarboxaldehyde with sodium borohydride provides 2,3-dihydro-5-benzofuranmethanol.

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(1,2,3,4-tetrahydronaphthalen-1-yl)oxime.

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(1,2,3,4-tetrahydronaphthalen-1-yl)oxime.

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(7-chloro-1,2,3,4-tetrahydronaphthalen-1-yl)oxime. 7-Chloro-3,4-dihydro-1(2H)-naphthalenone can be prepared by the method of W. M. Owton and M. Brunavs, Syn. Comm. (1991) 21, 981. Reduction with sodium borohydride provides 7-chloro-1,2,3,4-tetrahydro-1-naphthalenol.

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(7-chloro-1,2,3,4-tetrahydronaphthalen-1-yl)oxime. 7-Chloro-3,4-dihydro-1(2H)-naphthalenone can be prepared by the method of W. M. Owton and M. Brunavs, Syn. Comm. (1991) 21, 981. Reduction with sodium borohydride provides 7-chloro-1,2,3,4-tetrahydro-1-naphthalenol.

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(7-fluoro-1,2,3,4-tetrahydronaphthalen-1-yl)oxime. 7-Fluoro-3,4-dihydro-1(2H)-naphthalenone can be prepared by the method of W. M. Owton and M. Brunavs, Syn. Comm. (1991) 21, 981. Reduction with sodium borohydride provides 7-fluoro-1,2,3,4-tetrahydro-1-naphthalenol.

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(7-fluoro-1,2,3,4-tetrahydronaphthalen-1-yl)oxime. 7-Fluoro-3,4-dihydro-1(2H)-naphthalenone can be prepared by the method of W. M. Owton and M. Brunavs, Syn. Comm. (1991) 21, 981. Reduction with sodium borohydride provides 7-fluoro-1,2,3,4-tetrahydro-1-naphthalenol.

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(8-chloro-3,4-dihydro-2H-1-benzopyran-4-yl)oxime. The procedure of G. Ariamala and K. K. Balasubramanian, Tet. Lett. (1988) 29, 3487 can be used to prepare 8-chloro-2,3-dihydro-4H-1-benzopyran-4-one; reduction with sodium borohydride then provides 8-chloro-3,4-dihydro-2H-1-benzopyran-4-ol.

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(8-chloro-3,4-dihydro-2H-1-benzopyran-4-yl)oxime. The procedure of G. Ariamala and K. K. Balasubramanian, Tet. Lett. (1988) 29, 3487 can be used to prepare 8-chloro-2,3-dihydro-4H-1-benzopyran-4-one; reduction with sodium borohydride then provides 8-chloro-3,4-dihydro-2H-1-benzopyran-4-ol.

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(8-fluoro-3,4-dihydro-2H-1-benzopyran-4-yl)oxime. The procedure of R. Sarges et al., J. Med. Chem. (1988) 31, 230 can be used to prepare 8-fluoro-2,3-dihydro-4H-1-benzopyran-4-one; reduction with sodium borohydride then provides 8-fluoro-3,4-dihydro-2H-1-benzopyran-4-ol.

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(8-fluoro-3,4-dihydro-2H-1-benzopyran-4-yl)oxime. The procedure of R. Sarges et al., J. Med. Chem. (1988) 31, 230 can be used to prepare 8-fluoro-2,3-dihydro-4H-1-benzopyran-4-one; reduction with sodium borohydride then provides 8-fluoro-3,4-dihydro-2H-1-benzopyran-4-ol.

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[4-(phenylmethyl)phenylmethyl]oxime. Reduction of 4-(phenylmethyl)benzoic acid with diborane provides 4-(phenylmethyl)benzenemethanol.

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[4-(phenylmethyl)phenylmethyl]oxime. Reduction of 4-(phenylmethyl)benzoic acid with diborane provides 4-(phenylmethyl)benzenemethanol.

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[4-(phenoxy)phenylmethyl]oxime. Reduction of 4-phenoxybenzaldehyde with sodium borohydride provides 4-phenoxybenzenemethanol.

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[4-(phenoxy)phenylmethyl]oxime. Reduction of 4-phenoxybenzaldehyde with sodium borohydride provides 4-phenoxybenzenemethanol.

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(3-difluoromethoxy-phenyl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(3-difluoromethoxy-phenyl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(4-difluoromethoxy-phenyl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(4-difluoromethoxy-phenyl)oxime;

TABLE 1

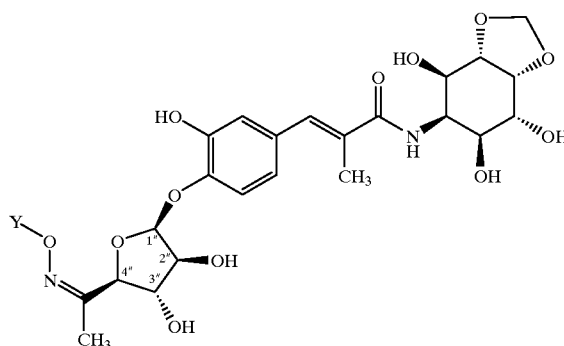

Most of the examples in Table 1 bear the C-4" stereochemistry shown, with the oxime moiety in the beta orientation. Some examples have the oxime in the alpha orientation; this is indicated in the Stereo column

| Ex. | Y | Mol Wt | Stereo | Pro. | Mass spec | 1H NMR peaks (CD$_3$OD) |
|---|---|---|---|---|---|---|
| 1 | tert-butyl | 582.61 | E | A or B, L | 583.1 | 5.69(d, J=4.2Hz, 1H), 4.28(d, J=8.1Hz, 1H), 1.22(s, 9H) |
| 2 | 2-propen-1-yl | 566.57 | E | B, L | 567.1 | 5.93(m, 1H), 5.55(d, J=4.4Hz, 1H), 5.20(dd, J=17.2, 1.7Hz, 1H), 5.11 (dd, J=10.4, 1.7Hz, 1H), 4.50(d, J=5.6Hz, 2H), 4.23(d, J=7.9Hz, 1H) |
| 3 | ethyl | 554.46 | E | B, L | 555.1 | 5.69(d, J=4.2Hz, 1H), 4.23(d, J=7.9Hz, 1H), 4.04(q, J=7.1Hz, 2H), 1.18(t, J=7.1Hz, 3H) |
| 4 | ethyl | 554.46 | Z | B, L | 555.1 | 5.64(d, J=4.2Hz, 1H), 5.14(d, J=6.2Hz, 1H), 4.03(q, J=7.1Hz, 2H), 1.20(t, J=7.1Hz, 3H) |
| 5 | isobutyl | 582.61 | Z | B, L | 583.2 | 5.66(d, J=4.2Hz, 1H), 5.18(d, J=6.2Hz, 1H), 3.77(d, J=6.6Hz, 2H), 1.95(m, 1H), 092(d, J=6.8Hz, 3H) |
| 6 | (4-nitrophenyl)methyl | 661.63 | E | B, L | 662.1 | 8.14(d, J=8.9Hz, 2H), 7.49(d, J=8.9Hz, 2H), 5.54(d, J=4.6Hz, 1H), 5.17(s, 2H), 4.25(d, J=7.9Hz, 1H) |
| 7 | (4-chlorophenyl)methyl | 651.07 | Z | B, L | 651.1 | 7.32(m, 4H), 5.65(d, J=4.2Hz, 1H), 5.20(d, J=6 Hz, 1H), 5.02(AB quartet, Δv=10.8Hz, J=12.8Hz, 2H) |
| 8 | (4-chlorophenyl)methyl | 651.07 | E | B, L | 651.1 | 7.28(s, 4H), 5.55(d, J=4.6Hz, 1H), 5.03(s, 2H), 4.26(d, J=7.7Hz, 1H) |
| 9 | (4-methylphenyl)methyl | 630.66 | Z | B, L | 631.2 | 7.2(d, J=8Hz, 2H), 7.1 (d, J=8Hz, 2H), 5.64(d, J=4.4Hz, 1H), 5.18(d,J=6.4Hz, 1H), 4.98(AB quartet, Δv=15.7Hz, J=12.1Hz, 2H) |
| 10 | (4-methylphenyl)methyl | 630.66 | E | B, L | 631.2 | 7.17(d, J=8Hz, 2H), 7.10(d, J=8Hz, 2H), 5.55(d, J=4.4Hz, 1H), 4.99(s, 2H), 4.25(d. J=7.9Hz, 1H), 2.28(s, 3H) |
| 11 | (4-methoxyphenyl)methyl | 646.65 | Z | B, L | 647.2 | 7.27(d, J=8.7Hz, 2H), 6.87(d, J=8.7Hz, 2H), 5.64(d, J=4.4Hz, 1H), 5.16(d, J=6.2Hz, 1H), 4.95(AB quartet, Δv=16.0Hz, J=11.7Hz, 2H) |
| 12 | (4-methoxyphenyl)methyl | 646.65 | E | B, L | 647.2 | 7.22(d, J=8.3Hz, 2H), 6.83(d, J=8.5Hz, 2H), 5.55(d, J=4.6Hz, 1H), |

TABLE 1-continued

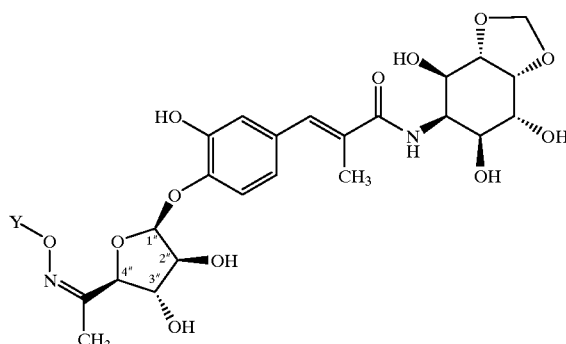

Most of the examples in Table 1 bear the C-4" stereochemistry shown, with the oxime moiety in the beta orientation. Some examples have the oxime in the alpha orientation; this is indicated in the Stereo column

| Ex. | Y | Mol Wt | Stereo | Pro. | Mass spec | 1H NMR peaks (CD$_3$OD) |
|---|---|---|---|---|---|---|
| 13 | (3,4-dichlorophenyl)methyl | 685.52 | Z | B, L | 685.1, 687.1 | 4.97(s, 2H), 4.26(d, J=7.9Hz, 1H), 3.75(s, 3H) 7.51(d, J=1.9Hz, 1H), 7.45(d, J=8.3Hz, 1H), 7.26(dd, J=8.3, 2.1Hz, 1H), 5.65(d, J=4.4Hz, 1H), 5.22(d, J=6.2Hz, 1H), 5.00(AB quartet, Δν = 7.3Hz, J=13.3Hz, 2H) |
| 14 | (3,4-dichlorophenyl)methyl | 685.52 | E | B, L | 685.1, 687.1 | 7.44(m, 2H), 7.23(m, 1H), 5.55(d, J=4.4Hz, 1H), 5.02(s, 2H), 4.25(d, J=7.7Hz, 1H) |
| 15 | 4-pyridylmethyl | 617.62 | E | B, L | 618.1 | 8.43(d, J=5.8Hz, 2H), 7.32(d, J=5.8Hz, 2H), 5.56(d, J=4.6Hz, 1H), 5.13(s, 2H), 4.25(d, J=7.7Hz, 1H) |
| 16 | phenylmethyl | 616.63 | Z | B, L | 617.2 | 7.34(m, 5H), 5.65(d, J=4.4Hz, 1H), 5.21(d, J=6.2Hz, 1H), 5.04(AB quartet, Δν=14.4Hz, J=12.3Hz, 2H) |
| 17 | phenylmethyl | 616.63 | E | B, L | 617.2 | 7.32(m, 5H), 5.55(d, J=4.6Hz, 1H), 5.05(s, 2H), 4.26(d, J=7.7Hz) |
| 18 | cyclohexylmethyl | 622.68 | Z | C, L | 623.2 | 5.65(d, J=4.2Hz, 1H), 5.16(d, J=6.2Hz, 1H), 3.78(m, 2H), 1.72(m, 6H), 1.22(m, 3H), 0.96(m, 2H) |
| 19 | cyclohexylmethyl | 622.68 | E | C, L | 623.2 | 5.55(d, J=4.6Hz, 1H), 4.24(d, J=7.9Hz, 1H), 3.82(m, 2H), 1.68(m, 6H), 1.21(m, 3H), 0.94(m, 2H) |
| 20 | 2-pyridylmethyl | 617.62 | Z | C, L | 618.1 | 8.49(bd, J=4.8Hz, 1H), 7.82(ddd, apparent td, J=7.7, 1.7Hz, 1H), 7.45(d, J=7.9Hz, 1H), 7.32(m, 1H), 5.66(d, J=4.2Hz, 1H), 5.24(d, J=6.2Hz, 1H), 5.15(AB quartet, Δν = 10.9Hz, J=14.1Hz, 2H) |
| 21 | 2-pyridylmethyl | 617.62 | E | C, L | 618.1 | 8.45(bd, J=5.0Hz, 1H), 7.79(ddd, apparent td, J=7.8, 1.7Hz, 1H), 7.40(d, J=7.9Hz, 1H), 7.31(dd, J=7.6Hz, 4.9Hz, 1H), 5.56(d, J=4.6Hz, 1H), 5.15(s, 2H), 4.25(d, J=7.7 Hz, 1H) |
| 22 | (4-fluorophenyl)methyl | 634.62 | Z | C, L | 635.1 | 7.36(dd, J=8,5Hz, 2H), 7.04(dd, apparent triplet, J=8.8Hz, 2H), 5.65(d, J= |

TABLE 1-continued

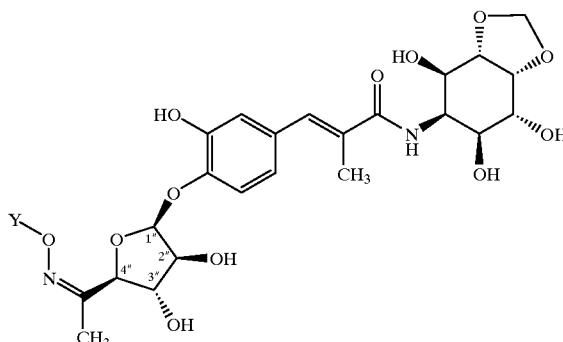

Most of the examples in Table 1 bear the C-4" stereochemistry shown, with the oxime moiety in the beta orientation. Some examples have the oxime in the alpha orientation; this is indicated in the Stereo column

| Ex. | Y | Mol Wt | Stereo | Pro. | Mass spec | 1H NMR peaks (CD$_3$OD) |
|---|---|---|---|---|---|---|
| 23 | (4-fluorophenyl)methyl | 634.62 | E | C, L | 635.1 | 4.2Hz, 1H), 5.20(d, J=6.4Hz, 1H), 5.01(AB quartet, Δν=12.0Hz, J=12.6Hz, 2H) 7.32(dd, J=8.5, 5.4Hz, 2H), 7.01(dd, apparent t, J=8.9Hz, 2H), 5.55(d, J=4.36Hz, 1H), 5.02(s, 2H), 4.25(d, J=7.9Hz, 1H) |
| 24 | (2,4-dichlorophenyl)methyl | 685.52 | E | C, L | 685.1; 687.0 | 7.42(d, J=2.1Hz, 1H), 7.34(d, J=8.3Hz, 1H), 7.26(dd, J=8.3, 2.1Hz, 1H), 5.56(d, J=4.6Hz, 1H), 5.13(s, 2H), 4.26(d, J=7.7Hz, 1H) |
| 25 | (2,4-dichlorophenyl)methyl | 685.52 | Z | C, L | 685.1; 687.0 | 7.46(d, J=8.3Hz, 1H), 7.43(d, J=1.9Hz, 1H), 7.30(dd, J=8.3, 2.1Hz, 1H), 5.66(d, J=4.2Hz, 1H), 5.25(d, J=6.4Hz, 1H), 5.11(AB quartet, Δν = 9.1Hz, J=14.0Hz, 2H) |
| 26 | (2,3,4,5,6-pentafluorophenyl)-methyl | 706.58 | E | C, L | 707.2 | 5.54(d, J=4.6Hz, 1H), 5.16(s, 2H), 4.21(d, J=7.9Hz, 1H) |
| 27 | (3,4-difluorophenyl)methyl | 652.61 | E | C, L | 653.2 | 7.17(m, 3H), 5.56(d, J=4.4Hz, 1H), 5.02(s, 2H), 4.25(d, J=7.9Hz, 1H) |
| 28 | (4-trifluoromethylphenyl)-methyl | 684.63 | E | C, L | 685.2 | 7.58(d, J=8.1Hz, 2H), 7.46(d, J=7.9Hz, 2H), 5.54(d, J=4.4Hz, 1H), 5.13(s, 2H), 4.24(d, J=7.9Hz, 1H) |
| 29 | (3-trifluoromethylphenyl)-methyl | 684.63 | E | C, L | 685.2 | 7.57(m, 3H), 7.49(m, 1H), 5.55(d, J=4.4Hz, 1H), 5.12(s, 2H), 4.25(d, J=7.7Hz, 1H) |
| 30 | (2-chlorophenyl)methyl | 651.07 | E | C, L | 651.2; 653.1 | 7.35(m, 2H), 7.24(m, 2H), 5.56(d, J=4.6Hz, 1H), 5.17(s, 2H), 4.26(d, J=7.9Hz, 1H) |
| 31 | (2,3-dichlorophenyl)-methyl | 685.52 | E | C, L | 685.1; 687.1 | 7.42(d, J=7.7Hz, 1H), 7.27(m, 2H), 5.55(d, J=4.6Hz, 1H), 5.17(s, 2H), 4.25(d, J=7.7Hz, 1H) |
| 32 | (4-acetamido phenyl)methyl | 673.68 | E | C, L | 674.2 | 7.47(d, J=8.3Hz, 2H), 7.24(d, J=8.3Hz, 2H), 5.55(d, J=4.6Hz, 1H), 5.00(s, 2H), 4.25(d, J=7.9Hz, 1H) |
| 33 | 2-pyrazinylmethyl | 618.6 | E | C, L | 619.2 | 8.59(s, 1H), 8.54(bs, 1H), 8.50(bs, 1H), 5.55(d, J=4.4Hz, 1H), 5.21(s, 2H), 4.24(d, J=7.7Hz, 1H) |

TABLE 1-continued

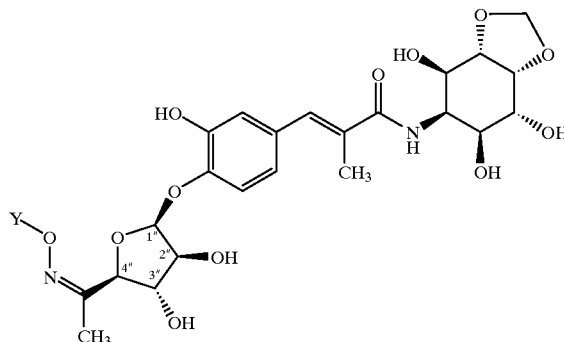

Most of the examples in Table 1 bear the C-4" stereochemistry shown, with the oxime moiety in the beta orientation. Some examples have the oxime in the alpha orientation; this is indicated in the Stereo column

| Ex. | Y | Mol Wt | Stereo | Pro. | Mass spec | 1H NMR peaks (CD$_3$OD) |
|---|---|---|---|---|---|---|
| 34 | 4-pyrimidinylmethyl | 618.6 | E | C, L | 619.2 | 9.03(s, 1H), 8.67(bd, J=5.2Hz, 1H), 7.40(d, J=5.2Hz, 1H), 5.56(d, J=4.4Hz, 1H), 5.15(s, 2H), 4.25(d, J=7.5Hz, 1H) |
| 35 | 4-pyrimidinylmethyl | 618.6 | Z | C, L | 619.2 | 9.07(s, 1H), 8.73(m, 1H), 7.57(d, J=5.2Hz, 1H), 5.68(d, J=4.2Hz, 1H), 5.29(d, J=6.4Hz, 1H), 5.16(bs, 2H) |
| 36 | [4-(tert-butoxycarbonyl)phenyl]methyl | 716.75 | E | C, L | 717.3 | 7.88(d, J=8Hz, 2H), 7.36(d, J=8Hz, 2H), 5.55(d, J=4.6Hz, 1H), 5.12(s, 2H), 4.25(d, J=7.7Hz, 1H), 1.57(s, 9H) |
| 37 | 2-amino-5-thiazolylmethyl | 638.66 | E | C, L | 639.1 | 6.44(s, 1H), 5.55(d, J=4.4Hz, 1H), 4.26(d, J=7.9Hz, 1H) |
| 38 | [3-(tert-butoxycarbonylamino)-phenyl]methyl | 731.76 | E | E, L | 732.3 | 7.36(bs, 1H), 7.29(bd, J=8.5Hz, 1H), 7.18(dd, apparent t, J=7.9Hz, 1H), 6.94(d, J=7.7Hz, 1H), 5.56(d, J=4.6Hz, 1H), 5.01(s, 2H), 4.26(d, J=7.9Hz, 1H), 1.49(s, 9H) |
| 39 | 3-furanylmethyl | 606.59 | E | E, L | 607.2 | 7.46(s, 1H), 7.40(s, 1H), 6.41(s, 1H), 5.56(d, J=4.6Hz, 1H), 4.92(s, 2H), 4.26(d, J=7.9Hz, 1H) |
| 40 | phenylmethyl | 616.63 | E | F, L | 617.3 | 7.28(m, 5H), 5.55(d, J=4.6Hz, 1H), 5.05(s, 2H), 4.26(d, J=7.9Hz, 1H) |
| 41 | ![structure] | 660.64 | E | F, L | 661.3 | 6.76(m, 2H), 6.70(d, J=7.7Hz, 1H), 5.88(s, 2H), 5.53(d, J=4.6Hz, 1H), 4.92(s, 2H), 4.24(d, J=7.7Hz, 1H) |

TABLE 1-continued

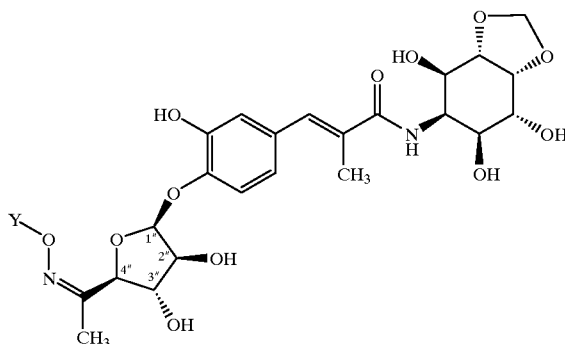

Most of the examples in Table 1 bear the C-4" stereochemistry shown, with the oxime moiety in the beta orientation. Some examples have the oxime in the alpha orientation; this is indicated in the Stereo column

| Ex. | Y | Mol Wt | Stereo | Pro. | Mass spec | 1H NMR peaks (CD$_3$OD) |
|---|---|---|---|---|---|---|
| 42 | (methylenedioxyphenyl)methyl | 660.64 | Z | F, L | 661.2 | 6.83(d, J=0.4Hz, 1H), 6.79(d, J=7.9Hz, 1H), 6.73(dd, J=7.9, 0.4Hz, 1H), 5.88(s, 2H), 5.62(d, J=4.4Hz, 1H), 5.15(d, J=6.2Hz, 1H), 4.90(AB quartet, Δv=14.0Hz, J=12.0Hz, 2H) |
| 43 | 4-biphenylylmethyl | 692.73 | E | E, L | 693.1 | 7.57(m, 4H), 7.39(m, 4H), 7.31(m, 1H), 5.56(d, J=4.6Hz, 1H), 5.10(s, 2H), 4.28(d, J=7.9Hz, 1H) |
| 44 | diphenylmethyl | 692.73 | E | E, L | 693.1 | 7.24(m, 10H), 6.14(s, 1H), 5.52(d, J=4.4Hz, 1H), 4.21(d, J=7.9Hz, 1H) |
| 45 | (4-carboxy phenyl)methyl | 660.64 | E | I (using product of Example 36), N | 661.2 | 7.94(d, J=8.1Hz, 2H), 7.38(d, J=8.1Hz, 2H), 5.55(d, J=4.4Hz, 1H), 5.13(s, 2H), 4.26(d, J=7.7Hz, 1H) |
| 46 | (4-cyclohexyl phenyl)methyl | 698.8 | E | F, J | 699.1 | 7.20(d, J=8.3Hz, 2H), 7.13(d, J=8.1Hz, 2H), 5.55(d, J=4.6Hz, 1H), 5.01(s, 2H), 4.26(d, J=7.9Hz, 1H), 2.46(m, 1H), 1.81(m, 4H), 1.75(m, 1H), 1.41(m, 4H), 1.28(m, 1H) |
| 47 | (4-cyclohexyl phenyl)methyl | 698.8 | Z | F, J | 699.3 | 7.16(m, 4H), 5.65(d, J=4.2Hz, 1H), 5.19(d, J=6.2Hz, 1H), 4.99(AB quartet, Δv=15.6Hz, J=12.0Hz, 2H), 2.46(m, 1H), 1.82(m, 4H), 1.74(m, 1H), 1.42(m, 4H), 1.27(m, 1H) |
| 48 | 2-furanylmethyl | 606.59 | Z | E, L | 607.2 | 7.46(s, 1H), 6.37(m, 2H), 5.64(d, J=4.4Hz, 1H), 5.12(d, J=6.2Hz, 1H), 4.95(AB quartet, Δv=9.5Hz, J=13.1Hz, 2H) |
| 49 | 2-furanylmethyl | 606.59 | E | E, L | 607.2 | 7.43(s, 1H), 6.35(m, 2H), 5.55(d, J=4.4Hz, 1H), 4.96(s, 2H), 4.26(d, J=7.9Hz, 1H) |
| 50 | (3-fluoro phenyl)methyl | 634.62 | Z | G, L | 635.2 | 7.32(m, 1H), 7.15(m, 1H), 7.11(bd, J=8Hz, 1H), 6.99(bdd, apparent bt, J=8.3Hz, 1H), 5.66(d, J=4.2Hz, 1H), 5.24(d, J= |

TABLE 1-continued

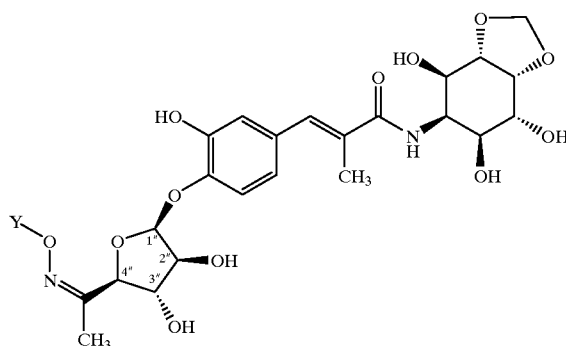

Most of the examples in Table 1 bear the C-4" stereochemistry shown, with the oxime moiety in the beta orientation. Some examples have the oxime in the alpha orientation; this is indicated in the Stereo column

| Ex. | Y | Mol Wt | Stereo | Pro. | Mass spec | 1H NMR peaks (CD$_3$OD) |
|---|---|---|---|---|---|---|
| | | | | | | 6.4Hz, 1H), 5.04(AB quartet, Δv=9.9Hz, J= 13.2Hz, 2H) |
| 51 | (4-acetamido-3,5-dichlorophenyl)methyl | 742.57 | E | F, L | 742.0; 743.9 | 7.37(s, 2H), 5.54(d, J= 4.6Hz, 1H), 5.00(s, 2H), 4.23(d, J=7.9Hz, 1H), 2.13(s, 3H) |
| 52 | [4-[(tert-butoxycarbonylamino)-methyl]phenyl]methyl | 745.79 | E | E, L | 746.1 | 7.24(AB quartet, Δv= 18.4Hz, J=8.1Hz, 4H), 5.55(d, J=4.6Hz, 1H), 5.03(s, 2H), 4.25(d, J= 7.7Hz, 1H)4.19(s, 2H), 1.43(s, 9H) |
| 53 | [4-(tert-butoxycarbonylamino)-methyl]phenyl]methyl | 745.79 | Z | E, L | 746.1 | 7.27(AB quartet, Δv= 28.3Hz, J=8.1Hz, 4H), 5.64(d, J=4.4Hz, 1H), 5.20(d, J=6.4Hz, 1H), 5.01(AB quartet, Δv= 13.9Hz, J=12.3Hz, 2H), 4.20(s, 2H), 1.44(s, 9H) |
| 54 | (3-aminophenyl)methyl | 631.64 | E | I (using product of Example 38), L | 632.1 | 7.07(t, J=7.7Hz, 1H), 6.76(bs, 1H), 6.70(m, 2H), 5.54(d, J=4.6Hz, 1H), 4.95(s, 2H), 4.24(d, J=7.9Hz, 1H) |
| 55 | (4-aminomethylphenyl)-methyl | 645.67 | E | I(using product of Example 52), L | 645.9 | 7.26(s, 4H), 5.52(d, J= 4.6Hz, 1H), 5.02(s, 2H), 4.22(d, J=7.9Hz, 1H), 3.75(s, 2H) |
| 56 | 3-(4-chlorophenyl)prop-1-yl | 679.13 | Z | E, J | 679.2; 681.2 | 7.24(d, J=8.3Hz, 2H), 7.16(d, J=8.3Hz, 2H), 5.67(d, J=4.2Hz, 1H), 5.17(d, J=6.4Hz, 1H), 4.00(m, 2H), 2.68(t, J= 7.6Hz, 2H), 1.91(m, 2H) |
| 57 | 3-(4-chlorophenyl)prop-1-yl | 679.13 | E | E, J | 679.2; 681.2 | 7.21(d, J=8.3Hz, 2H), 7.12(d, J=8.5Hz, 2H), 5.56(d, J=4.6Hz, 1H), 4.26(d, J=7.7Hz, 1H), 4.02(t, J=6.3Hz, 2H), 2.62(t, J=7.6Hz, 2H), 1.90(m, 2H) |
| 58 | 2-benzimidazolylmethyl | 656.65 | E | E, L | 657.2 | 7.52(m, 2H), 7.21(m, 2H), 5.57(d, J=4.6Hz, 1H), 5.27(s, 2H), 4.28(d, J= 7.9Hz, 1H) |
| 59 | 2-benzimidazolylmethyl | 656.65 | Z | E, L | 657.1 | 7.54(m, 2H), 7.22(m, 2H), 5.67(d, J=4.4Hz, 1H), 5.33(d, J=6.8Hz, 1H), 5.27(s, 2H) |
| 60 | 2-phenylethyl | 630.66 | Z | E, J | 631.1 | 7.22(m, 5H), 5.63(d, J= 4.2Hz, 1H), 5.09(d, J= 6.2Hz, 1H), 4.15(m, 2H), |

TABLE 1-continued

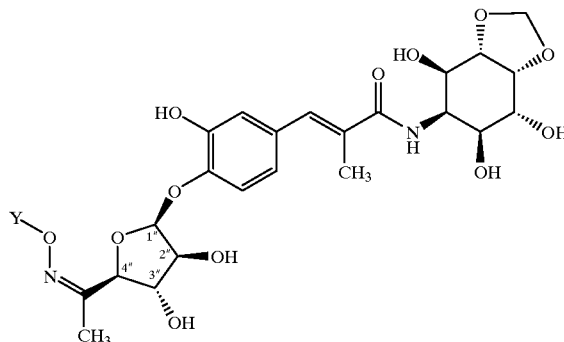

Most of the examples in Table 1 bear the C-4" stereochemistry shown, with the oxime moiety in the beta orientation. Some examples have the oxime in the alpha orientation; this is indicated in the Stereo column

| Ex. | Y | Mol Wt | Stereo | Pro. | Mass spec | 1H NMR peaks (CD$_3$OD) |
|---|---|---|---|---|---|---|
| 61 | 2-phenylethyl | 630.66 | E | E, J | 631.1 | 2.90(t, J=7.0Hz, 2H) 7.12(m, 5H), 5.53(d, J= 4.6Hz, 1H), 4.27(d, J= 7.7Hz, 1H), 4.17(t, J= 6.7Hz, 2H), 2.85(t, J= 6.8Hz, 2H) |
| 62 | [3-(trifluoromethoxy)phenyl]methyl | 700.62 | E | E, L | 701 | 7.39(t, J=7.9Hz, 1H), 7.30(d, J=7.9Hz, 1H), 7.20(bs, 1H), 7.16(bd, J= 8.1Hz, 1H), 5.55(d, J= 4.6Hz, 1H), 5.09(s, 2H), 4.25(d, J=7.9Hz, 1H) |
| 63 | (3-cyanophenyl)methyl | 641.64 | E | E, L | 642.1 | 7.61(m, 3H), 7.46(dd, apparent t, J=7.7Hz, 1H), 5.53(d, J=4.6Hz, 1H), 5.08(s, 2H), 4.23(d, J=7.9Hz, 1H) |
| 64 | (3,4-dimethoxyphenyl)methyl | 676.68 | E | E, L | 677.1 | 6.90(m, 2H), 6.84(s, 1H), 5.53(d, J=4.6Hz, 1H), 4.96(s, 2H), 4.25(d, J= 7.9Hz, 1H), 3.77(s, 3H), 3.76(s, 3H) |
| 65 | 2-benzofuranylmethyl | 656.65 | E | E, L | 657.1 | 7.51(d, J=7.7Hz, 1H), 7.39(d, J=8.1Hz, 1H), 7.22(m, 1H), 7.15(m, 1H), 6.71(s, 1H), 5.53(d, J= 4.6Hz, 1H), 5.11(s, 2H), 4.26(d, J=7.9Hz, 1H) |
| 66 | 2-benzofuranylmethyl | 656.65 | Z | E, L | 657.1 | 7.53(d, J=7.1Hz, 1H), 7.42(d, J=8.3Hz, 1H), 7.24(m, 1H), 7.17(m, 1H), 6.75(s, 1H), 5.62(d, J= 4.2Hz, 1H), 5.17(d, J= 6.2Hz, 1H), 5.10(AB quartet, Δv=6.9Hz, J= 13.7Hz, 2H) |
| 67 | (3,4-dimethoxyphenyl)methyl | 676.68 | Z | E, L | 677.1 | 6.88(m, 3H), 5.62(d, J= 4.2Hz, 1H), 5.17(d, J= 6.4Hz, 1H), 4.94(AB quartet, Δv=17.2Hz, J= 12.0Hz, 2H), 3.80(s, 3H), 3.79(s, 3H) |
| 68 | [3-(trifluoromethoxy)phenyl]methyl | 700.63 | Z | E, L | 701.0 | 7.34(bd, J= 6.4Hz, 1H), 7.27(bs, 1H), 7.16(m, 1H), 5.66(d, J= 3.9Hz, 1H), 5.23(d, J= 6.2Hz, 1H), 5.07(AB quartet, Δv=9.2Hz, J= 13.1Hz, 2H) |
| 69 | 2-anilinoethyl | 645.67 | Z | E, L | 646.2 | 7.08(dd, J=8.5, 7.5Hz, 2H), 6.66(dd, J=8.6, 0.9 Hz, 2H), 6.62(t, J=7.3 Hz, 1H), 5.62(d, J=4.2 Hz, 1H), 5.18(d, J=6.4 |

TABLE 1-continued

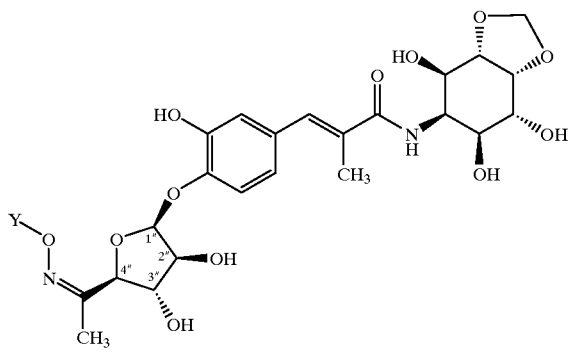

Most of the examples in Table 1 bear the C-4" stereochemistry shown, with the oxime moiety in the beta orientation. Some examples have the oxime in the alpha orientation; this is indicated in the Stereo column

| Ex. | Y | Mol Wt | Stereo | Pro. | Mass spec | 1H NMR peaks (CD$_3$OD) |
|---|---|---|---|---|---|---|
| 70 | 2-anilinoethyl | 645.67 | E | E, L | 646.1 | Hz, 1H), 4.15(m, 2H), 3.27 (m, 2H) 7.04(dd, J=8.6, 7.4Hz, 2H), 6.60(dd, J=8.6, 0.9 Hz, 2H), 6.56(t, J=7.4 Hz, 1H), 5.55(d, J=4.6 Hz, 1H), 4.25(d, J=7.7 Hz, 1H), 4.16(m, 2H), 3.31 (m, 2H) |
| 71 | [4-(1-piperidino)phenyl]-methyl | 699.76 | E | H, J | 700.1 | 7.15(d, J=8.5Hz, 2H), 6.87(d, J=8.7Hz, 2H), 5.52(d, J=4.6Hz, 1H), 4.92(s, 2H), 4.24(d, J=7.7Hz, 1H), 3.06(dd, J=5.4, 5.4Hz, 4H), 1.65(m, 4H), 1.54(m, 2H) |
| 72 | [4-(1-piperidino)phenyl]-methyl | 699.76 | Z | H, J | 700.1 | 7.23(d, J=8.8Hz, 2H), 6.93(d, J=8.8Hz, 2H), 5.63(d, J=4.3Hz, 1H), 5.15(d, J=6.4Hz, 1H), 4.93(AB quartet, Δv=17.3Hz, J=11.8Hz, 2H), 3.11(dd, J=5.4, 5.4Hz, 4H), 1.69(m, 4H), 1.58(m, 2H) |
| 73 | 3-phenylprop-1-yl | 644.68 | Z | E, J | 645.1 | 7.20(d, J=7.3Hz, 2H), 7.13(m, 3H), 5.64(d, J=4.2Hz, 1H), 5.18(d, J=6.4Hz, 1H), 3.97(m, 2H), 2.65(t, J=7.7Hz, 2H), 1.90(m, 2H) |
| 74 | 3-phenylprop-1-yl | 644.68 | E | E, J | 645.1 | 7.18(d, J=7.3Hz, 2H), 7.11(m, 3H), 5.54(d, J=4.4Hz, 1H), 4.24(d, J=7.9Hz, 1H)4.01(t, J=6.3 Hz, 2H), 2.61(t, J=7.7 Hz, 2H), 1.89(m, 2H) |
| 75 | (2-fluorophenyl)methyl | 634.62 | Z | G, L | 635.2 | 7.44(apparent td, J=7.5, 1.8Hz, 1H), 7.30(m, 1H), 7.14(m, 1H), 7.06(dd, J=10.2, 8.3Hz, 1H), 5.65(d, J=4.2Hz 1H), 5.20(d, J=6.4Hz, 1H), 5.11(AB quartet, Δv=9.1Hz, J=12.9Hz, 1H) |
| 76 | (2-fluorophenyl)methyl | 634.62 | E | G, L | 635.2 | 7.36(apparent td, J=7.5, 1.5Hz, 1H), 7.28(m, 1H), 7.12(m, 1H), 7.04(dd, J=10.1, 8.4Hz, 1H), 5.55(d, J=4.6Hz, 1H), 5.12(s, 2H), 4.26(d, J=7.9Hz, 1H) |
| 77 | 2-(phenylthio)ethyl | 662.71 | Z | F, J | 663.1 | 7.35(d, J=7.3Hz, 2H), 7.26(dd, apparent t, J= |

TABLE 1-continued

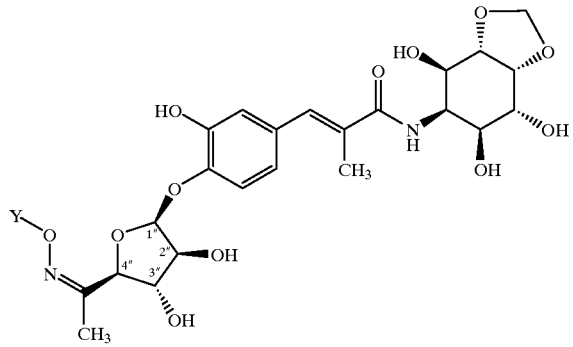

Most of the examples in Table 1 bear the C-4" stereochemistry shown, with the oxime moiety in the beta orientation. Some examples have the oxime in the alpha orientation; this is indicated in the Stereo column

| Ex. | Y | Mol Wt | Stereo | Pro. | Mass spec | 1H NMR peaks (CD$_3$OD) |
|---|---|---|---|---|---|---|
| | | | | | | 7.7Hz, 2H), 7.15(m, 1H), 5.63(d, J=4.4Hz, 1H), 5.09(d, J=6.2Hz, 1H), 4.10(t, J=6.9Hz, 2H), 3.15(t, J=6.7Hz, 2H) |
| 78 | 2-(phenylthio)ethyl | 662.71 | E | F, J | 663.1 | 7.31(d, J=7.3Hz, 2H), 7.22(m, 2H), 7.10(m, 1H), 5.55(d, J=4.4Hz, 1H), 4.23(d, J=7.9Hz, 1H), 4.18(m, 2H), 3.12(m, 2H) |
| 79 | 5-benzofuranylmethyl | 656.64 | E | F, K | 657.1 | 7.69(d, J=2.3Hz, 1H), 7.54(bs, 1H), 7.39(d, J=8.5Hz, 1H), 7.23(dd, J=8.6, 1.6Hz, 1H), 6.76(m, 1H), 5.53(d, J=4.6Hz, 1H), 5.11(s, 2H), 4.25(d, J=7.9Hz, 1H) |
| 80 | 5-benzofuranylmethyl | 656.64 | Z | F, K | | 7.71(d, J=2.3Hz, 1H), 7.59(bs, 1H), 7.43(d, J=8.5Hz, 1H), 7.29(dd, J=8.5, 1.5Hz, 1H), 6.79(m, 1H), 5.62(d, J=4.2Hz, 1H), 5.18(d, J=6.4Hz, 1H), 5.10(AB quartet, Δν = 15.0Hz, J=11.9Hz, 2H) |
| 81 | 2-phenyl-5-pyrimidinylmethyl | 694.69 | Z | F, M | 695.1 | 8.82(s, 2H), 8.36(m, 2H), 7.46(m, 3H), 5.63(d, J=4.4Hz, 1H), 5.2(d, J obscured, 1H), 5.10(s, 2H) |
| 82 | 2-phenyl-5-pyrimidinylmethyl | 694.69 | E | F, M | 695.1 | 8.75(s, 2H), 8.33(m, 2H), 7.45(m, 3H), 5.52(d, J=4.6Hz, 1H), 5.10(s, 2H), 4.25(d, J=7.9Hz, 1H) |
| 83 | | 674.66 | Z | F, L | 675.1 | 6.83(d, J=1.9Hz, 1H), 6.78(AB quartet, Δν=14.1Hz, J=8.2Hz, 2H), 5.64(d, J=4.2Hz, 1H), 5.16(d, J=6.2Hz, 1H), 4.90(AB quartet, Δν=15.2Hz, J=11.8Hz, 2H), 4.20(s, 4H) |

TABLE 1-continued

Most of the examples in Table 1 bear the C-4" stereochemistry shown, with the oxime moiety in the beta orientation. Some examples have the oxime in the alpha orientation; this is indicated in the Stereo column

| Ex. | Y | Mol Wt | Stereo | Pro. | Mass spec | 1H NMR peaks (CD$_3$OD) |
|---|---|---|---|---|---|---|
| 84 | (2,3-dihydro-1,4-benzodioxin-6-yl)methyl (structure shown) | 674.66 | E | F, L | 675.2 | [D$_2$O]6.73(m, 3H), 5.51 (d, J=4.8Hz, 1H), 4.82 (s, 2H), 4.14(s, 4H), 4.06 (d, J=7.9Hz, 1H) |
| 85 | (3-fluoro-4-methoxyphenyl)methyl | 664.65 | E | E, L | 665.1 | 7.05(m, 2H), 7.00(dd, apparent t, J=8.2Hz, 1H), 5.56(d, J=4.6Hz, 1H), 4.97(s, 2H), 4.26(d, J=7.9Hz, 1H) |
| 86 | (3-fluoro-4-methoxyphenyl)methyl | 664.65 | Z | E, L | 665.1 | 7.13(m, 1H), 7.09(bd, J= 6.8Hz, 1H), 7.03(m, 1H), 5.65(d, J=4.2Hz, 1H), 5.19(d, J=6.4Hz, 1H), 4.95(AB quartet, Δv= 12.2Hz, J=12.3Hz, 2H) |
| 87 | 2-phenoxyethyl | 646.65 | Z | E, J | 647.2 | 7.25(dd, apparent t, J= 7.3Hz, 2H), 6.93(m, 3H), 5.64(d, J=4.2Hz, 1H), 5.13(d, J=6.0Hz, 1H), 4.33(m, 2H), 4.18(m, 2H) |
| 88 | 2-phenoxyethyl | 646.65 | E | E, J | 647.2 | 7.21(dd, apparent t, J= 7.7Hz, 2H), 6.88(m, 3H), 5.56(d, J=4.6Hz, 1H), 4.34(m, 2H), 4.27(d, J= 7.9Hz, 1H), 4.15(m, 2H) |
| 89 | (3-fluorophenyl)methyl | 634.62 | E | G, L | 635.1 | 7.30(m, 1H), 7.11(m, 1H), 7.03(bd, J=9.7Hz, 1H), 6.98(bdd, apparent bt, J= 8.6Hz, 1H), 5.56(d, J= 4.6Hz, 1H), 5.06(s, 2H), 4.26(d, J=7.9Hz, 1H) |
| 90 | (chroman-4-yl) (structure shown) | 658.66 | Z; major and minor diastereomer | F, J | 659.2 | 7.33(dd, J=7.6, 1.8Hz) and 7.25(d, J=7.7Hz) [1H], 7.15(m, 1H), 6.85 (m, 1H), 6.75(d, J=8.3 Hz, 1H), 5.61(d, J=4.4 Hz) and 5.59(d, J=4.4 Hz)[1H], 5.11(d, J=6.4 Hz) and 5.14(d, J=6.8 Hz)[1H], 5.07(m) and 5.02 (m)[1H], 4.15(m, 2H), 2.21(bd, J=14.5Hz) and 2.29(bd, J=14.9Hz)[1H], 2.03(m, 1H) |

TABLE 1-continued

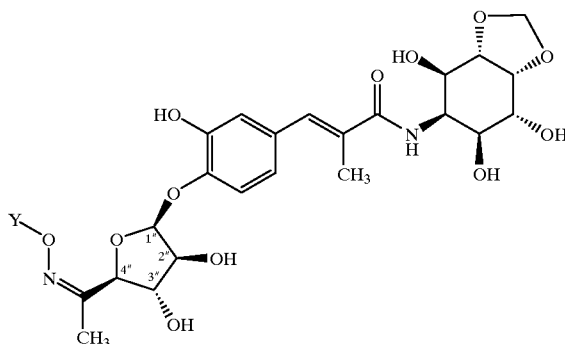

Most of the examples in Table 1 bear the C-4" stereochemistry shown, with the oxime moiety in the beta orientation. Some examples have the oxime in the alpha orientation; this is indicated in the Stereo column

| Ex. | Y | Mol Wt | Stereo | Pro. | Mass spec | 1H NMR peaks (CD$_3$OD) |
|---|---|---|---|---|---|---|
| 91 | [chroman-4-yl] | 658.66 | E; mixture of 2 diastereomers | F, J | 659.2 | 7.22(m, 1H), 7.12(m, 1H), 6.80(m, 1H), 6.72(d, J=8.1Hz, 1H), 5.56(d, J=3.5Hz, 1H), 5.06(m, 1H), 4.30(d, J=7.5Hz) and 4.30(d, J=7.9Hz)[1H], 4.15(m, 2H), 2.23(bd, J=12.9Hz) and 2.20(bd, J=13.6Hz)[1H], 2.01(m, 1H) |
| 92 | (3-chlorophenyl)methyl | 651.07 | E | D, L | 651.1; 653.1 | 7.29(bs, 1H), 7.23(m, 3H), 5.54(d, J=4.4Hz, 1H), 5.02(s, 2H), 4.24(d, J=7.9Hz, 1H) |
| 1A | [benzofurazan-5-ylmethyl] | 658.63 | E | E, L | 659.1 | (DMSO-d$_6$)8.01(d, J=9.3 Hz, 1H), 7.87(s, 1H), 7.51 (d, J=9.1Hz, 1H), 5.56 (d, J=4.2Hz, 1H), 5.17 (s, 2H), 4.10(d, J=7.9 Hz, 1H) |
| 2A | [6-chloro-1,3-benzodioxol-5-ylmethyl] | 695.08 | E | F, L | 695.1; 697.1 | (DMSO-d$_6$)7.04(s, 1H), 6.92(s, 1H), 6.02(s, 2H), 5.53(d, J=4.6Hz, 1H), 4.96(s, 2H), 4.07(d, J=7.9Hz, 1H) |
| 3A | [6-chloro-1,3-benzodioxol-5-ylmethyl] | 695.08 | Z | F, L | 695.1; 697.1 | 6.96(s, 1H), 6.86(s, 1H), 5.97(s, 2H), 5.66(d, J=4.2Hz, 1H), 5.23 (obscured, presumed d, 1H), 5.04(AB quartet, Δν=8.1Hz, J=13.2Hz, 2H) |
| 4A | (3,5- | 685.52 | Z | F, L | 685.0; | 7.30(bs, 3H), 5.64(d, J= |

TABLE 1-continued

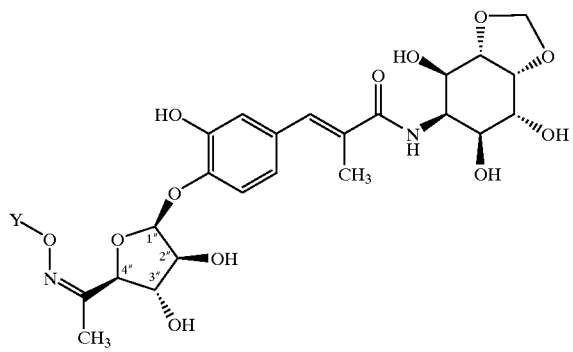

Most of the examples in Table 1 bear the C-4" stereochemistry shown, with the oxime moiety in the beta orientation. Some examples have the oxime in the alpha orientation; this is indicated in the Stereo column

| Ex. | Y | Mol Wt | Stereo | Pro. | Mass spec | 1H NMR peaks (CD$_3$OD) |
|---|---|---|---|---|---|---|
|  | dichlorophenyl)methyl |  |  |  | 687.0 | 4.4Hz, 1H), 5.22(d, J= 6.4Hz, 1H), 4.99(bs, 2H) |
| 5A | (3,5-dichlorophenyl)methyl | 685.52 | E | F, L | 685.1; 687.1 | 7.30(t, J=2.0Hz, 1H), 7.24(d, J=1.9Hz, 2H), 5.53(d, J=4.4Hz, 1H), 5.01(s, 2H), 4.24(d, J=7.9Hz, 1H) |
| 6A | 4-phenyl-3-furanylmethyl | 682.69 | E | F, L | 683.1 | 7.64(d, J=1.9Hz, 1H), 7.59(bs, 1H), 7.43(bd, J=8Hz, 2H), 7.31(bt, J=8Hz, 2H), 7.25(m, 1H), 5.56(d, J=4.6Hz, 1H), 5.00(s, 2H), 4.27(d, J=7.9Hz, 1H) |
| 7A | 4-phenyl-3-furanylmethyl | 682.69 | Z | F, L | 683.1 | 7.66(d, J=1.7Hz, 1H), 7.64(bs, 1H), 7.50(bd, J=8Hz, 2H), 7.38(bt, J=8Hz, 2H), 7.29(m, 1H), 5.64(d, J=4.2Hz, 1H), 5.13(d, J=6.4Hz, 1H), 4.98(AB quartet, Δv=21.6Hz, J=12.0Hz, 2H) |
| 8A | (3-[(tert-butoxycarbonyl)amino methyl]phenyl)methyl | 745.79 | Z | F, L | 746.1 | 7.26(m, 3H), 7.20(m, 1H), 5.66(d, J=4.4Hz, 1H), 5.21(d, J=6Hz, 1H), 5.03(AB quartet, Δv=13.4Hz, J=12.5Hz, 2H), 4.21(m, 2H) |
| 9A | (3-[(tert-butoxycarbonyl)amino methyl]phenyl)methyl | 745.79 | E | F, L | 746.1 | 7.24(m, 2H), 7.19(m, 2H), 5.56(d, J=4.6Hz, 1H), 5.05(s, 2H), 4.26(d, J=7.9Hz, 1H), 4.20(m, 2H) |
| 10A | (3-chlorophenyl)methyl | 651.07 | Z | D, L | 651.1; 653.1 | 7.35(bs, 1H), 7.26(m, 3H), 5.64(d, J=4.4Hz, 1H), 5.21(d, J=6.4Hz, 1H), 5.01(AB quartet, Δv = 10.2Hz, J=13.0Hz, 2H) |
| 11A | (3,5-difluorophenyl)methyl | 652.61 | E | F, L | 653.1 | 6.90(m, 2H), 6.82(m, 1H), 5.56(d, J=4.6Hz, 1H), 5.06(s, 2H), 4.26(d, J=7.9Hz, 1H) |
| 12A | (5-chloro-2-fluorophenyl)methyl | 669.06 | E | F, L | 669.0; 671.0 | 7.34(dd, J=6.2, 2.6Hz), 7.27(ddd, J=8.8, 4.5, 3.0 Hz, 1H), 7.05(dd, apparent t, J=9.2Hz, 1H), 5.54(d, J=4.4Hz, 1H), 5.07(s, 2H), 4.24(d, J=7.7Hz, 1H) |
| 13A | (3-chloro-2-fluorophenyl)methyl | 669.06 | Z | E, L | 669.0; 671.0 | 7.37(apparent dd, J=7.7, 6.9Hz, 2H), 7.1(m, 1H), 5.64(d, J=4.4Hz, 1H), 5.19(d, J=6.2Hz, 1H), 5.10(bs, 2H) |

TABLE 1-continued

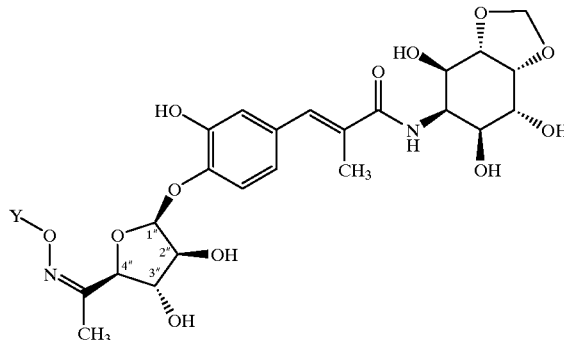

Most of the examples in Table 1 bear the C-4" stereochemistry shown, with the oxime moiety in the beta orientation. Some examples have the oxime in the alpha orientation; this is indicated in the Stereo column

| Ex. | Y | Mol Wt | Stereo | Pro. | Mass spec | 1H NMR peaks (CD$_3$OD) |
|---|---|---|---|---|---|---|
| 14A | (3-chloro-2-fluorophenyl)methyl | 669.06 | E | E, L | 669.0; 671.0 | 7.36(m, 1H), 7.28(m, 1H), 7.08(m, 1H), 5.54(d, J=4.4Hz, 1H), 5.11(s, 2H), 4.23(d, J=7.7Hz, 1H) |
| 15A | (3,5-difluorophenyl)methyl | 652.61 | Z | F, L | 653.1 | 6.94(m, 2H), 6.80 (tt, J=9.2, 2.4Hz, 1H), 5.64(d, J=4.2Hz, 1H), 5.23(d, J=6.4Hz, 5.02 (presumed AB quartet, J=14Hz, 2H) |
| 16A | ![chroman-F] | 676.66 | Z | F, L | 677.2 | 7.12(m, 1H), 6.93(m, 1H), 6.77(dd, J=9.1, 4.8Hz, 1H), 5.64(d, J=4.4Hz, 1H), 5.16(d, J=6.6Hz, 1H), 5.07(m, 1H), 4.12(m, 1H), 2.21(m, 1H), 2.06(m, 1H) |
| 17A | ![chroman-F] | 676.66 | E; mixture of diastereomers | F, L | 677.2 | 7.00(ddd, apparent dt, J=8.7, 2.8Hz, 1H), 6.92(m, 1H), 6.75(dd, J=8.9, 4.6 Hz, 1H), 5.60 and 5.59(d, J=4.4 and 4.6Hz, 1H), 5.08(m, 1H), 4.33 and 4.32(d, J=7.7 and 7.9 Hz, 1H), 4.22(m, 1H), 4.04 (m,1H), 2.22(m, 1H), 2.03 (m, 1H) |
| 18A | (3-aminomethylphenyl)methyl | 645.67 | E | I (using product of Example 9A), L | 646.1 | 7.29(m, 4H), 5.56(d, J=4.6Hz, 1H), 5.07(s, 2H), 4.26(d, J=7.9Hz, 1H), 3.84(s, 2H) |
| 19A | (3-chloro-4-fluorophenyl)methyl | 669.06 | E | E, L | 669.1; 671.1 | 7.39(dd, J=7.1, 2.1Hz, 1H), 7.24(ddd, J=8.5, 4.8, 2.1Hz, 1H), 7.14(dd, J=9.1, 8.5Hz, 1H), 5.53 (d, J=4.6Hz, 1H), 4.99 (s, 2H), 4.23(d, J=7.9 Hz, 1H) |
| 20A | 2-quinolylmethyl | 667.68 | E | F, L | 668.1 | 8.28(d, J=8.5Hz, 1H), 7.98(d, J=8.5Hz, 1H), 7.90(d, J=8.3Hz, 1H), 7.74(m, 1H), 7.57(m, 1H), 7.52(d, J=8.5Hz, 1H), 5.55(d, J=4.6Hz, 1H), 5.33(s, 2H), 4.27(d, J=7.7Hz, 1H) |
| 21A | 2-quinolylmethyl | 667.68 | Z | F, L | 668.1 | 8.32(d, J=8.5Hz, 1H), 8.12(d, J=8.3Hz, 1H), |

TABLE 1-continued

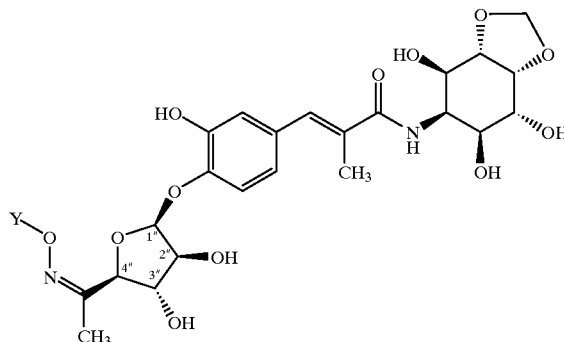

Most of the examples in Table 1 bear the C-4" stereochemistry shown, with the oxime moiety in the beta orientation. Some examples have the oxime in the alpha orientation; this is indicated in the Stereo column

| Ex. | Y | Mol Wt | Stereo | Pro. | Mass spec | 1H NMR peaks (CD₃OD) |
|---|---|---|---|---|---|---|
| | | | | | | 7.92(d, J=8.1Hz, 1H), 7.76(m, 1H), 7.59(m, 1H), 7.53(d, J=8.5Hz, 1H), 5.69(d, J=4.4Hz, 1H), 5.36(AB quartet, Δv=16.4Hz, J=14.8Hz, 2H), 5.28(d, J=6.4Hz, 1H) |
| 22A | (3-chloro-4-fluorophenyl)methyl | 669.06 | Z | E, L | 669.0; 671.0 | 7.46(dd, J=7.3, 2.1Hz, 1H), 7.29(ddd, J=8.3, 4.7, 2.1Hz, 1H), 7.17(m, 1H), 5.64(d, J=4.2Hz, 1H), 5.19(d, J=5.6Hz, 1H), 4.98(AB quartet, Δv = 7.7, J=13.2Hz, 2H) |
| 23A | 3-quinolylmethyl | 667.68 | Z | F, L | 668.1 | 8.84(bd, J=1.9Hz, 1H), 8.30(bs, 1H), 7.99(d, J=8.7Hz, 1H), 7.91(d, J=8.1Hz, 1H), 7.73(m, 1H), 7.58(m, 1H), 5.63(d, J=4.4Hz, 1H), 5.24(m, 3H) |
| 24A | 3-quinolylmethyl | 667.68 | E | F, L | 668.1 | 8.80(bd, J=2.1Hz, 1H), 8.26(bd, J=1.5Hz, 1H), 7.98(d, J=8.5Hz, 1H), 7.89(bd, J=8.3Hz, 1H), 7.73(m, 1H), 7.58(m, 1H), 5.53(d, J=4.6Hz, 1H), 5.27(s, 2H), 4.25(d, J=7.7Hz, 1H) |
| 25A | (4-chloro-3-fluorophenyl)methyl | 669.06 | Z | F, L | 669.1, 671.1 | 7.39(dd, apparent t, J=7.9Hz, 1H), 7.23(m, 1H), 7.14(m, 1H), 5.64(d, J=4.4Hz, 1H), 5.21(d, J=6.4Hz, 1H), 5.00(AB quartet, Δv=7.7Hz, J=13.3Hz, 2H) |
| 26A | (4-chloro-3-fluorophenyl)methyl | 669.06 | E | F, L | 669.1, 671.1 | 7.42(dd, apparent t, J=7.9Hz, 1H), 7.20(dd, J=10.1, 1.8Hz, 1H), 7.14(m, 1H), 5.59(d, J=4.6Hz, 1H), 5.07(s, 2H), 4.28(d, J=7.8Hz, 1H) |
| 27A | (3,4,5-trifluorophenyl)methyl | 670.6 | E | E, L | 671.1 | 7.04(dd, apparent t, J=7.6Hz, 2H), 5.54(d, J=4.6Hz, 1H), 4.99(s, 2H), 4.23(d, J=7.9Hz, 1H) |

TABLE 1-continued

Most of the examples in Table 1 bear the C-4" stereochemistry shown, with the oxime moiety in the beta orientation. Some examples have the oxime in the alpha orientation; this is indicated in the Stereo column

| Ex. | Y | Mol Wt | Stereo | Pro. | Mass spec | 1H NMR peaks (CD$_3$OD) |
|---|---|---|---|---|---|---|
| 28A | (benzodioxole) | 660.64 | Z | F, L | 661.1 | 6.76(m, 3H), 5.92(s, 2H), 5.63(d, J=4.2Hz, 1H), 5.16(d, J=6.4Hz, 1H), 5.00(AB quartet, Δν=9.3 Hz, J=12.5Hz, 2H) |
| 29A | (benzodioxole) | 660.64 | E | F, L | 661.1 | 6.73(m, 3H), 5.89(s, 2H), 5.54(d, J=4.6Hz, 1H), 5.01(s, 2H), 4.24(d, J=7.9Hz, 1H) |
| 30A | (chlorobenzodioxole) | 695.08 | E | F, L | 694.7; 696.4 | [DMSO-d$_6$]6.91(d, J=8.1 Hz, 1H), 6.84(d, J=8.3 Hz, 1H), 6.10(s, 2H), 5.54 (d, J=4.6Hz, 1H), 4.99 (s, 2H), 4.08(d, J=7.9 Hz, 1H) |
| 31A | (chlorobenzodioxole) | 695.08 | Z | F, L | 695.1; 697.1 | 6.96(d, J=8.1Hz, 1H), 6.86(d, J=8.5Hz, 1H), 6.03(s, 2H), 5.65(d, J= 4.2Hz, 1H), 5.18(d, J= 6.4Hz, 1H), 5.05(AB quartet, Δν=15.3Hz, J= 12.5Hz, 2H) |
| 32A | (5-chloro-2-fluoropheny)methyl | 669.06 | Z | F, L | 669.2; 671.2 | 7.44(dd, J=6.3, 2.6Hz, 1H), 7.27(m, 1H), 7.06 (dd, J=9.3, 8.9Hz, 1H), 5.64(d, J=4.2Hz, 1H), 5.20(d, J=6.2Hz, 1H), 5.06(bs, 2H) |
| 33A | (4-fluorophenyl)methyl | 634.62 | E | F, L | 635.2 | 7.31(dd, J=8.9, 5.6Hz, 2H), 7.01(dd, apparent t, J= |

TABLE 1-continued

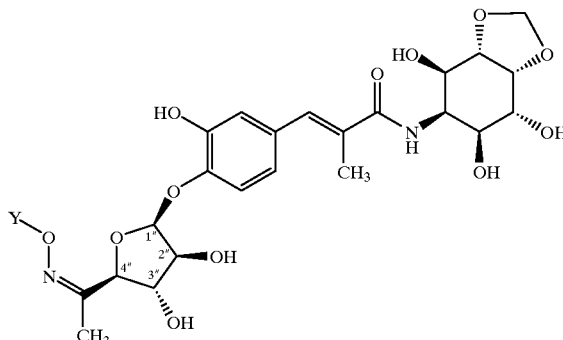

Most of the examples in Table 1 bear the C-4" stereochemistry shown, with the oxime moiety in the beta orientation. Some examples have the oxime in the alpha orientation; this is indicated in the Stereo column

| Ex. | Y | Mol Wt | Stereo | Pro. | Mass spec | 1H NMR peaks (CD$_3$OD) |
|---|---|---|---|---|---|---|
| 34A | (4-phenyl-2-furanyl)methyl | 682.69 | Z | F, L | 683.2 | 8.8Hz, 2H), 5.55(d, J= 4.6Hz, 1H), 5.02(s, 2H), 4.25(d, J=7.9Hz, 1H) 7.87(s, 1H), 7.54(d, J= 7.6Hz, 2H), 7.37(dd, apparent t, J=7.6Hz, 2H), 7.25(t, J=7.3Hz, 1H), 6.80(s, 1H), 5.68(d, J=4.3Hz, 1H), 5.20(d, J= 6.3Hz, 1H), 5.02(AB quartet, Δν=6.1Hz, J= 13.3Hz, 2H) |
| 35A | (4-phenyl-2-furanyl)methyl | 682.69 | E | F, L | 683.2 | 7.86(s, 1H), 7.54(d, J= 8.2Hz, 2H), 7.38(dd, J= 7.9, 6.9Hz, 2H), 7.26(t, J= 6.9Hz, 1H), 6.80(s, 1H), 5.61(d, J=4.6Hz, 1H), 5.05(s, 2H), 4.33(d, J= 7.6Hz, 1H) |
| 36A | ![chroman-2-ylmethyl] | 672.69 | Z | F, L | 673.1 | 7.01(m, 2H), 6.78(m, 2H), 5.65(d, J=4.2Hz, 1H), 5.12(d, J=6.2Hz, 1H), 2.84(m, 1H), 2.75(m, 1H), 2.02(m, 1H), 1.74(m, 1H) |
| 37A | ![chroman-2-ylmethyl] | 672.69 | E; mixture of diastereomers | F, L | 673.1 | 6.97(m, 1H), 6.88(dd, J= 7.9, 2.1Hz, 1H), 6.74(dd, apparent t, J=7.5Hz, 1H), 6.67(m, 1H), 5.55 and 5.54(d, 4.4 and 4.6 Hz, 1H), 4.26 and 4.25(d, J=7.7, 7.9Hz, 1H), 2.79 (m, 1H), 2.71(m, 1H), 1.98 (m, 1H), 1.67(m, 1H) |
| 38A | (3-chloro-2,6-difluorophenyl)methyl | 687.05 | Z | F, L | 687.1; 689.1 | 7.47(m, 1H), 6.70 (apparent bt, J=8.8Hz, 1H), 5.63(d, J=3.9Hz, 1H), 5.12(bs, 2H), 5.11(d, J obscured, 1H) |
| 39A | (3-chloro-2,6-difluorophenyl)methyl | 687.05 | E | F, L | 687.1; 689.1 | 7.44(ddd, apparent td, J= 9, 5Hz, 1H), 6.96(ddd, apparent td, J=8.8, 1.8 Hz, 1H), 5.53(d, J=4.6 Hz, 1H), 5.13(s, 2H), 4.21 (d, J=7.9Hz, 1H) |
| 40A | (2,3,5,6-tetrafluoro-4-methylphenyl)methyl | 702.62 | Z | E, J | 703.1 | 5.61(d, J=4.0Hz, 1H), 5.11(bs, 2H), 5.09(d, J= 6.2Hz, 1H), 2.24(bs, 3H) |

TABLE 1-continued

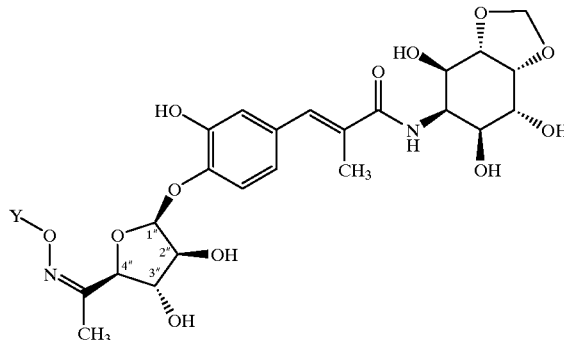

Most of the examples in Table 1 bear the C-4" stereochemistry shown, with the oxime moiety in the beta orientation. Some examples have the oxime in the alpha orientation; this is indicated in the Stereo column

| Ex. | Y | Mol Wt | Stereo | Pro. | Mass spec | 1H NMR peaks (CD$_3$OD) |
|---|---|---|---|---|---|---|
| 41A | (2,3,5,6-tetrafluoro-4-methylphenyl)methyl | 702.62 | E | E, J | 703.1 | 5.52(d, J=4.6Hz, 1H), 5.13(s, 2H), 4.20(d, J= 7.9Hz, 1H), 2.22(t, J=2 Hz, 3H) |
| 42A | (3,4,5-trifluorophenyl)methyl | 670.6 | Z | F, L | 671.1 | 7.14(m, 2H), 5.66(d, J= 4.2Hz, 1H), 5.24(d, J= 6.6Hz, 1H), 4.99(s, 2H) |
| 43A | (2,6-dichlorophenyl)methyl | 685.52 | Z | F, J | 685.0; 687.0 | 7.37(m, 2H), 7.27(dd, J= 8.9, 7.1Hz, 1H), 5.61(d, J= 4.2Hz, 1H), 5.30(AB quartet, Δν=10.1, J= 11.0Hz, 2H), 5.11(d, J= 6.2Hz, 1H) |
| 44A | (2,6-dichlorophenyl)methyl | 685.52 | E | F, J | 685.0; 687.0 | 7.34(m, 2H), 7.24(dd, J= 8.8, 7.2Hz, 1H), 5.54(d, J= 4.6Hz, 1H), 5.32(s, 2H 4.24(d, J=7.9Hz, 1H) |
| 45A | (2,4-dichlorophenyl)methyl | 685.52 | Z | F, L | 685.0; 687.0 | 7.51(d, J=8.2Hz, 1H), 7.47(d, J=2.3Hz, 1H), 7.34(dd, J=8.2, 2.3Hz, 1H), 5.70(d, J=4.3Hz, 1H), 5.29(d, J=6.3Hz, 1H), 5.15(bs, 2H) |
| 46A | (2-chloro-4-fluorophenyl)methyl | 669.06 | Z | F, L | 669.1; 671.1 | 7.54(dd, J=8.6, 6.3Hz, 1H), 7.24(dd, J=8.6, 2.6 Hz, 1H), 7.09(ddd, apparent td, J=8.6, 2.6, 1H), 5.70(d, J=4.3Hz, 1H), 5.28(d, J=6.3Hz, 1H), 5.15(AB quartet, Δν = 6.8Hz, J=13.5Hz, 2H) |
| 47A | (2,4-dichlorophenyl)methyl | 685.52 | E | F, L | 685.1; 687.0 | 7.45(d, J=2.0Hz, 1H), 7.37(d, J=8.2Hz, 1H), 7.29(dd, J=8.6, 2.3Hz, 1H), 5.59(d, J=4.6Hz, 1H), 5.17(s, 2H), 4.29(d, J=7.6Hz, 1H) |
| 48A | (2-chloro-4-fluorophenyl)methyl | 669.06 | E | F, L | 669.1; 671.1 | 7.42(dd, J=8.6, 5.9Hz, 1H), 7.22(dd, J=8.6, 2.6 Hz, 1H), 7.05(ddd, apparent td, J=8.6, 2.6 Hz, 1H), 5.59(d, J=4.6 Hz, 1H), 5.16(s, 2H), 4.29 (d, J=7.9Hz, 1H) |
| 49A | (2-chloro-6-fluorophenyl)methyl | 669.06 | Z | F, J | 669.1; 671.1 | 7.33(ddd, apparent td, J= 8.3, 6.0Hz, 1H), 7.25 (presumed bd, J obscured, 1H), 7.08(bdd, apparent bt, J=8.3Hz, 1H), 5.63 (d, J=4.2Hz, 1H), 5.20 (bs, 2H), 5.12(d, J=6.2 Hz, 1H) |
| 50A | (2-chloro-6-fluorophenyl)methyl | 669.06 | E | F, J | 669.1; 671.1 | 7.31(ddd, apparent td, J= 8.1, 6.0, 1H), 7.22 |

TABLE 1-continued

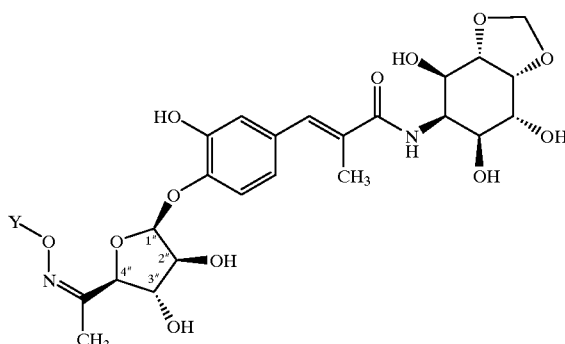

Most of the examples in Table 1 bear the C-4" stereochemistry shown, with the oxime moiety in the beta orientation. Some examples have the oxime in the alpha orientation; this is indicated in the Stereo column

| Ex. | Y | Mol Wt | Stereo | Pro. | Mass spec | 1H NMR peaks (CD$_3$OD) |
|---|---|---|---|---|---|---|
| | | | | | | (presumed bd, J obscured, 1H), 7.05(presumed bt, J= 8.3Hz, 1H), 5.55(d, J= 4.6Hz, 1H), 5.22(s, 2H), 4.25(d, J=7.9Hz, 1H) |
| 51A | (chlorobenzodioxole-methyl) | 695.08 | Z | F, J | 695.1; 697.0 | 6.83(d, J=1.3Hz, 1H), 6.78(d, J=1.4Hz, 1H), 6.00(s, 2H), 5.63(d, J= 4.2Hz, 1H), 5.16(d, J= 6.2Hz, 1H), 4.89(AB quartet, Δv=10.1Hz, J= 12.7Hz, 2H) |
| 52A | (chlorobenzodioxole-methyl) | 695.08 | E | F, J | 695.0; 697.0 | 6.78(d, J=1.4Hz, 1H), 6.72(d, J=1.4Hz, 1H), 5.98(s, 2H), 5.53(d, J= 4.6Hz, 1H), 4.90(s, 2H), 4.24(d, J=7.9Hz, H) |
| 53A | (3-chloro-5-fluorophenyl)methyl | 669.06 | Z | F, L | 669.1; 671.0 | 7.24(bs,1H), 7.12(m, 2H), 5.70(d, J=4.3Hz, 1H), 5.28(d, J=6.6Hz, 1H), 5.06(bs, 2H) |
| 54A | (3-chloro-5-fluorophenyl)methyl | 669.06 | E | F, L | 669.1; 671.1 | 7.18(bs, 1H), 7.11(m, 1H), 7.04(m, 1H), 5.59(d, J=4.6Hz, 1H), 5.08(s, 2H), 4.29(d, J=7.9Hz, 1H) |
| 55A | (2,6-difluorophenyl)methyl | 652.6 | Z | F, L | 653.1 | 7.40(tt, J=8.6, 6.6Hz, 1H), 6.99(dd, apparent t, J= 7.9Hz, 2H), 5.66(d, J= 4.3Hz, 1H), 5.15(m, 3H) |
| 56A | (2,6-difluorophenyl)methyl | 652.6 | E | F, L | 653.1 | 7.39(tt, J=8.6, 6.3Hz, 1H), 6.87(dd, apparent t, J= 7.6Hz, 2H), 5.58(d, J= 4.6Hz, 1H), 5.17(s, 2H), 4.28(d, J=7.9Hz, 1H) |
| 57A | (3,4-difluorophenyl)methyl | 652.61 | Z | F, L | 653.1 | 7.31(m, 1H), 7.23(m, 1H), 7.15(m, 1H), 5.69(d, J= 4.0Hz, 1H), 5.25(d, J= 6.3Hz, 1H), 5.03(bs, 2H) |
| 58A | (3,4- | 652.61 | E | F, L | 653.1 | 7.24(m, 1H), 7.20(dd, J= |

TABLE 1-continued

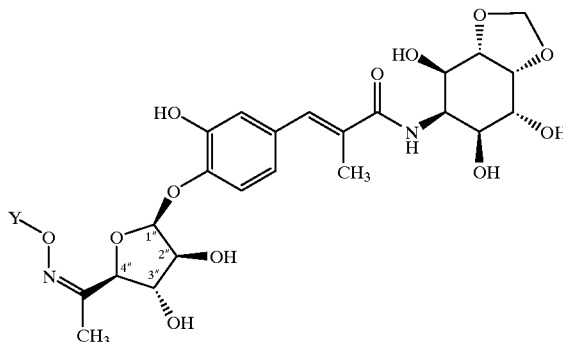

Most of the examples in Table 1 bear the C-4" stereochemistry shown, with the oxime moiety in the beta orientation. Some examples have the oxime in the alpha orientation; this is indicated in the Stereo column

| Ex. | Y | Mol Wt | Stereo | Pro. | Mass spec | 1H NMR peaks (CD$_3$OD) |
|---|---|---|---|---|---|---|
|  | difluorophenyl)methyl |  |  |  |  | 10.7, 8.0Hz, 1H), 7.14(m, 1H), 5.59(d, J=4.3Hz, 1H), 5.05(s, 2H), 4.28(d, J=7.9Hz, 1H) |
| 59A | (2,3,6-trifluorophenyl)methyl | 670.6 | Z | F, L | 671.1 | 7.25(m, 1H), 6.94(m, 1H), 5.61(d, J=4.2Hz, 1H), 5.11(AB quartet, Δv=6.3 Hz, J=9.8Hz, 2H), 5.10 (d, J=6.4Hz, 1H) |
| 60A | (2,3,6-trifluorophenyl)methyl | 670.6 | E | F, L | 671.0 | 7.26(m, 1H), 6.94(m, 1H), 5.55(d, J=4.6Hz, 1H), 5.15(s, 2H), 4.23(d, J=7.9Hz, 1H) |
| 61A | (2,4-difluorophenyl)methyl | 652.61 | Z | F, L | 653.2 | 7.50(m, 1H), 6.95(m, 2H), 5.68(d, J=4.0Hz, 1H), 5.22(d, J=6.3Hz, 1H), 5.09(bs, 2H) |
| 62A | (2,4-difluorophenyl)methyl | 652.61 | E | F, L | 653.2 | 7.39(m, 1H), 6.91(m, 2H), 5.58(d, J=4.6Hz, 1H), 5.09(s, 2H), 4.30(d, J=7.9Hz, 1H) |
| 63A | (2,6-difluoro-4-methylphenyl)methyl | 666.64 | Z | F, L | 667.1 | 6.77(d, J=8.1Hz, 2H), 5.60(d, J=4.2Hz, 1H), 5.08(d, J=6.2Hz, 1H), 5.04(bs, 2H), 2.32(s, 3H) |
| 64A | (2,6-difluoro-4-methylphenyl)methyl | 666.64 | E | F, L | 667.1 | 6.75(d, J=8.1Hz, 2H), 5.52(d, J=4.6Hz, 1H), 5.06(s, 2H), 4.22(d, J=7.9Hz, 1H), 2.30(s, 3H) |
| 65A | (2,3,4,5,6-pentafluorophenyl)methyl | 706.58 | Z | F, L | 707.1 | 5.62(d, J=4.0Hz, 1H), 5.11(bs, 2H), 5.08(d, J=6.2Hz, 1H) |
| 66A | (2-fluoro-6-trifluoromethylphenyl)methyl) | 702.62 | Z | F, L | 703.1 | 7.54(m, 2H), 7.40(m, 1H), 5.60(d, J=4.2Hz, 1H), 5.20(AB quartet, Δv=15.4Hz, J=11.5Hz, 2H), 5.07(d, J=6.4Hz, 1H) |
| 67A | (2-fluoro-6-trifluoromethylphenyl)methyl) | 702.62 | E | F, L | 703.1 | 7.54(m, 2H), 7.40(m, 1H), 5.55(d, J=4.6Hz, 1H), 5.24(s, 2H), 4.25(d, J=7.9Hz, 1H) |
| 68A | (2,3-difluorophenyl)methyl | 652.61 | Z | F, L | 653.1 | 7.25(m, 1H), 7.17(m, 2H), 5.69(d, J=4.0Hz, 1H), 5.24(presumed d, J obscured, 1H), 5.16(bs, 2H) |
| 69A | (2,3-difluorophenyl)methyl | 652.61 | E | F, L | 653.1 | 7.16(m, 3H), 5.59(d, J=4.6Hz, 1H), 5.17(bs, 2H), 4.28(d, J=7.9Hz, 1H) |
| 70A | (2,3,4-trifluorophenyl)methyl | 670.6 | E | F, L | 671.1 | 7.17(m, 1H), 7.03(m, 1H), 5.53(d, J=4.6Hz, 1H), 5.08(s, 2H), 4.22(d, J=7.7Hz, 1H) |
| 71A | (2,3,4- | 670.6 | Z | F, L | 671.1 | 7.22(m, 1H), 7.09(m, 1H), |

TABLE 1-continued

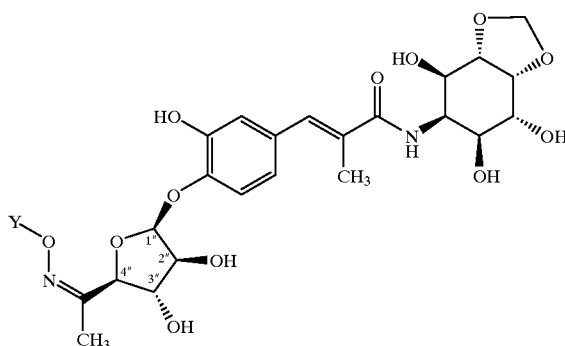

Most of the examples in Table 1 bear the C-4" stereochemistry shown, with the oxime moiety in the beta orientation. Some examples have the oxime in the alpha orientation; this is indicated in the Stereo column

| Ex. | Y | Mol Wt | Stereo | Pro. | Mass spec | 1H NMR peaks (CD$_3$OD) |
|---|---|---|---|---|---|---|
|  | trifluorophenyl)methyl |  |  |  |  | 5.65(d, J=4.2Hz, 1H), 5.18(d, J=6.2Hz, 1H), 5.08(bs, 2H) |
| 72A | (2,3,5,6-tetrafluorophenyl)methyl | 688.59 | Z | F, L | 688.9 | 7.27(m, 1H), 5.69(d, J=4.0Hz, 1H), 5.24(d, J=6.6Hz, 1H), 5.12(bs, 2H) |
| 73A | (2,3,5,6-tetrafluorophenyl)methyl | 688.59 | E | F, L | 689.0 | 7.17(m, 1H), 5.58(d, J=4.3Hz, 1H), 5.13(bs, 2H), 4.27(d, J=7.6Hz, 1H) |
| 74A | 2,3-difluoro-6-methoxyphenyl)methyl | 682.64 | E | F, L | 683.0 | 7.20(m, 1H), 6.76(ddd, J=9.2, 3.6, 2.3Hz, 1H), 5.58(d, J=4.6Hz, 1H), 5.16(d, J=2.0Hz, 2H), 4.28(d, J=7.9Hz, 1H), 3.83(s, 3H) |
| 75A | 2,3-difluoro-6-methoxyphenyl)methyl | 682.64 | Z | F, L | 683.0 | 7.22(m, 1H), 6.80(ddd, J=9.2, 3.3, 2.0, 1H), 5.65 (d, J=3.6Hz, 1H), 5.14 (m, 2H), 5.09(d, J=5.6 Hz, 1H), 3.88(s, 3H) |
| 76A | (4-chloro-3-sulfonamidophenyl)methyl | 730.15 | E | F, L | 730.0 | 8.21(m, 1H), 7.90(m, 1H), 7.52(m, 1H), 5.58(d, J=4.6Hz, 1H), 5.13(s, 2H), 4.28(d, J=7.9Hz, 1H) |
| 77A | (2-fluoro-6-trifluoromethoxyphenyl)methyl | 718.616 | E | F, L | 719.0 | 7.48(ddd, apparent td, J=8.2, 6.3Hz, 1H), 7.18(m, 2H), 5.58(d, J=4.3Hz, 1H), 5.19(d, J=1.0Hz, 2H), 4.27(d, J=7.9Hz, 1H) |
| 78A | (24-fluoro-6-trifluoromethoxyphenyl)methyl | 718.616 | Z | F, L | 719.0 | 7.49(ddd, apparent t, J=8.6, 6.3Hz, 1H), 7.19(m, 2H), 5.65(d, J=4.3Hz, 1H), 5.16(bs, 2H), 5.14(d, J=6.3Hz, 1H) |
| 79A | 3-chloro-4-fluorophenyl | 655.04 | E | E, J | 654.8 | 7.28(dd, J=6.2, 2.7Hz, 1H), 7.11(dd, apparent t, J=9Hz, 1H), 7.02(m, 1H), 5.65(d, J=4.4Hz, 1H), 4.28(dd, J=8.3, 4.6Hz, 1H) |
| 80A | (2-fluoro-6-methoxyphenyl)methyl | 664.65 | E | F, L | 665.1 | 7.26(ddd, apparent td, J=8.5, 6.9Hz, 1H), 6.76(d, J=8.5Hz, 1H), 6.65(dd, apparent t, J=8.5Hz, 1H), 5.53(d, J=4.6Hz, 1H), 5.09(d, J=1.4Hz, 2H), 4.24(d, J=7.9Hz, 1H), 3.79(s, 3H) |
| 81A | 4-(methoxycarbonyl)phenyl | 660.64 | E | E, J | 661.1 | 7.88(d, J=8.5Hz, 2H), 7.12(d, J=8.5Hz, 2H), 5.65(d, J=4.4Hz, 1H), 4.29(dd, J=8.1, 5Hz, 1H), 3.84(s, 3H) |

TABLE 1-continued

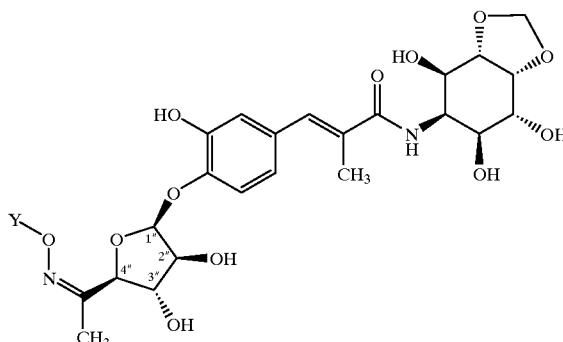

Most of the examples in Table 1 bear the C-4" stereochemistry shown, with the oxime moiety in the beta orientation. Some examples have the oxime in the alpha orientation; this is indicated in the Stereo column

| Ex. | Y | Mol Wt | Stereo | Pro. | Mass spec | 1H NMR peaks (CD$_3$OD) |
|---|---|---|---|---|---|---|
| 82A | 3-chlorophenyl | 637.04 | E | E, J | 637.3; 639.4 | 7.19(dd, apparent t, J=8.2Hz, 1H), 7.18(dd, apparent t, J=2.2Hz, 1H), 6.99(ddd, J=8.3, 2.3, 1.0Hz, 1H), 6.95 (ddd, J=8.1, 1.9, 1.0Hz, 1H), 5.62(d, J=4.6Hz, 1H), 4.25(dd, J=8.1, 4.6 Hz, 1H) |
| 83A | 2-fluorophenyl | 620.58 | E | E, J | 621.0 | 7.34(ddd, apparent td, J=8.1, 1.7Hz, 1H), 7.05(m, 1H), 7.00(m, 1H), 6.94(m, 1H), 5.62(d, J=4.6Hz, 1H), 4.26(dd, J=8.2, 4.7 Hz, 1H) |
| 84A | 3,5-dichlorophenyl | 671.49 | E | E, J | 670.7; 673.2 | 7.14(d, J=1.9Hz, 2H), 7.04(bs, 1H), 5.65(d J=4.4Hz, 1H), 4.29(dd, J=8.1, 4.6Hz, 1H) |
| 85A | (3-chloro-2-thienyl)methyl | 657.098 | Z | F, L | 656.8; 658.9 | 7.46(d, J=5.3Hz, 1H), 6.95(d, J=5.3Hz, 1H), 5.68(d, J=4.3Hz, 1H), 5.19(m, 2H), 5.17(d, J=6.3Hz, 1H) |
| 86A | (3-chloro-2-thienyl)methyl | 657.098 | E | F, L | 656.9; 658.9 | 7.43(d, J=5.3Hz, 1H), 6.93(d, J=5.3Hz, 1H), 5.59(d, J=4.6Hz, 1H), 5.20(s, 2H), 4.31(d, J=7.6Hz, 1H) |
| 87A | (2-thienyl)methyl | 622.653 | Z | F, L | 622.9 | 7.38(dd, J=5.3, 1.3Hz, 1H), 7.08(bd, J=3.6Hz, 1H), 6.99(dd, J=5.3, 3.6 Hz, 1H), 5.67(d, J=4.3 Hz, 1H), 5.20(bs, 2H), 5.16(d, J=6.3Hz, 1H) |
| 88A | (2-thienyl)methyl | 622.653 | E | F, L | 622.9 | 7.35(dd, J=5.3, 1.3Hz, 1H), 7.05(bd, J=3.3Hz, 1H), 6.97(dd, J=4.9, 3.3 Hz, 1H), 5.59(d, J=4.6 Hz, 1H), 5.22(s, 2H), 4.31 (d, J=7.9Hz, 1H) |
| 89A | (2-chloro-6-trifluoromethoxyphenyl)methyl | 735.07 | Z | F, L | 734.8; 737.0 | 7.46(m, 2H), 7.33(m, 1H), 5.66(d, J=4.3Hz, 1H), 5.25(AB quartet, Δv=4.9 Hz, J=11.5Hz, 2H), 5.14 (d, J=6.3Hz, 1H) |
| 90A | (2-choro-6-trifluoromethoxyphenyl)methyl | 735.07 | E | F, L | 734.8; 736.9 | 7.45(m, 2H), 7.31(m, 1H), 5.58(d, J=4.3Hz, 1H), 5.28(s, 2H), 4.28(d, J=7.9Hz, 1H) |
| 91A | (5-chloro-2-thienyl)methyl | 657.098 | Z | F, L | 656.9; 658.9 | 6.89(d, J=4.0Hz, 1H), 6.85(d, J=4.0Hz, 1H), 5.68(d, J=4.0Hz, 1H), 5.15(d, J=6.3Hz, 1H), |

TABLE 1-continued

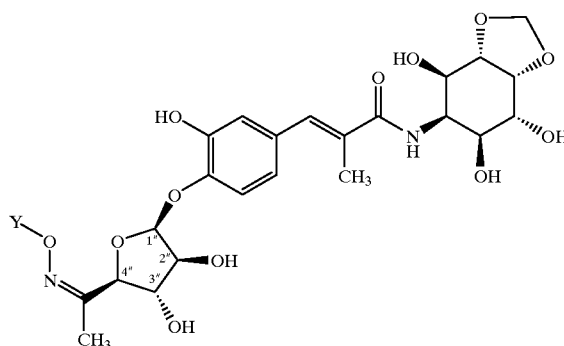

Most of the examples in Table 1 bear the C-4" stereochemistry shown, with the oxime moiety in the beta orientation. Some examples have the oxime in the alpha orientation; this is indicated in the Stereo column

| Ex. | Y | Mol Wt | Stereo | Pro. | Mass spec | 1H NMR peaks (CD$_3$OD) |
|---|---|---|---|---|---|---|
| 92A | (5-chloro-2-thienyl)methyl | 657.098 | E | F, L | 656.9; 658.9 | 5.10(s, 2H) 6.86(bd, J=3.6Hz, 1H), 6.82(bd, J=3.6Hz, 1H), 5.59(d, J=4.3Hz, 1H), 5.12(s, 2H), 4.31(d, J=7.2Hz, 1H) |
| 93A | (2-difluoromethoxyphenyl)methyl | 682.635 | Z | F, L | 683.1 | 7.49(bd, J=7.7Hz, 1H), 7.33(dd, apparent bt, J=8Hz, 1H), 7.22(dd, apparent bt, J=7.5Hz, 1H), 7.16(bd, J=8Hz, 1H), 6.79(t, J=74.4Hz, 1H), 5.65(d, J=4.2Hz, 1H), 5.22(d, J=6.4Hz, 1H), 5.11(AB quartet, Δv = 9.2Hz, J=13.2Hz, 2H) |
| 94A | (2-difluoromethoxyphenyl)methyl | 682.635 | E | F, L | 683.1 | 7.37(d, J=7.1Hz, 1H), 7.29(dd, apparent bt, J=7Hz, 1H), 7.16(dd, apparent bt, J=7.5Hz, 1H), 7.10(m, 1H), 6.72(t, J=74Hz, 1H), 5.54(d, J=4.4Hz, 1H), 5.11(s, 2H), 4.24(d, J=7.9Hz, 1H) |
| 95A | (3-fluorophenyl)methyl | 634.618 | E; α-steroechem at 4" | F; N-1 | 634.9 | 7.36(ddd, apparent td, J=7.9, 5.9Hz, 1H), 7.18(m, 1H), 7.10(m, 1H), 7.02(m, 1H), 5.73(d, J=4.3Hz, 1H), 5.12(s, 2H), 4.79(d, J=6.9Hz, 1H) |
| 96A | (3-chlorophenyl)methyl | 651.073 | E; α-steroechem at 4" | F; N-1 | 650.8 | 7.32(bs, 1H), 7.27(m, 3H), 5.68(d, J=4.4Hz, 1H), 5.05(s, 2H), 4.74(d, J=7.1Hz, 1H) |
| 97A | (3,4-dichlorophenyl)methyl | 685.518 | E | F, L | 684.9; 686.9 | 7.42(m, 2H), 7.20(dd, J=8.3, 2.1Hz, 1H), 5.53(d, J=4.6Hz, 1H), 5.00(s, 2H), 4.23(d, J=7.9Hz, 1H) |
| 98A | (2,6-dimethylphenyl)methyl | 644.682 | Z | F, L | 644.9 | 7.05(dd, J=8.3, 6.4Hz, 1H) 6.97(bd, J=7.5Hz, 2H), 5.59(d, J=4.4Hz, 1H), 5.11(AB quartet, Δv = 18.3Hz, J=10.9Hz, 2H), 5.09(d, J=6.4Hz, 1H), 2.37(s, 6H) |
| 99A | (2,6-dimethylphenyl)methyl | 644.682 | E | F, L | 645.1 | 7.03(dd, J=8.1, 6.4Hz, 1H), 6.95(bd, J=7.3, 2H), 5.54(d, J=4.6Hz, 1H), 5.13(s, 2H), 4.25(d, J=7.7Hz, 1H), 2.33(s, 6H) |
| 100A | (3-fluorophenyl)methyl | 634.618 | Z; α-steroechem at 4" | F; N-1 | 635.1 | 7.36(ddd, apparent td, J=7.9, 5.6Hz, 1H), 7.16(m, 1H), 7.13(m, 1H), 7.02(bt, J=8.9Hz, 1H), 5.80(d, J= |

TABLE 1-continued

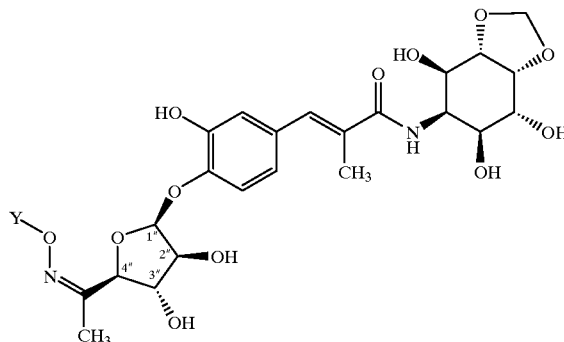

Most of the examples in Table 1 bear the C-4" stereochemistry shown, with the oxime moiety in the beta orientation. Some examples have the oxime in the alpha orientation; this is indicated in the Stereo column

| Ex. | Y | Mol Wt | Stereo | Pro. | Mass spec | 1H NMR peaks (CD₃OD) |
|---|---|---|---|---|---|---|
| 101A | (3-chlorophenyl)methyl | 651.073 | Z; α-steroechem at 4" | F; N-1 | 650.9; 653.0 | 4.0Hz, 1H), 5.51(d, J=4.9Hz, 1H), 5.07(AB quartet, Δv=11.8Hz, J=12.8Hz, 1H) 7.40(bs, 1H), 7.29(m, 3H), 5.80(d, J=4.0Hz, 1H), 5.50(d, J=5.3Hz, 1H), 5.06(AB quartet, Δv = 11.89Hz, J=12.8Hz, 2H) |
| 102A | [chroman-4-yl, 6-Cl] | 693.11 | Z | E, J | 693.1; 695.1 | 7.37(d, J=2.7Hz, 1H), 7.14(dd, J=8.7, 2.7Hz, 1H), 6.76(d, J=8.7Hz, 1H), 5.63(d, J=4.4Hz, 1H), 5.16(d, J=6.6Hz, 1H), 5.05(m, 1H), 2.21(m, 1H), 2.04(m, 1H) |
| 103A | [chroman-4-yl, 6-Cl] | 693.11 | E; mixture of diastereomers | E, J | 693.1; 695.1 | 7.24(m, 1H), 7.11(m, 1H), 6.73(d, J=8.9Hz, 1H), 5.58 and 5.57(d, J=4.2 and 4.2Hz, 1H), 5.04(m, 1H), 4.31 and 4.30(d, J=7.7 and 7.7Hz, 1H), 4.02 (m, 1H), 2.21(m, 1H), 2.00 (m, 1H) |
| 104A | (4-phenyl-2-thiazolyl)methyl | 699.74 | Z | G, L | 700.2 | 7.87(m, 2H), 7.74(br s, 1H), 7.38(m, 2H), 7.30(m, 1H), 5.85(d, J=4.4, 1H), 5.83(br s, 2H), 5.22(d, J=6.2Hz, 1H) |
| 105A | (4-phenyl-2-thiazolyl)methyl | 699.74 | E | G, L | 700.2 | 7.82(m, 2H), 7.67(br s, 1H), 7.36(m, 2H), 7.27(m, 1H), 5.55(d, J=4.6, 1H), 5.84(br s, 2H), |
| 106A | 1-(2,4-difluorophenyl)propyl | 680.66 | Z; mixture of diastereomers | G, L | 681.0 | 7.48 and 7.32(2m, 1H), 6.85(m, 2H), 5.65(m, 1H), 5.32 and 5.26(2d, J=6.4 and 6.2Hz, 1H), 5.20(m, 1H), 1.86 and 1.74(2m, 2H), 0.89(m, 3H). |
| 107A | 1-(2,4-difluorophenyl)propyl | 680.66 | E; mixture of diastereomers | G, L | 681.0 | 7.25(m, 1H), 6.83(m, 2H), 5.52 and 5.51(2d, J=4.5 and 4.5Hz, 1H), 5.23(m, 1H), 1.86 and 1.72(2m, 2H), 0.86(m, 3H). |
| 108A | 1-(3,4-difluorophenyl)ethyl | 666.64 | Z; mixture of | G, L | 667.0, 689.0 | 7.28(m, 1H), 7.15(m, 1H), 5.64(d, J 4.2Hz, 1H), 5.29 (d, J=6.6Hz, 1H), 5.09 |

TABLE 1-continued

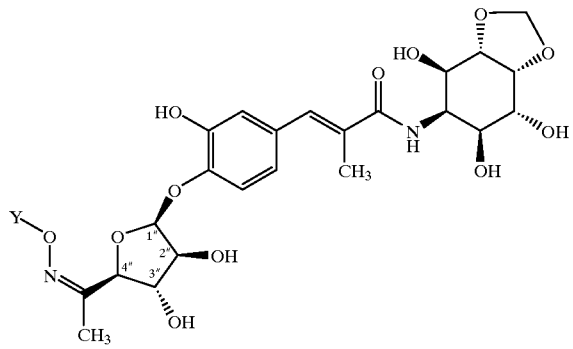

Most of the examples in Table 1 bear the C-4" stereochemistry shown, with the oxime moiety in the beta orientation. Some examples have the oxime in the alpha orientation; this is indicated in the Stereo column

| Ex. | Y | Mol Wt | Stereo | Pro. | Mass spec | 1H NMR peaks (CD$_3$OD) |
|---|---|---|---|---|---|---|
| | | | diastereomers | | | (q, J=6.6Hz, 1H), 1.43 (d, J=6.6Hz, 3H). |
| 109A | 1-(3,4-difluorophenyl)ethyl | 666.64 | E; mixture of diastereomers | G, L | 667.0, 689.0 | 7.13(m, 3H), 5.52(m, 1H), 5.14(m, 1H), 1.43 and 1.42(2d, J=6.4 and 6.6 Hz, 3H). |
| 110A | 1-(2,4-difluorophenyl)ethyl | 666.64 | Z; mixture of diastereomers | G, L | 667.1 | 7.51 and 7.37(m, 1H), 8.85(m, 1H), 5.65(m, 1H), 5.38(m, 1H), 5.30 and 5.24(2d, J=6.6 and 6.4 Hz, 1H), 1.45 and 1.44(2d, J=6.6 and 6.6Hz, 3H). |
| 111A | 1-(2,4-difluorophenyl)ethyl | 666.64 | E; mixture of diastereomers | G, L | 667.1 | 7.29(m, 1H), 6.85(m, 2H), 5.52(m, 1H), 5.40(m, 1H), 1.47 and 1.46(2d, J= 6.6 and 6.6Hz, 3H) |
| 112A | 1-(3,5-difluorophenyl)ethyl | 666.64 | Z; mixture of diastereomers | G, L | 667.0 | 6/97(m, 2H), 6.76(m, 1H), 5.65(d, J 4.2Hz, 1H), 5.30 (d, J 6.6Hz, 1H), 5.10(q, J=6.6Hz, 1H), 1.4(d, J= 6.6Hz, 3H). |
| 113A | 1-(3,5-difluorophenyl)ethyl | 666.64 | E; mixture of diastereomers | G, L | 667.0 | 6.83(m., 2H), 6.75(m, 1H), 5.52(2d, J=4.8 and 4.6Hz, 1H), 5.15(m, 1H), 1.43 and 1.42(2d, J=6.6 and 6.6Hz, 3H) |
| 114A | 1-(3-chloro-2,6-difluorophenyl)ethyl | 701.081 | Z; mixture of diastereomers | G, L | 701.0, 703.0 | 7.39(m, 1H), 6.94(m, 1H), 5.64(br d, J=3.9Hz, 1H), 5.49(q, 6.8Hz), 5.18(m, 1H), 1.60(d, 6.9Hz). |
| 115A | 1-(3-chloro-2,6-difluorophenyl)ethyl | 701.081 | E; mixture of diastereomers | G, L | 701.0, 703.0 | 7.35(m, 1H), 6.89(m, 1H), 5.58(m, 1H), 5.49(m, 1H), 1.56 and 1.55(2d, J=6.8 and 6.8Hz, 3H). |
| 116A | 1-(3-chlorophenyl)ethyl | 665.10 | E | E, L | 665.1, 667.1 | 7.25(m, 1H), 7.20(m, 1H), 5.54 and 5.53(2d, J=4.8 and 4.8Hz, 1H), 5.17(m, 1H), 1.47 and 1.45(2d, J= 6.2 and 6.6Hz, 3H). |

TABLE 2

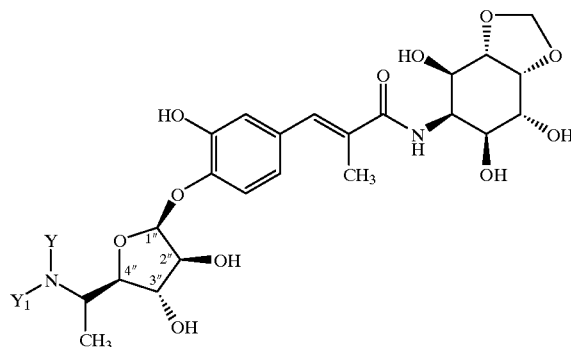

In the examples below for Table 2, $Y^1$ is H for all examples except Example 97 where it is methyl.

| Ex. | Y | Mol Wt | Pro. | Mass spec. | 1H NMR peaks(CD$_3$OD) |
|---|---|---|---|---|---|
| 93 | phenylmethyl | 602.64 | O | 603.2 | 7.17(m, 3H), 7.08(m, 2H), 5.53(d, J=4.6Hz, 1H), 3.87(dd, J=7.5, 4.4Hz, 1H), 3.79(d, J=13.1Hz, 1H), 3.61(d, J=13.1Hz, 1H), 2.90(m, 1H), 1.09(d, J=6.6Hz, 3H) |
| 94 | (3,4-dimethoxyphenyl)-methyl | 662.7 | O | 663.3 | 7.07(s, 1H), 6.92(m, 2H), 5.61(d, J=3.7Hz, 1H), 4.07(right half of AB quartet; left hand signal obscured, J=13.1Hz, 1H), 3.80(s, 3H), 3.79(s, 3H), 3.41(m, 1H), 1.26(d, J=6.9Hz, 3H) |
| 95 | [2-(trifluoromethyl)phenyl]methyl | 670.64 | P | 671.2 | 7.56(bd, J=7.9Hz, 1H), 7.41(m, 2H), 7.33(bt, J=7.5Hz, 1H), 5.53(d, J=4.6Hz, 1H), 3.87(dd, J=7.5, 4.4Hz, 1H), 2.92(m, 1H), 1.09(d, J=6.6Hz, 3H) |
| 96 | (4-tert-butylphenyl)methyl | 658.75 | P | 659.3 | 7.20(d, J=8.3Hz, 2H), 6.97(d, J=8.3Hz, 2H), 5.51(d, J=4.6Hz, 1H), 3.84(dd, J=7.5, 4.4Hz, 1H), 3.73(d, J=13.1Hz, 1H), 3.55(d, J=13.1Hz, 1H), 2.86(m, 1H), 1.24(s, 9H), 1.07(d, J=6.4Hz, 3H) |
| 97 | phenylmethyl | 616.67 | Q (using the product of Example 93 as starting material) | 617.2 | 7.30(m, 5H), 5.55(d, J=3.9Hz, 1H), 4.04(dd, J=7.1, 4.9Hz, 1H), 3.54(AB quartet, Δv=49.0Hz, J=13.2Hz, 2H), 2.88(m, 1H), 2.16(s, 3H), 0.91(d, J=6.6Hz, 3H) |
| 98 | phenyl | 588.62 | R | 589.2 | 7.02(dd, J=8.6, 7.4Hz, 2H), 6.58(dd, J =8.7, 1.0 Hz, 2H), 6.54(dd, J=7.3, 1.0Hz, 1H), 5.57(d, J=4.4Hz, 1H), 3.86(dd, J=6.8, 5.4Hz, 1H), 3.59(m, 1H), 1.04(d, J=6.4Hz, 3H) |
| 99 | 2-phenylethyl | 616.67 | P | 617.3 | 7.19(m, 2H), 7.08(m, 3H), 5.52(d, J =4.4Hz, 1H), 3.87(dd, J=7.2, 3.8Hz, 1H), 2.88(m, 3H), 2.67(m, 2H), 1.03(d, J=6.4Hz, 3H) |
| 100 | 4-fluorophenyl | 606.61 | R | 607.2 | 6.76(dd, apparent t, J= |

TABLE 2-continued

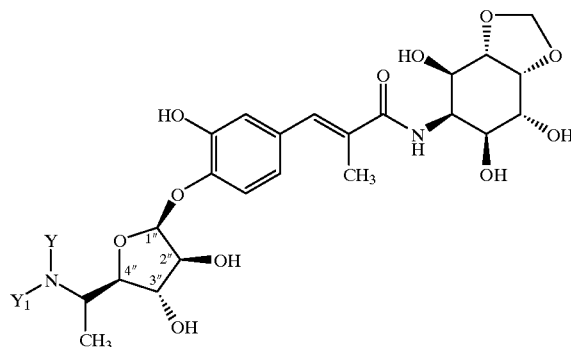

In the examples below for Table 2, $Y^1$ is H for all examples except Example 97 where it is methyl.

| Ex. | Y | Mol Wt | Pro. | Mass spec. | 1H NMR peaks(CD$_3$OD) |
|---|---|---|---|---|---|
| 101 | 2-(4-chorophenyl)ethyl | 651.12 | P | 651.2; 653.2 | 8.8Hz, 2H), 6.56(dd, J=9.0, 4.5Hz, 2H), 5.58(d, J=4.4Hz, 1H), 3.53(m, 1H), 1.04(d, J=6.4Hz, 3H) 7.19(d, J=8.3Hz, 2H), 7.08(d, J =8.3Hz, 2H), 5.53(d, J=4.4Hz, 1H), 2.9(m, 3H), 2.7(m, 2H), 1.07(d, J=6.4Hz, 3H) |

TABLE 3

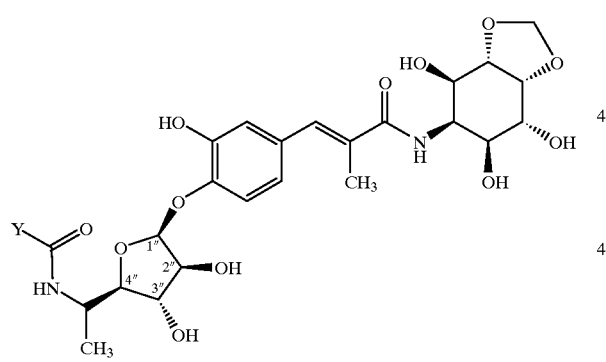

| Ex. | Y | Mol wt | Pro. | Mass spec | 1H NMR peaks (CD$_3$OD) |
|---|---|---|---|---|---|
| 102 | phenylmethyl | 630.67 | S | 631.1 | 7.22(m, 5H), 5.50(d, J=4.4Hz, 1H), 3.39(left half of AB quartet, right half obscured, J=14.3Hz, 1H), 1.03(d, J=6.6Hz, 3H) |
| 103 | cyclopropyl | 580.59 | S | 581.3 | 5.56(d, J=3.7Hz, 1H), 1.47(m, 1H), 1.06(d, J=6.6Hz, 3H), 0.69(m, 2H), 0.56(m, 2H) |

TABLE 3-continued

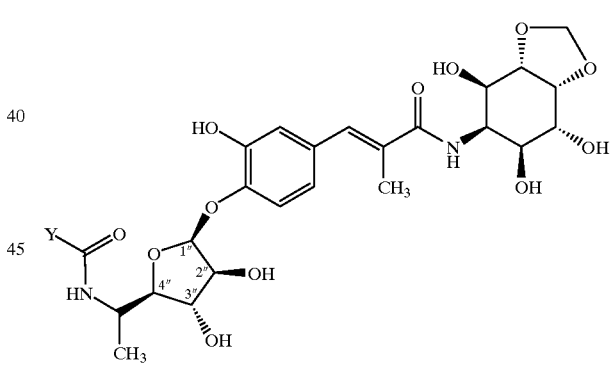

| Ex. | Y | Mol wt | Pro. | Mass spec | 1H NMR peaks (CD$_3$OD) |
|---|---|---|---|---|---|
| 104 | (1,3-benzodioxol-5-yl) | 660.64 | T | 661.3 | 7.29(dd, J=8.1, 1.9Hz, 1H), 7.21(bs, 1H), 6.78 (d, J=8.1Hz, 1H), 5.97(s, 2H), 5.50(d, J=4.6Hz, 1H), 4.29(m, 1H), 3.86(dd, apparent t, J=6.9Hz, 1H), 1.18(d, J=6.8Hz, 3H) |

TABLE 4

| Ex. | Y | Mol Wt | Pro. | Mass Spec | 1H NMR peaks (CD₃OD) |
|---|---|---|---|---|---|
| 105 | phenylmethyl | 603.63 | U | 604.1 | 7.25(br s, 1H), 7.2–7.13(m, 6H), 6.92(d, J=1.3Hz, 1H), 6.84(dd, J=8.5 and 1.9Hz, 1H), 5.56(d, J=3.7Hz, 1H), 4.42(AB quartet, Δv=16Hz, J=11.8Hz, 2H), 2.08(d, J=1.5Hz, 3H), 1.16(d, J=6.4Hz, 3H). |
| 106 | (3,4-dichloro-phenyl)methyl | 672.52 | U | 672.1, 674.1 | 7.30–7.26(m, 2H); 7.22(s, 1H); 7.13(d, J=8.5Hz, 1H); 7.03(dd, J=8.3 and 2.0Hz, 1H); 6.89(d, J=2Hz, 1H); 6.85(dd, J=8.5, 1.9Hz, 1H); 5.56(br dd, 1H); 4.34(AB quartet, Δv=34.7Hz, J=12.7Hz, 12H), 2.05(d, J=1.5Hz, 3H); 1.16,(d, J=6.2Hz, 1H). |
| 107 | (4-fluorophenyl)methyl | 621.62 | U | 622.2 | 7.22(br s, 1H), 7.16–7.12(m, 3H), 6.90–6.81(m, 4H), 5.54(d, J=4.0Hz, 1H), 4.38(AB quartet, Δv=25.1Hz, J=11.7Hz, 2H), 2.06(d, J=1.4Hz, 3H), 1.14(d, J=6.2Hz) |
| 108 | (4-methyl-phenyl)methyl | 617.66 | U | 618.3 | 7.25(s, 1H), 7.17(d, J=8.3Hz, 1H), 7.04–6.99(m, 4H), 6.93(d, J=1.8Hz, 1H), 6.84(dd, J=8.5 and 2.1Hz, 1H), 5.55(d, J=3.9Hz, 1H), 4.37(AB quartet, Δv=16.0Hz, J=11.7Hz, 2H), 2.25(s, 3H), 2.08 (d, J=2.2Hz, 3H), 1.15(d, J=6.2Hz, 3H) |
| 109 | (3-fluorophenyl)methyl | 621.62 | U | 622 | 7.22(d, J=5.4Hz, 1H), 7.2–7.16 (m, 1H) 7.16(d, J=8.5Hz, 1H), 6.94–6.89(m, 4H), 6.82(dd, J=8.3 and 1.9Hz, 1H), 5.57(d, J=3.5Hz, 1H), 4.41(AB quartet, Δv=20.1Hz, J=12.5Hz, 2H), 2.08(d, J=1.7Hz, 3H), 1.18(d, J=6.4Hz). |
| 110 | (1,3-benzodioxol-5-yl)methyl | 647.64 | V | 648.1 | 7.24(brs, 1H), 7.15(d, J=8.3Hz, 1Hz), 6.92(d, J=2.0Hz, 1H), 6.84 (dd, J=8.4 and 2.0Hz, 1H), 6.65–6.59 (m, 3H), 5.86,(s, 2H), 5.54(d, J=3.5Hz, 1H), 4.30(AB quartet, Δv=23.6Hz, J=11.5Hz, 2H), 2.08(d, J=1.3Hz, 3H), 1.14(d, J=6.4Hz, 3H). |
| 111 | (phenylmethyl)oxy-methyl | 633.66 | Z | 634.2 | 7.28–7.18(m, 5H), 7.11(d, J=8.5 Hz, 1H), 6.90(d, J=2.1Hz, 1H) 6.78(dd, J=8.5 and 2.1Hz, 1H), 5.54(d, J=4.2Hz, 1H), 4.66(AB quartet, Δv=57.9, J=6.8Hz, 2H), 4.43(AB quartet, Δv=19.8Hz, J=11.9Hz, 2H), 1.20(d, J=6.2Hz, 3H). |
| 112 | (4-chloro-phenyl)methyl | 638 | U | 638.1, 640.1 | 7.25(s, 1H), 7.19–7.11(m, 4H), 6.92(s, 1H), 6.84(dd, J=8.5 and |

TABLE 4-continued

| Ex. | Y | Mol Wt | Pro. | Mass Spec | 1H NMR peaks (CD$_3$OD) |
|---|---|---|---|---|---|
| 113 | (3-chloro-phenyl)methyl | 638 | U | 638.1, 640.1 | 1.9Hz, 1H), 5.56(d, J=3.5Hz, 1H), 4.40(AB quartet, Δv=27.2Hz, J=12.0, 2H), 1.17(d, J=6.4Hz). 7.24(brs, 3H), 7.17–7.16(m, 4H), 7.06–7.03(m, 1H), 6.92,(d, J=1.9Hz, 1H), 6.83,(dd, J=8.5 and 1.8Hz, 1H), 5.58–5.57(m, 1H), 4.38 (AB quartet, Δv=24.0Hz, J= 12.2Hz, 2H), 1.18(d, J=6.4Hz, 3H). |
| 114 | (4-cyclohexylphenyl)-methyl | 685.8 | U | 685.9 | 7.26(s, 1H), 7.19(d, J=8.5Hz, 1H), 7.03(AB quartet, Δv=13.8Hz, J=8.1Hz, 4H), 6.93(d, J=1.8Hz, 1H), 6.86(dd, J=8.5 and 1.8Hz, 1H), 5.55(d, J=3.5Hz, 1H), 4.39 (AB quartet, Δv=20.6Hz, J= 11.6Hz, 2H) 1.15(d, J=6.2Hz, 3H). |
| 115 | (2-methyl-phenyl)methyl | 617.6 | U | 617.9 | 7.23(s, 1H), 7.16(d, J=8.3Hz, 1H), 7.11–7.01(m, 4H), 6.92(d, J= 1.9Hz, 1H), 6.82(dd, J=8.3 and 2.0Hz, 1H), 5.56(d, J=3.9Hz, 1H), 4.39(brs, 2H), 1.18(d, J=6.2Hz, 3H). |
| 116 | (2-fluorophenyl)methyl | 621.6 | U | 621.8 | 7.28–7.19(m, 3H), 7.17(d, J=8.3Hz, 1H), 7.01–6.95(m, 2H), 6.90(d, J=1.9Hz, 1H), 6.81(dd, J=8.3 and 1.8Hz, 1H), 5.54(d, J=4.2Hz, 1H), 4.48(brs, 2H), 1.19(d, J=6.5Hz, 3H). |
| 117 | (4-methoxy-phenyl)methyl | 633.7 | V | 634.2 | 7.25(s, 1H), 7.17(d, J=8.5Hz, 1H), 7.06(d, J=8.5Hz, 2H), 6.93 (d, J=1.9Hz, 1H), 6.85(dd, J=8.5 and 2.0Hz, 1H), 6.73(d, J=8.5Hz, 2H), 5.55(d, J=3.3Hz, 1H), 4.35 (AB quartet, Δv=20.5Hz, J= 11.4Hz, 2H), 1.14(d, J=6.3Hz, 3H). |
| 118 | (3-cyano-phenyl)methyl | 628.6 | W | 629.2 | 7.54(d, J=6.2Hz, 1H), 7.46–7.35 (m, 2H), 7.23(s, 1H), 7.15(d, J= 8.3Hz, 1H), 6.91(d, J=2.1Hz, 1H), 6.84(dd, J=8.4 and 1.9Hz, 1H), 5.6(d, J=3.7Hz, 1H), 4.45 (AB quartet, Δv=42.3, J= 12.3, 2H), 1.20(d, J=6.2Hz, 3H). |
| 119 | [(4-trifluoro-methyl)phenyl]methyl | 671.6 | W | 672.1 | 7.47(d, J=8.1Hz, 2H), 7.33(d, J= 8.1Hz, 2H), 7.24(s, 1H), 7.15(d, J= 8.3Hz, 1H), 6.91(d, J=1.9Hz, 1H), 6.84(dd, J=8.4 and 1.9Hz, 1H), 5.59(d, J=3.7Hz, 1H), 4.50 (AB quartet, Δv=27.1Hz, J= 12.7Hz, 2H), 1.20(d, J=6.5Hz, 3H) |
| 120 | (4-cyano-phenyl)methyl | 628.6 | W | 629.2 | 7.52(d, J=8.1Hz, 1H), 7.31(d, J= 8.1, 2H), 7.24(s, 1H), 7.15(d, J= 8.5Hz, 1H), 6.91(d, J=1.9Hz, 1H), 6.83(dd, J=8.5 and 1.9Hz, 1H), 5.59(d, J=3.7Hz, 1H), 4.48 (AB quartet, Δv=32.3Hz, J= 13.4Hz, 2H), 1.21(d, J=6.4Hz, 3H). |
| 121 | (3-methyl-phenyl)methyl | 617.6 | W | 618.3 | 7.25(s, 1H), 7.18(d, J=8.5Hz, 1H), 7.15–6.95(3m, 3H), 6.93(d, J= |

TABLE 4-continued

| Ex. | Y | Mol Wt | Pro. | Mass Spec | 1H NMR peaks (CD$_3$OD) |
|---|---|---|---|---|---|
| | | | | | 2.1Hz, 1H), 6.85(dd, J=8.5 and 2.1Hz, 1H), 5.55(d, J=3.5Hz, 1H) 4.38(AB quartet, Δv=14.1Hz, J=11.7Hz, 2H), 2.24(s, 3H) 1.15(d, J=6.4Hz, 3H). |
| 122 | (3,4-dimethyl-phenyl)methyl | 631.7 | W | 632.2 | 7.25(s, 1H), 7.18(d, J=8.5Hz, 1H), 6.96–6.93(m, 2H), 6.87–6.83 (m, 3H), 5.54(d, J=3.3Hz, 1H), 4.34(AB quartet, Δv=12.9Hz, J=11.5Hz, 2H), 2.17(s, 3H), 2.15(s, 3H), 1.13(d, J=6.2Hz, 3H). |
| 123 | phenylaminocarbonyl | 632.63 | X | 633.1 | 7.35–7.19(2m, 5H), 7.11(d, J=8.6 Hz, 1H) 6.96(t, J=7.4Hz, 1H) 6.91(d, J=2.1Hz, 1H), 6.73(dd, J=8.5 and 2.1Hz, 1H), 5.56(d, J=3.5Hz, 1H), 1.22(d, J=6.4Hz, 3H). |
| 124 | 3-fluorophenylamino-carbonyl | 650.62 | X | 651.1 | 7.26–7.20(m, 3H), 7.15,(d, J=8.5Hz, 1H), 7.05(dd, J=8.1 and 1.8Hz, 1H), 6.93(d, J=2.1Hz, 1H), 6.76–6.68(m, 2H), 5.58(d, J=3.5Hz, 1H), 1.24(d, J=6.4Hz, 3H). |
| 125 | 3,4-dichlorophenyl-aminocarbonyl | 701.52 | X | 701, 703 | 7.62(s, 1H), 7.33(d, J=8.9Hz, 1H), 7.23–7.20(m, 2H), 7.11(d, J=8.5Hz, 1H), 6.92(d, J=2.1Hz, 1H), 6.74(dd, J=8.5 and 2.1Hz, 1H), 5.56(d, J=3.1Hz, 1H), 4.91–4.8(m, 1H), 1.25(d, J=6.4Hz, 3H). |
| 126 | 4-chlorophenylamino-carbonyl | 667.07 | X | 667, 669 | 7.35–7.32(m, 2H), 7.20–7.19(m, 3H), 7.12(d, J=8.5Hz, 1H), 6.93 (d, J=2.1Hz, 1H), 6.75(dd, J=8.5 and 2.1Hz, 1H), 5.57(d, J=3.1Hz, 1H), 1.24(d, J=6.4Hz, 3H). |
| 127 | 4-methoxyphenyl-aminocarbonyl | 662.65 | X | 663 | 7.23–7.21(m, 3H), 7.13(d, J=8.5Hz, 1H), 6.93,(d, J=1.9Hz, 1H), 6.80–6.76(m, 3H), 5.58(brs, 1H), 1.23,(d, J=6.4Hz, 3H). |
| 128 | [(4-fluorophenyl)methyl]-aminocarbonyl | 664.5 | Y | 665.1 | 7.24(br s, 3H), 7.10(d, J=8.3Hz, 1H), 7.00(m, 2H), 6.6(br s, 1H), 6.77(br d, J=8.1Hz, 1H), 5.52(br s, 1H), 4.9–4.80(m, 1H), 1.19(br d, J=6.4Hz, 1H). |
| 129 | (phenylmethyl)amino-carbonyl | 646.6 | Y | 647.2 | 7.7.3–7.1(m, 6H), 7.5(d, J=8.3Hz, 1H), 6.82(br s, 1H), 6.66(d, J=8.3, 1H), 5.50(d, J=5.2Hz, 1H), 4.83–4.80(m, 1H), 1.20(d, J=6.9Hz, 3H). |
| 130 | [(3,4-dichloro phenyl)methyl]amino-carbonyl | 715.5 | Y | 715, 717 | 7.39(s, 1H), 7.23(s, 1H), 7.18–7.01 (m, 3H), 6.86(d, J=1.6Hz. 1H), 6.77–6.72(m, 1H), 5.52(d, J=2.5Hz, 1H), 4.85–4.82(m, 1H), 1.20(d, J=6.5Hz, 3H). |

TABLE 4-continued

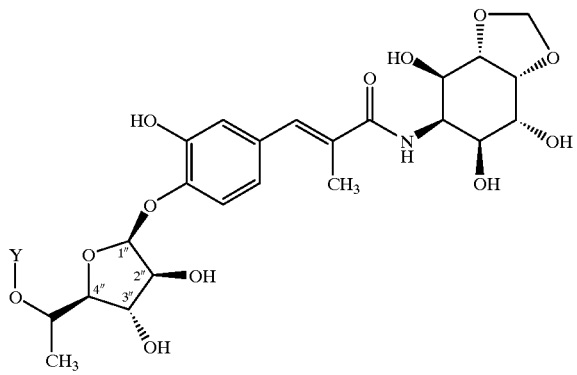

| Ex. | Y | Mol Wt | Pro. | Mass Spec | 1H NMR peaks (CD$_3$OD) |
|---|---|---|---|---|---|
| 131 | [(4-chlorophenyl)methyl]-aminocarbonyl | 681.1 | Y | 681.1, 683.1 | 7.3–7.2(m, 4H) 7.11(d, J=8.5Hz, 1H), 6.77(d, J=7.7, 1H), 5.5(br s, 1H), 4.84–4.80(m, 1H), 1.19(d, J=6.4Hz). |

TABLE 5

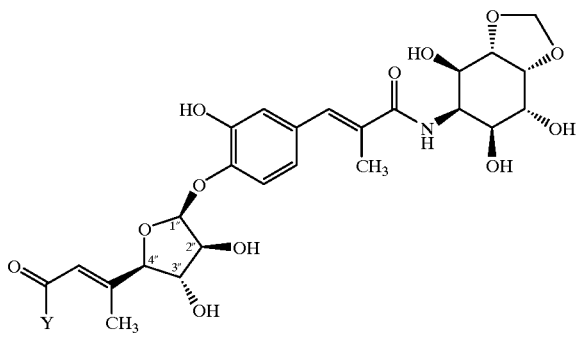

| Ex. | Y | Mol Wt | Pro. | Mass spec. | 1H NMR peaks (CD$_3$OD) |
|---|---|---|---|---|---|
| 132 | ethoxy | 581.58 | AA | 582.2 | 5.80(bs, 1H), 5.59(d, J=4.6Hz, 1H), 4.02(q, J=7.1Hz, 2H), 2.04(d, J=1.2Hz, 3H), 1.15(t, J=7.1Hz, 3H) |
| 133 | hydroxy | 553.52 | BB | 554.1 | 5.84(bs, 1H), 5.56(d, J=3.9Hz, 1H), 1.95(d, J=1.2Hz, 3H) |
| 134 | (phenylmethyl)amino | 642.67 | CC | 643.3 | 7.21(m, 5H), 5.90(s, 1H), 5.60 (d, J=2.3Hz, 1H), 4.32(s, 2H), 1.99(s, 3H) |
| 135 | [(3-fluorophenyl)-methyl]amino | 660.66 | DD | 661.2 | 7.30(m, 1H), 7.03(d, J=7.9Hz, 1H), 6.94(m, 2H), 5.93(s, 1H), 5.61(d, J=3.8Hz, 1H), 4.34(s, 2H), 2.00(d, J=1.3Hz, 3H) |
| 136 | cyclohexylamino | 634.69 | EE, L | 635.1 | 5.82(s, 1H), 5.60(d, J=3.9Hz, 1H), 3.59(m, 1H), 1.95(d, J=1.2Hz, 3H), 1.78(bd, J=11.8Hz, 2H), 1.70(bd, J=13.3Hz, 2H), 1.59(bd, J=12.7Hz, 1H), 1.31(m, 2H), 1.14(m, 3H) |
| 137 | 4-pyridylmethylamino | 643.65 | EE, J | 644.3 | 8.39(m, 2H), 7.23(m, 2H), 5.93 (bs, 1H), 5.60(d, J=3.7Hz, 1H), 4.36(AB quartet, Δv=20.3Hz, J=16.2Hz, 2H), 1.99 (d, J=1.2Hz, 3H) |

TABLE 5-continued

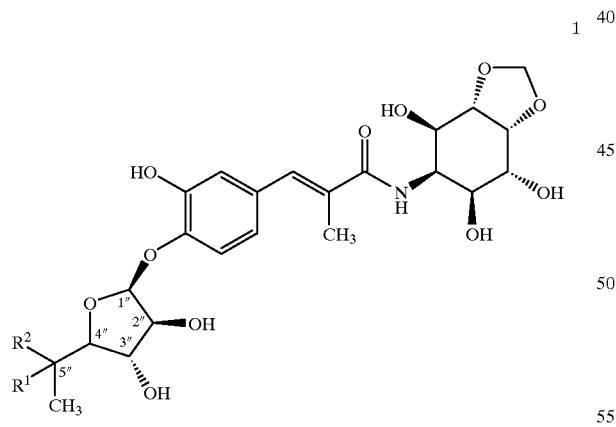

| Ex. | Y | Mol Wt | Pro. | Mass spec. | 1H NMR peaks (CD$_3$OD) |
|---|---|---|---|---|---|
| 138 | (benzodioxole-methyl-amino, HN-CH$_2$-benzo[1,3]dioxole) | 686.68 | EE, L | 687.2 | 6.68(m, 3H), 5.87(s, 2H), 5.87 (bs, 1H), 5.59(d, J=3.7Hz, 1H), 1.97(d, J=1.2Hz, 3H) |
| 139 | 2-(dimethylamino)ethyl-amino | 623.66 | EE, N | 623.8 | 5.84(bs, 1H), 5.57(d, J=3.7Hz, 1H), 3.27(t, J=6.8Hz, 2H), 2.39(t, J=6.7Hz, 2H), 2.21(s, 6H), 1.96(d, J=1.2Hz, 3H) |
| 140 | 2-furanylmethylamino | 632.63 | EE, J | 632.8 | 7.35(dd, J=1.9, 0.8Hz, 1H), 6.28(dd, J=3.3, 1.9Hz, 1H), 6.15(dd, J=3.2, 0.7Hz, 1H), 5.85(bs, 1H), 5.57(d, J=3.7Hz, 1H), 4.29(s, 2H), 1.96(d, J=1.2Hz, 3H) |

What is claimed is:

1. A compound of the formula

1 or a pharmaceutically acceptable salt, prodrug or solvate thereof wherein:

$R^1$ is H and $R^2$ is —NR$^3$R$^4$, —NR$^4$C(O)R$^3$, —OC(O)NR$^3$R$^4$ or —OR$^3$;

or $R^1$ and $R^2$ are taken together to form =N—OR$^3$, =CR$^4$R$^3$, =CR$^4$C(O)R$^3$, =CR$^4$C(O)OR$^3$, or =CR$^4$C(O)NR$^3$R$^4$;

each $R^3$ is independently selected from the group consisting of H, $C_1$–$C_{10}$ alkyl, $C_2$–$C_{10}$ alkenyl, —(CH$_2$)$_t$ ($C_3$–$C_{10}$ cycloalkyl), —(CH$_2$)$_t$($C_6$–$C_{10}$ aryl), and —(CH$_2$)$_t$(4–10 membered heterocyclic), wherein t is an integer ranging from 0 to 5, said alkyl group optionally contains 1 or 2 hetero moieties selected from O, —S(O)$_j$— wherein j is an integer ranging from 0 to 2, and —N(R$^7$)— with the proviso that two O atoms, two S atoms, or an O and S atom are not attached directly to each other; said cycloalkyl, aryl and heterocyclic $R^3$ groups are optionally fused to a benzene ring, a $C_5$–$C_8$ saturated cyclic group, or a 4–10 membered heterocyclic group; the —(CH$_2$)$_t$— moieties of the foregoing $R^3$ groups optionally include a carbon-carbon double or triple bond where t is an integer between 2 and 5; and the foregoing $R^3$ groups, except H but including any optional fused rings referred to above, are optionally substituted by 1 to 5 $R^5$ groups, with the proviso that $R^3$ is not H, methyl or ethyl where $R^1$ is H and $R^2$ is —OR$^3$;

each $R^4$ is independently H or $C_1$–$C_{10}$ alkyl;

each $R^5$ is independently selected from the group consisting of $C_1$–$C_{10}$ alkyl, $C_3$–$C_{10}$ cycloalkyl, halo, cyano, nitro, trifluoromethyl, difluoromethoxy, trifluoromethoxy, azido, —OR$^6$, —C(O)R$^6$, —C(O)OR$^6$, —NR$^7$C(O)OR$^9$, —OC(O)R$^6$, —NR$^7$SO$_2$R$^9$, —SO$_2$NR$^6$R$^7$, —NR$^7$C(O)R$^6$, —C(O)NR$^6$R$^7$, —NR$^6$R$^7$, —S(O)$_j$(CH$_2$)$_m$(C$_6$–C$_{10}$ aryl), —S(O)$_j$(C$_1$–C$_6$ alkyl), wherein j is an integer ranging from 0 to 2, —(CH$_2$)$_m$(C$_6$–C$_{10}$ aryl), —O(CH$_2$)$_m$(C$_6$–C$_{10}$ aryl), —NR$^7$(CH$_2$)$_m$(C$_6$–C$_{10}$ aryl), and —(CH$_2$)$_m$(4–10 membered heterocyclic), wherein m is an integer ranging from 0 to 4; said alkyl group optionally contains 1 or 2 hetero moieties selected from O, —S(O)$_j$— wherein j is an integer ranging from 0 to 2, and —N(R$^7$)— with the proviso that two O atoms, two S atoms, or an O and S atom are not attached directly to each other; said cycloalkyl, aryl and heterocyclic R$^5$ groups are optionally fused to a C$_6$–C$_{10}$ aryl group, a C$_5$–C$_8$ saturated cyclic group, or a 4–10 membered heterocyclic group; and said alkyl, cycloalkyl, aryl and heterocyclic R$^5$ groups are optionally substituted by 1 to 5 substituents independently selected from the group consisting of halo, cyano, nitro, trifluoromethyl, difluoromethoxy, trifluoromethoxy, azido, —NR$^7$SO$_2$R$^9$, —SO$_2$NR$^6$R$^7$, —C(O)R$^6$, —C(O)OR$^6$, —OC(O)R$^6$, —NR$^7$C(O)OR$^9$, —NR$^7$C(O)R$^6$, —C(O)NR$^6$R$^7$, —NR$^6$R$^7$, —OR$^6$, C$_1$–C$_{10}$ alkyl, —(CH$_2$)$_m$(C$_6$–C$_{10}$ aryl), and —(CH$_2$)$_m$(4–10 membered heterocyclic), wherein m is an integer ranging from 0 to 4;

each R$^6$ is independently selected from the group consisting of H, C$_1$–C$_{10}$ alkyl, C$_3$–C$_{10}$ cycloalkyl, —(CH$_2$)$_m$(C$_6$–C$_{10}$ aryl), and —(CH$_2$)$_m$(4–10 membered heterocyclic), wherein m is an integer ranging from 0 to 4; said alkyl group optionally includes 1 or 2 hetero moieties selected from O, —S(O)$_j$— wherein j is an integer ranging from 0 to 2, and —N(R$^7$)— with the proviso that two O atoms, two S atoms, or an O and S atom are not attached directly to each other; said cycloalkyl, aryl and heterocyclic R$^6$ groups are optionally fused to a C$_6$–C$_{10}$ aryl group, a C$_5$–C$_8$ saturated cyclic group, or a 4–10 membered heterocyclic group; and the foregoing R$^6$ substituents, except H, are optionally substituted by 1 to 5 substituents independently selected from the group consisting of halo, cyano, nitro, trifluoromethyl, difluoromethoxy, trifluoromethoxy, azido, —C(O)R$^7$, —C(O)OR$^7$, —OC(O)R$^7$, —NR$^7$C(O)R$^8$, —C(O)NR$^7$R$^8$, —NR$^7$R$^8$, hydroxy, C$_1$–C$_6$ alkyl, and C$_1$–C$_6$ alkoxy;

each R$^7$ and R$^8$ is independently H or C$_1$–C$_6$ alkyl; and, R$^9$ is selected from the substituents provided in the definition of R$^6$ except H.

2. A compound according to claim 1 wherein R$^1$ and R$^2$ are taken together to form =N—OR$^3$, and R$^3$ is C$_1$–C$_4$ alkyl, C$_2$–C$_4$ alkenyl, —(CH$_2$)$_t$(C$_6$–C$_{10}$ aryl) or —(CH$_2$)$_t$(4–10 membered heterocyclic), wherein t is an integer ranging from 0 to 3, the heterocyclic group is optionally fused to a benzene ring, the aryl group is optionally fused to a 5 or 6 membered heterocyclic group, and the foregoing R$^3$ groups, including said optionally fused moieties, are optionally substituted by 1 to 5 substituents independently selected from the group consisting of nitro, halo, C$_1$–C$_3$ alkoxy, C$_1$–C$_4$ alkyl, trifluoromethyl, acetamido, tert-butoxycarbonylamino, tert-butoxycarbonylaminomethyl, tert-butoxycarbonyl, —NR$^6$R$^7$, phenyl, cyclohexyl, carboxy, aminomethyl, difluoromethoxy, trifluoromethoxy, cyano, piperidinyl, morpholino, phenoxy, and phenylthio.

3. A compound according to claim 1 wherein R$^1$ and R$^2$ are taken together to form =N—OR$^3$, and R$^3$ is —(CH$_2$)$_t$(C$_6$–C$_{10}$ aryl) or —(CH$_2$)$_t$(4–10 membered heterocyclic), wherein t is an integer ranging from 0 to 3, the heterocyclic group is optionally fused to a benzene ring, the aryl group is optionally fused to a 5 or 6 membered heterocyclic group, and the foregoing R$^3$ groups, including said optionally fused moieties, are optionally substituted by 1 to 5 substituents independently selected from the group consisting of nitro, halo, C$_1$–C$_3$ alkoxy, C$_1$–C$_4$ alkyl, trifluoromethyl, acetamido, tert-butoxycarbonyl, tert-butoxycarbonylamino, —NR$^6$R$^7$, phenyl, cyclohexyl, carboxy, tert-butoxycarbonylaminomethyl, aminomethyl, difluoromethoxy, trifluoromethoxy, cyano, piperidinyl, morpholino, phenoxy, and phenylthio.

4. A compound according to claim 1 wherein R$^1$ is H, R$^2$ is —NR$^3$R$^4$, R$^4$ is H or methyl, and R$^3$ is —(CH$_2$)$_t$(C$_6$–C$_{10}$ aryl) or —(CH$_2$)$_t$(4–10 membered heterocyclic), wherein t is an integer ranging from 0 to 2, and the R$^3$ group is optionally substituted by 1 to 5 substituents independently selected from the group consisting of halo, C$_1$–C$_3$ alkoxy, C$_1$–C$_4$ alkyl, and trifluoromethyl.

5. A compound according to claim 1 wherein R$^1$ is H, R$^2$ is —NR$^4$C(O)R$^3$, R$^4$ is H, and R$^3$ is C$_3$–C$_6$ cycloalkyl, —(CH$_2$)$_t$(C$_6$–C$_{10}$ aryl) or —(CH$_2$)$_t$(4–10 membered heterocyclic), wherein t is an integer ranging from 0 to 2, the aryl group is optionally fused to a 5 or 6 membered heterocyclic group, the heterocyclic group is optionally fused to a benzene ring, and the foregoing R$^3$ groups, including said optionally fused moieties, are optionally substituted by 1 to 5 substituents independently selected from the group consisting of halo, C$_1$–C$_3$ alkoxy, C$_1$–C$_4$ alkyl, and trifluoromethyl.

6. A compound according to claim 1 wherein R$^1$ and R$^2$ are taken together to form =CR$^4$C(O)OR$^3$ or =CR$^4$C(O)NR$^3$R$^4$, R$^4$ is H, and R$^3$ is H, C$_1$–C$_6$ alkyl, C$_3$–C$_6$ cycloalkyl, —(CH$_2$)$_t$(4–10 membered heterocyclic), or —(CH$_2$)$_t$(C$_6$–C$_{10}$ aryl) wherein t is an integer ranging from 0 to 2, the aryl group is optionally fused to a 5 or 6 membered heterocyclic group, the heterocyclic group is optionally fused to a benzene ring, and the foregoing R$^3$ groups, except H but including said optionally fused moieties, are optionally substituted by 1 to 5 substituents independently selected from the group consisting of halo, C$_1$–C$_3$ alkoxy, C$_1$–C$_4$ alkyl, —NR$_6$R$^7$ and trifluoromethyl.

7. A compound according to claim 1 wherein R$^1$ is H, R$^2$ is —OR$^3$, and R$^3$ is C$_1$–C$_4$ alkyl, —(CH$_2$)$_t$(4–10 membered heterocyclic), or —(CH$_2$)$_t$(C$_6$–C$_{10}$ aryl) wherein t is an integer ranging from 1 to 2, the aryl group is optionally fused to a 5 or 6 membered heterocyclic group, the heterocyclic group is optionally fused to a benzene ring, and the foregoing R$^3$ groups, including said optionally fused moieties, are optionally substituted by 1 to 5 substituents independently selected from the group consisting of halo, C$_1$–C$_3$ alkoxy, C$_1$–C$_4$ alkyl, cyclohexyl, cyano, trifluoromethyl, benzyloxy and trifluoromethyl.

8. A compound according to claim 1 wherein R$^1$ is H, R$^2$ is —OC(O)NR$^3$R$^4$, R$^4$ is H, and R$^3$ is —(CH$_2$)$_t$(C$_6$–C$_{10}$ aryl) wherein t is an integer ranging from 0 to 2, and the R$^3$ group is optionally substituted by 1 to 5 substituents independently selected from the group consisting of halo, C$_1$–C$_3$ alkoxy, C$_1$–C$_4$ alkyl, and trifluoromethyl.

9. A compound according to claim 1 wherein said compound is selected from the group consisting of:

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(benzofuran-2-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(benzofuran-2-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)- propenyl]amino]-1,2-O-methylene-D-neo-inositol, (Z)-O-phenylmethyloxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-phenylmethyloxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-chlorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3,4-dichlorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3,4-dichlorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-pyridinyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-(4-morpholinyl)phenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[cyclohexylmethyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-fluorophenyl)methyl]oxime;

5-Deoxy-5-[[3-[4-[(6-deoxy-b-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,4-dichlorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3,4-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(furan-3-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(furan-3-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(1,3-benzodioxol-5-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(1,3-benzodioxol-5-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chlorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-cyclohexylphenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-aminophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[[(4-aminomethyl)phenyl]methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[3-(4-chlorophenyl)propyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[3-(4-chlorophenyl)propyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-(trifluoromethoxy)phenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-(1-piperidinyl)phenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[2-(phenylthio)ethyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(benzofuran-5-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(benzofuran-5-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2-phenylpyrimidin-5-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-fluoro-4-methoxyphenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3,4-dihydro-2H-1-benzopyran-4-yl)methyl]oxime;

5-Deoxy-5-[[3-[4-[(5,6-dideoxy-5-(methyl(phenylmethyl)amino-α-L-galacto-furanos-1-yl)oxy]-3-hydroxyphenyl]-2-methyl-1-oxo-2-(E)-propenyl]amino]-1,2-O-methylene-D-neo-inositol;

5-Deoxy-5-[[3-[4-[(5,6-dideoxy-5-phenylamino-α-L-galacto-furanos-1-yl)oxy]-3-hydroxyphenyl]-2-methyl-1-oxo-2-(E)-propenyl]amino]-1,2-O-methylene-D-neo-inositol;

5-Deoxy-5-[[3-[4-[(6-deoxy-5-O-[(3,4-dichlorophenyl)methyl]-β-D-altro-furanos-1-yl)oxy]-3-hydroxyphenyl]-2-methyl-1-oxo-2-(E)-propenyl]amino]-1,2-O-methylene-D-neo-inositol;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(furan-2-yl)methyl]oxime;

5-Deoxy-5-[[3-[4-[(5-methyl-β-D-arabino-hept-5-(E)-enofuranuron-1-ylic acid)oxy]-3-hydroxyphenyl]-2- methyl-1-oxo-2-(E)-propenyl]amino]-1,2-O-methylene-D-neo-inositol, ethyl ester;

5-Deoxy-5-[[3-[4-[[N-(furan-2-yl)methyl]-(5-methyl-β-D-arabino-hept-5-(E)-enofuranuron-1-yl-amide)oxy]-3-hydroxyphenyl]-2-methyl-1-oxo-2-(E)-propenyl]amino]-1,2-O-methylene-D-neo-inositol;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[3-(phenyl)propyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(2-propen-1-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(2-propen-1-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-methylphenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-methoxyphenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-(trifluoromethyl)phenyl)methyl]oxime;

5-Deoxy-5-[[3-[4-[(6-deoxy-β-O-[(4-chlorophenyl)methyl]-β-D-altro-furanos-1-yl)oxy]-3-hydroxyphenyl]-2-methyl-1-oxo-2-(E)-propenyl]amino]-1,2-O-methylene-D-neo-inositol;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[diphenylmethyl]oxime;

5-Deoxy-5-[[3-[4-[(6-deoxy-5-phenylcarbamate-β-D-altro-furanos-1-yl)oxy]-3-hydroxyphenyl]-2-methyl-1-oxo-2-(E)-propenyl]amino]-1,2-O-methylene-D-neo-inositol;

5-Deoxy-5-[[3-[4-[(6-deoxy-5-[(3,4-dichlorophenyl)methyl]carbamate-β-D-altro-furanos-1-yl)oxy]-3-hydroxyphenyl]-2-methyl-1-oxo-2-(E)-propenyl]amino]-1,2-O-methylene-D-neo-inositol;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chlorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chloro-2-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chloro-2-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chloro-4-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chloro-4-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chloro-5-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chloro-5-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(5-chloro-2-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(5-chloro-2-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3,5-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3,5-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-chloro-3-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-chloro-3-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-chloro-1,3-benzodioxol-6-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-chloro-1,3-benzodioxol-6-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(5-chloro-1,3-benzodioxol-6-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(5-chloro-1,3-benzodioxol-6-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-chloro-1,3-benzodioxol-5-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-chloro-1,3-benzodioxol-5-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,3-dihydrobenzofuran-6-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,3-dihydrobenzofuran-6-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,3-dihydrobenzofuran-5-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)- propenyl]amino]-1,2-O-methylene-D-neo-inositol, (Z)-O-[(2,3-dihydrobenzofuran-5-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(1,2,3,4-tetrahydronaphthalen-1-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(1,2,3,4-tetrahydronaphthalen-1-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(7-chloro-1,2,3,4-tetrahydronaphthalen-1-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(7-chloro-1,2,3,4-tetrahydronaphthalen-1-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(7-fluoro-1,2,3,4-tetrahydronaphthalen-1-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(7-fluoro-1,2,3,4-tetrahydronaphthalen-1-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(8-chloro-3,4-dihydro-2H-1-benzopyran-4-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(8-chloro-3,4-dihydro-2H-1-benzopyran-4-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(6-chloro-3,4-dihydro-2H-1-benzopyran-4-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(6-chloro-3,4-dihydro-2H-1-benzopyran-4-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(8-fluoro-3,4-dihydro-2H-1-benzopyran-4-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(8-fluoro-3,4-dihydro-2H-1-benzopyran-4-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(6-fluoro-3,4-dihydro-2H-1-benzopyran-4-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(6-fluoro-3,4-dihydro-2H-1-benzopyran-4-yl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(quinolin-2-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(quinolin-2-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(quinolin-3-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(quinolin-3-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[4-(phenylmethyl)phenylmethyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[4-(phenylmethyl)phenylmethyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[4-(phenoxy)phenylmethyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[4-(phenoxy)phenylmethyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3,5-dichlorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3,5-dichlorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(phenyl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(phenyl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(3-chloro-4-fluorophenyl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(3-chloro-4-fluorophenyl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-chlorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3,4-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,4-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,4-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)- propenyl]amino]-1,2-O-methylene-D-neo-inositol, (Z)-O-[(2,1,3-benzoxadiazol-5-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,1,3-benzoxadiazol-5-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,3,5,6-tetrafluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,3,5,6-tetrafluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,3-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,3-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-phenyl-furan-3-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-phenyl-furan-3-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-phenyl-furan-2-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-phenyl-furan-2-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,3-difluoro-6-methoxyphenyl)methyl]oxime;

5-Deoxy-5-[[3-[4-[(6-deoxy-β-D-arabino-hexafuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,3-difluoro-6-methoxyphenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1oxo-2-(E)-propenyl]amino]-1,2-O-methylene-D-neo-inositol, (E)-O-[(3-chloro-thiophen-2-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chloro-thiophen-2-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(5-chloro-thiophen-2-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(5-chloro-thiophen-2-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chloro-2,6-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chloro-2,6-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2-fluorophenyl)methyl]oxime;

5-Deoxy-5-[[3-[4-[(6-deoxy-β-D-arabino-hexafuranos-5-ulos-1-yl)oxy]-3-hydroxyphenyl]-2-methyl-1-oxo-2-(E)-propenyl]amino]-1,2-O-methylene-D-neo-inositol, (E)-O-[1-(3-chlorophenyl)ethyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(3-difluoromethoxy-phenyl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(3-difluoromethoxy-phenyl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-(4-difluoromethoxy-phenyl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(4-difluoromethoxy-phenyl)oxime;

and the pharmaceutically acceptable salts and solvates of said compounds.

10. A compound according to claim 1 wherein said compound is selected from the group consisting of:

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(1,3-benzodioxol-5-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chlorophenyl)methyl]oxime;

5-Deoxy-5-[[3-[4-[(6-deoxy-β-D-arabino-hexafuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chlorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositoi, (E)-O-[(3-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(benzofuran-2-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3,5-dichlorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3,5-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3,5-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)- propenyl]amino]-1,2-O-methylene-D-neo-inositol, (Z)-O-[(3-chloro-2-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chloro-2-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chloro-4-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3-chloro-4-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-chloro-3-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-chloro-3-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-chlorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(4-chlorophenyl)methyl]oxime;

5-Deoxy-5-[[3-[4-[(6-deoxy-β-D-arabina-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(4-phenyl-furan-2-yl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(3-chloro-5-fluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(3,4-difluorophenyl)methyl]oxime;

5-Deoxy-5-[[3-[4-[(6-deoxy-β-D-arabino-hexafuranos-5-ulos-1-yl)oxy]-3-hydroxyphenyl]-2-methyl-1-oxo-2-(E)-propenyl]amino]-1,2-O-methylene-D-neo-inositol, (Z)-O-[(3,4-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,3-difluorophenyl)methyl]oxime;

5-Deoxy-5-[[3-[4-[(6-deoxy-β-D-arabino-hexafuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,4-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-[(2,4-difluorophenyl)methyl]oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(2,3,5,6-tetrafluorophenyl)methyl]oxime;

5-Deoxy-5-[[3-[4-[(6-deoxy-β-D-arabino-hexafuranos-5-ulos-1-yl)oxy]-3-hydroxyphenyl]-2-methyl-1-oxo-2-(E)-propenyl]amino]-1,2-O-methylene-D-neo-inositol, (Z)-O-(3-chloro-4-fluorophenyl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (E)-O-(3-chloro-4-fluorophenyl)oxime;

5-Deoxy-5-[[3-[4-[(6-deoxy-β-D-arabino-hexofuranos-5-ulos-1-yl)oxy]-3-hydroxyphenyl]-2-methyl-1-oxo-2-(E)-propenyl]amino]-1,2-O-methylene-D-neo-inositol, (Z)-O-[(5-chloro-thiophen-2-yl)methyl]oxime;

and the pharmaceutically acceptable salts and solvates of said compounds.

11. A pharmaceutical composition for the treatment of a bacterial infection, a protozoal infection, or a disorder caused by a bacterial infection or a protozoal infection, in a mammal, fish, or bird which comprises a therapeutically effective amount of a compound of claim 1 and a pharmaceutically acceptable carrier.

12. A method of treating a bacterial infection, a protozoal infection, or a disorder caused by a bacterial infection or a protozoal infection, in a mammal, fish, or bird which comprises administering to said mammal, fish or bird a therapeutically effective amount of a compound of claim 1.

13. A method of preparing a composition containing hygromycin A and epi-hygromycin, wherein the ratio of hygromycin A to epi-hygromycin is at least 10:1, which comprises fermenting *Streptomyces hygroscopicus* in media having a pH less than 6.9 at a temperature ranging from 25° C. to 35° C.

14. A method according to claim 13 wherein said *Streptomyces hygroscopicus* is *Streptomyces hygroscopicus* NRRL2388, or a mutant thereof, said pH ranges from 6.2 to 6.7, said temperature is about 29° C., and the ratio of hygromycin A to epi-hygromycin is at least 14:1.

15. The method of claim 13 and further comprising maintaining said composition at a pH of about 6.0 to 6.4 and maintaining the temperature of said composition at a temperature ranging from 25° C. to 35° C. during purification of said hygromycin A to an oil.

16. The method of claim 15 wherein said pH is maintained at about 6.0.

17. A method of preparing a compound of claim 1 wherein $R^1$ and $R^2$ are taken together to form $=N-OR^3$, which comprises treating hygromycin A with a hydroxylamine of the formula $H_2N-OR^3$, or a salt of said compound, where $R^3$ is as defined in claim 1, in an inert solvent, optionally in the presence of a base if the salt of the hydroxylamine is used, at a temperature ranging from about 0° C. to 65° C.

18. The method of claim 17 wherein said inert solvent is methanol, ethanol, or pyridine, or a mixture of the foregoing solvents, said base is $Na_2CO_3$ or $K_2CO_3$, and said temperature ranges from from 0° C. to 25° C.

* * * * *